US006870056B1

(12) United States Patent
South et al.

(10) Patent No.: US 6,870,056 B1
(45) Date of Patent: Mar. 22, 2005

(54) SUBSTITITUTED POLYCYCLIC ARYL AND HETEROARYL PYRIDONES USEFUL FOR SELECTIVE INHIBITION OF THE COAGULATION CASCADE

(75) Inventors: Michael S. South, St. Louis, MO (US); Qingieng Zeng, Ballwin, MO (US); Melvin L. Rueppel, St. Louis, MO (US); Ashton T. Hamme, II, Ridgeland, MS (US)

(73) Assignee: Pharmacia Corporation, Chicago, IL (US)

( * ) Notice: Subject to any disclaimer, the term of this patent is extended or adjusted under 35 U.S.C. 154(b) by 275 days.

(21) Appl. No.: 09/716,962

(22) Filed: Nov. 20, 2000

Related U.S. Application Data

(63) Continuation-in-part of application No. 09/574,740, filed on May 18, 2000.
(60) Provisional application No. 60/134,811, filed on May 19, 1999.

(51) Int. Cl.$^7$ ...................... A61K 31/47; C07D 251/00; C07D 215/16; C07D 215/20
(52) U.S. Cl. ...................... 546/153; 546/141; 546/192; 544/111; 544/180; 544/279; 514/111; 514/305; 514/306; 514/309; 514/310; 514/312; 514/313; 514/300
(58) Field of Search ................................ 514/111, 300, 514/305, 306, 309, 310, 312, 313; 544/111, 180, 279; 546/141, 153, 192

(56) References Cited

U.S. PATENT DOCUMENTS

| | | | |
|---|---|---|---|
| 4,489,096 A | 12/1984 | Terao et al. | |
| 4,851,413 A | 7/1989 | Terao et al. | |
| 4,992,469 A | 2/1991 | Ozawa et al. | |
| 5,008,267 A | 4/1991 | Katakami et al. | |
| 5,032,602 A | * 7/1991 | Fey et al. .................... | 514/345 |
| 5,304,658 A | 4/1994 | Terao et al. | |
| 5,441,960 A | 8/1995 | Bernstein et al. | |
| 5,656,645 A | 8/1997 | Tamura et al. | |
| 5,658,930 A | 8/1997 | Tamura et al. | |
| 5,668,289 A | 9/1997 | Sanderson et al. | |
| 5,741,819 A | 4/1998 | Illig et al. | |
| 5,792,779 A | 8/1998 | Sanderson et al. | |
| 5,861,380 A | 1/1999 | Gyorkos et al. | |
| 5,866,573 A | 2/1999 | Sanderson et al. | |
| 5,869,487 A | 2/1999 | Coburn et al. | |
| 5,872,138 A | 2/1999 | Naylor-Olsen et al. | |
| 6,011,158 A | 1/2000 | Tamura et al. | |
| 6,037,356 A | 3/2000 | Lu et al. | |
| 6,180,627 B1 | 1/2001 | Blagg et al. | |
| 6,252,082 B1 | * 6/2001 | Lassalle et al. ............. | 546/293 |

FOREIGN PATENT DOCUMENTS

| | | |
|---|---|---|
| DE | 198 51 421 A1 | 5/2000 |
| EP | 0 354 495 A1 | 2/1990 |
| EP | 826 671 A1 | 3/1998 |
| EP | 936 216 A1 | 8/1999 |
| EP | 940 400 A1 | 9/1999 |
| EP | 997 474 A1 | 5/2000 |
| EP | 528 633 B1 | 10/2000 |
| HU | 210056 B | 1/1995 |
| WO | WO 93/21214 A1 | 10/1993 |
| WO | WO 96/18644 A1 | 6/1996 |
| WO | WO 96/33974 A1 | 10/1996 |
| WO | WO 96/39380 A1 | 12/1996 |
| WO | WO 96/40100 A1 | 12/1996 |
| WO | WO 97/01338 A1 | 1/1997 |
| WO | WO 97/30708 A1 | 8/1997 |
| WO | WO 97/40024 A1 | 10/1997 |
| WO | WO 97/46207 A2 | 12/1997 |
| WO | WO 98/08840 A1 | 3/1998 |
| WO | WO 98/09949 A1 | 3/1998 |
| WO | WO 98/09987 A1 | 3/1998 |
| WO | WO 98/10763 A1 | 3/1998 |
| WO | WO 98/16525 A1 | 4/1998 |
| WO | WO 98/16547 A1 | 4/1998 |
| WO | WO 98/17274 A1 | 4/1998 |
| WO | WO 98/31670 A1 | 7/1998 |
| WO | WO 98/42342 A1 | 10/1998 |
| WO | WO 98/47876 A1 | 10/1998 |
| WO | WO 98/50420 A1 | 11/1998 |
| WO | WO 99/00121 A1 | 1/1999 |
| WO | WO 99/00126 A1 | 1/1999 |
| WO | WO 99/00128 A1 | 1/1999 |
| WO | WO 99/11267 A1 | 3/1999 |
| WO | WO 99/26920 A1 | 6/1999 |
| WO | WO 99/26926 A1 | 6/1999 |
| WO | WO 99/36426 A1 | 7/1999 |
| WO | WO 99/43660 A1 | 9/1999 |
| WO | WO 99/48892 A1 | 9/1999 |
| WO | WO 99/59591 A1 | 11/1999 |
| WO | WO 99/61442 A1 | 12/1999 |
| WO | WO 99/62538 A1 | 12/1999 |
| WO | WO 99/64446 A1 | 12/1999 |
| WO | WO 00/18762 A1 | 4/2000 |
| WO | WO 00/26210 A1 | 5/2000 |
| WO | WO 00/26211 A1 | 5/2000 |
| WO | WO 00/32574 A1 | 6/2000 |
| WO | WO 00/39102 A1 | 7/2000 |
| WO | WO 00/69826 A1 | 11/2000 |
| WO | WO 00/69832 A1 | 11/2000 |
| WO | WO 00/69833 A1 | 11/2000 |

OTHER PUBLICATIONS

Majerus, et al. "Anticoagulant, Thrombolytic, and Antiplatlet Drugs." Goodman & Gilman's The Pharmacological Basis of Therapeutics, Ninth Edition, 1996, pp. 1341–1359, McGraw–Hill, New York.

(List continued on next page.)

Primary Examiner—Richard L. Raymond
Assistant Examiner—Tamthom N. Truong

(57) ABSTRACT

The invention relates to substituted polycyclic aryl and heteroaryl pyridone compounds useful inhibitors of serine proteases of the coagulation cascade and compounds, compositions and methods for anticoagulant therapy for the treatment and prevention of a variety of thrombotic conditions including coronary artery and cerebrovascular diseases.

36 Claims, No Drawings

OTHER PUBLICATIONS

Handin, R., "Bleeding and Thrombosis." Harrison's Principles of Internal Medicine, 12th Edition, 1991, pp. 348–353, McGraw–Hill, Inc., New York.

Sanderson et al., "L–373,890, An Achiral, Noncovalent, Subnamomolar Thrombin Inhibitor." Bioorganic & Medicinal Chemistry Letters, vol. 7, No. 12, pp. 1497–1500, 1997.

Rauch, et al., Thrombus Formation on Atherosclerotic Plaques: Pathogenesis and Clinical Consequences, Annals of Internal Medicine, 2001, pp. 224–233, vol. 134—No. 3.

Van Aken, et al., Anticoagulation: The Present and Future, Clin. Appl. Thrombosis/Hemostasis, 2001, pp. 195–204, vol. 7—No. 3.

Darvas, F. et al., "Investigation of the common mechanism of action of antibacterial compounds containing gamma–pyridone–beta–carboxylic acid structure by principal component", Retrieved from STN Database accession No. 93:1350, XP002182132, abstract, Arzneim. –Forsch. (1979), 22(9), 1334–9.

Patel et al., "Directed aminomethylation of 3–Hydroxy–2(1Hpyridinones and –3hydroxy–4(1H)–pyridinones: Synthesis of iso–deferiprone." Tetrahedron, Elsevier Science Publishers, Amsterdam, NL, vol. 52, No. 5, 1996, XP004104485.

Trecourt, et al., "First synthesis of (+/−) harizianopyridone by metalation of polysubstituted O–pyridylcarbamates." Retrieved from STN Database accession No. 123:256397, XP002182410 abstract, J. Heterocycl. Chem (1995), 32(4), 1117–4.

Novelty Search Report of P0201996 dated Nov. 28, 2002.

Coburn, C.A., "Small–molecule direct thrombine inhibitors 1997–2000." Expert Opinions on Therapeutic Patents, 2001, 721–738, vol. 11, No. 5.

XP–002172033—Kohama et al., "Preparation of Piperidinyloxyacetylaminobenzoylalanine Derivatives and Analogs as Antithrombotics." JP 07,233,148.

XP–002187583—Moerner, Hoppe–Seyler's Z. Physiol. Chem., 69, 1910; 357.

Tulinsky et al., "Novel Asymmetric Synthesis of Atropisomeric 6–Aryl Pyrazinones via an Unusual Chirality Transfer Process." J. Org. Chem., 1999, pp. 93–100, vol. 64, No. 1.

* cited by examiner

SUBSTITITUTED POLYCYCLIC ARYL AND HETEROARYL PYRIDONES USEFUL FOR SELECTIVE INHIBITION OF THE COAGULATION CASCADE

This is a continuation-in-part of U.S. patent application Ser. No. 09/574,740, filed May 18, 2000, which claims priority from U.S. Provisional Patent Application Ser. No. 60/134,811, filed May 19, 1999.

FIELD OF THE INVENTION

This invention is in the field of anticoagulant therapy, and specifically relates to compounds, compositions and methods for preventing and treating thrombotic conditions such as coronary artery and cerebrovascular disease.

More particularly, the invention relates to substituted polycyclic aryl and heteroaryl pyridone compounds that inhibit serine proteases of the coagulation cascade.

BACKGROUND OF THE INVENTION

Physiological systems control the fluidity of blood in mammals [Majerus, P. W. et al: Anticoagulant, Thrombolytic, and Antiplplatelet Drugs. In Hardman, J. G. and Limbird, L. E., editors: Goodman & Gilman's The Pharmacological Basis of Therapeutics. 9th edition. New York, McGraw-Hill Book Co., 1996, pp. 1341–1343]. Blood must remain fluid within the vascular systems and yet be able to undergo hemostasis, cessation of blood loss from a damaged vessel, quickly. Hemostasis or clotting begins when platelets first adhere to macromolecules in subendothelian regions of an injured and/or damaged vessels. These platelets aggregate to form the primary hemostatic plug and stimulate local activation of plasma coagulation factors leading to generation of a fibrin clot that reinforces the aggregated platelets.

Plasma coagulation factors include factors II, V, VII, VIII, IX, X, XI, and XII; these are also called protease zymogens. These coagulation factors or protease zymogens are activated by serine proteases leading to coagulation in a so called "coagulation cascade" or chain reaction [Handin, R. I.: Bleeding and Thrombosis. In Wilson, J., et al. editors: Harrison's Principles of Internal Medicine. 12th Edition, New York, McGraw-Hill Book Co., 1991,p350]. Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. The presence of Tissue Factor and VIIa accelerates formation of Xa in the presence of calcium ion and phospholipids. Formation of Xa leads to thrombin, fibrin, and a fibrin clot as described above. The presence of one or more of these many different coagulation factors and two distinct pathways of clotting could enable the efficacious, selective control and better understanding of parts of the coagulation or clotting process.

While clotting as a result of an injury to a blood vessel is a critical physiological process for mammals such as man, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus all formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

There have been several reports of non-peptidic and peptidic pyridone compounds that act as an inhibitor of a coagulation factor present in the coagulation cascade or clotting process. In PCT Patent Application WO 98/47876, Van Boeckel et al. describe peptidic 6-alkylpyridones and 2-alkylpyrimidinones as anti-thrombotic compounds. In PCT Patent Application WO 98/16547, Zhu and Scarborough describe 3-N-heterocyclylamino)-4,5,6-substituted-pyridonylacetamides and 2,4-substituted-5-(N-heterocyclylamino)pyrimidinonyl-acetamides containing amide substituents and having activity against mammalian factor Xa In U.S. Pat. No. 5,656,645, Tamura et al. describe 4,5,6-substituted-3-aminopyridonyl-acetamides, 1,6-substituted-5-aminouracinylacetamides, and 2,4-substituted-5-aminopyrimidinonylacetamides containing amide substituents having a formyl function and having activity against thrombin. In U.S. Pat. No. 5,658,930, Tamura et al. again describe 4,5,6-substituted-3-aminopyridonyl-acetamides, 1,6-substituted-5-aminouracinylacetamides, and 2,4-substituted-5-aminopyrimidinonylacetamides containing amide substituents having a formyl function and having activity against thrombin. In PCT Patent Applications 96/18644 and 97/46207, Tamura et al. further describe 4,5,6-substituted-3-aminopyridonylacetamides, 1,6-substituted-5-aminouracinyl-acetamides, and 2,4-substituted-5-aminopyrimidinonylacetamides containing amide substituents having a formyl function and having activity against thrombin. In PCT Patent Application WO 98/09949, Suzuki et al. describe 2-heterocyclylacetamido derivatives of 1,2-diketones and report that they inhibit proteases, especially chymase inhibitors. In U.S. Pat. No. 5,668,289, Sanderson et al. describe 6-alkyl, 6-cycloalkyl, and 6-trifluoromethyl pyridones unsubstituted at the 4 and 5 positions and reported to inhibit thrombin. In PCT Patent Application WO 97/01338, Sanderson et al. describe 6-alkyl, 6-cycloalkyl, and 6-trifluoromethyl pyridones unsubstituted at the 4 and 5 positions and reported to inhibit thrombin. In U.S. Pat. No. 5,792,779,Sanderson et al. describe substituted 4,6-alkyl, 4,6-cycloalkyl, and 4,6-trifluoromethyl pyridones having utility as thrombin inhibitors. In PCT Patent Application WO 97/30708, Sanderson et al. describe additional substituted 4,6-alkyl, 4,6-cycloalkyl, and 4,6-trifluoromethyl pyridones having utility as thrombin inhibitors. In U.S. Pat. No. 5,869,487, Coburn et al. describe pyrido[3,4-B]pyrazines containing a fused 6-methylpyridone functionality and having utility as thrombin inhibitors. In PCT Patent Application WO 98/31670, Sanderson et al. describe additional 4-substituted 6-alkyl, 6-cycloalkyl, and 6-trifluoromethyl pyridones having utility as thrombin inhibitors. In PCT Patent Application WO 98/17274, Coburn et al. disclose substituted 3,4-diaminomethylpyridones having utility as human thrombin inhibitors. In PCT Patent Application WO 98/42342, Isaacs et al. describe additional 6-alkyl, cycloalkyl, and trifluoromethyl substituted pyridones and pyrazinones reported to inhibit human thrombin.

SUMMARY OF THE INVENTION

It is an object of the present invention to provide compounds that are beneficial in anticoagulant therapy and that have a general structure:

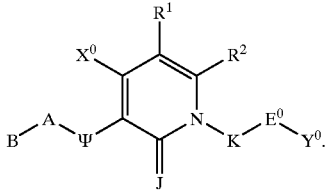

Formula (I)

It is another object of the present invention to provide methods for preventing and treating thrombotic conditions, such as coronary artery disease, cerebrovascular disease, and other coagulation related disorders. Such thrombotic conditions are prevented and treated by administering to a patient in need thereof an effective amount of compounds of Formula (I).

Various other objects and advantages of the present invention will become apparent from the following description of the invention.

DESCRIPTION OF THE INVENTION

The present invention relates to a class of compounds comprising Substituted Polycyclic Aryl and Heteroaryl Pyridones, which are beneficial in anticoagulant therapy for the treatment and prevention of a variety of thrombotic conditions including coronary artery and cerebrovascular disease, as given in Formula (I):

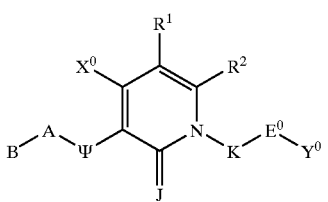

(I)

or a pharmaceutically acceptable salt thereof, wherein;

J is selected from the group consisting of O and S;

J is optionally selected from the group consisting of CH—$R^6$ and N—$R^6$ wherein $R^6$ is a linear spacer moiety having a chain length of 1 to 4 atoms linked to the point of bonding of a substituent selected from the croup consisting of $R^{4a}$, $R^{4b}$, $R^{39}$, $R^{40}$, $R^5$, $R^{14}$, and $R^{15}$ to form a heterocyclyl ring having 5 through 8 members;

B is formula (V):

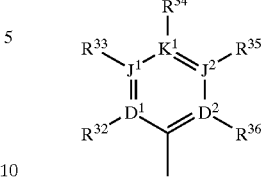

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J_1$, $J^2$ and $K^1$ is S, one of $D^{b1}$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxyalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, heteroarylalkyl, arylalkenyl, heteroarylalkenyl, carboxyalkyl, carboalkoxy, alkoxycarboxamido, alkylamidocabonylamido, arylamidocarbonylamido, carboalkoxyalkyl, carboalkoxyalkenyl, carboxy, carboaralkoxy, carboxamido, carboxaridoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{35}$ and $R^{36}$ are independently optionally $Q^b$;

$R^{32}$, $R^{33}$, $R^{33}$ and $R^{34}$, $R^{34}$ and $R^{35}$, and $R^{36}$ are independently optionally selected to form a spacer pair wherein a spacer pair is taken together to form a linear moiety having from 3 through 6 atoms connecting the points of bonding of said spacer pair members to form a ring selected from the group consisting of a cycloalkenyl ring having 5 through 8 members, a partially saturated heterocyclyl ring having 5 through 8 members, a heteroaryl ring having 5 through 6 members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ can be used at the same time;

$R^9$ and $R^{10}$, $R^{10}$ and $R^{11}$, $R^{11}$ and $R^{12}$, and $R^{12}$ and $R^{13}$ are independently optionally selected to form a spacer pair wherein a spacer pair is taken together to form a linear moiety having from 3 through 6 atoms connecting the points of bonding of said spacer pair members to form a ring selected from the group consisting of a cycloalkenyl ring having 5 through 8 members, a partially saturated heterocyclyl ring having 5 through 8 members, a heteroaryl ring having 5 through 6 members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ can be used at the same time;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, P(O)($R^8$), N($R^7$)P(O)($R^8$), P(O)($R^8$)N($R^7$), C(N$R^7$)N($R^7$), ($R^7$)NC(N$R^7$), ($R^7$)NC(N$R^7$)N$R^7$, and N($R^7$) with the proviso that no more than one of the group consisting of rr and pa can be 0 at the same time;

$R^7$ and $R^8$ are independently selected from the group consisting of hydrido, hydroxy, alkyl, acyl, aroyl, heteroaroyl, and alkoxyalkyl;

$R^{14}$, $R^{15}$, $R^{37}$, and $R^{38}$ are independently selected from the group consisting of hydrido, hydroxy, halo, cyano, hydroxyalkyl, alkoxy, alkyl, alkoxyalkyl, cycloalkyl, cycloalkylalkyl, cycloalkenyl, cycloalkenylalkyl, haloalkyl, haloalkenyl, haloalkoxy, haloalkoxyalkyl, haloalkenyloxyalkyl, halocycloalkoxy, halocycloalkoxyalkyl, halocycloalkenyloxyalkyl, carboxy, carboxyalkyl, carboalkoxy, carboxamido, and carboxamidoalkyl, wherein $R^{38}$ is optionally substituted at from one through three of the ring carbons with a substituent selected from the group consisting of $R^{16}$, $R^{17}$, $R^{18}$, and $R^{19}$;

$R^{14}$ and $R^{38}$ can be independently selected from the group consisting of acyl, aroyl, and heteroaroyl with the proviso that acyl is selected from other than formyl and 2-oxoacyl and $R^{38}$ is optionally substituted at from one through three of the ring carbons with a substituent selected from the group consisting of $R^{16}$, $R^{17}$, $R^{18}$, and $R^{19}$;

Ψ is selected from the group consisting of N$R^5$, O, C(O), C(S), S, S(O), S(O)$_2$, ON($R^5$), P(O)($R^8$), and C$R^{39}R^{40}$;

$R^5$ is selected from the group consisting of hydrido, hydroxy, amino, alkyl, alkoxy, alkoxyalkyl, haloalkyl, acyl, aroyl, and heteroaroyl;

$R^{39}$ and $R^{40}$ are independently selected from the group consisting of hydrido, hydroxy, halo, cyano, hydroxyalkyl, acyl, aroyl, heteroaroyl, acylamido, alkoxy, alkyl, alkoxyalkyl, haloalkyl, haloalkoxy, haloalkoxyalkyl, alkylsulfonyl, haloalkylsulfonyl, carboxy, carboxyalkyl, carboalkoxy, carboxamido, and carboxamidoalkyl;

$R^1$, $R^2$ and $X^0$ are independently selected from the group consisting of $Z^0$—Q, hydrido, alkyl, alkenyl, and halo;

$R^1$ and $X^0$ are independently optionally selected from the group consisting of amino, aminoalkyl, alkylamino, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$X^0$ and $R^1$ or $R^1$ and $R^2$ is optionally —W=X—Y=Z— wherein —W=X—Y=Z— forms an aryl or C5–C6 heteroaryl;

W, X, Y and Z are independently selected from the group consisting of C($R^9$), C($R^{10}$), C($R^{11}$), C($R^{12}$), N, N($R^{10}$), O, S, and a covalent bond with the provisos that one of W, X, Y, and Z is independently selected to be a covalent bond when one of W, X, Y, and Z is O or S, no more than one of W, X, Y, and Z is optionally O or S, and no more than three of W, X, Y, and Z are optionally N or N($R^{10}$);

$X^0$ and $R^1$ or $R^1$ and $R^2$ is optionally bonded together to form C5–C8 cycloalkenyl ring or a partially saturated C5–C8 heterocyclyl ring, wherein said ring is optionally substituted with one or more of the group consisting of $R^9$, $R^{10}$, $R^{11}$, $R^{12}$, and $R^{13}$;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$, Se, Se(O), Se(O)$_2$, Se(O)$_2$N($R^{41}$), N($R^{41}$)Se(O)$_2$, P(O)($R^8$), N($R^7$)P(O)($R^8$), P(O)($R^8$)N($R^7$), N($R^{41}$), ON($R^{41}$), and Si$R^{28}R^{29}$, and (CH($R^{41}$))$_e$—$W^{22}$—(CH($R^{42}$))$_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{41}$ and $R^{42}$ are selected from other than halo and cyano when directly bonded to N, $Z^0$ is directly bonded to the pyridone ring, and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of amidino, hydroxyamino, hydrido, hydroxy, amino, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroaralkyl, heteroarylthioalkyl, heteroaralkylthioalkyl, alkylsulfonyl, haloalkylsulfonyl, arylsulfonyl, arylsulfonylalkyl, aralkylsulfonyl, cycloalkylsulfonyl, cycloalkylsufonylalkyl, heteroarylsulfonylalkyl, heteroarylsulfonyl, and aralkylsulfonylalkyl;

Q is formula (II):

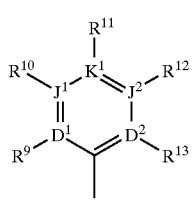

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen and that $D^1$, $D^2$, $J^1$, $J^2$ and $K^1$ are selected to maintain an aromatic ring system;

Q is optionally selected from formula (III):

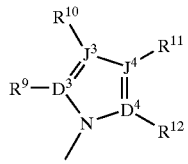

(III)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N, with the provisos that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen and that $D^3$, $D^4$, $J^3$, and $J^4$ are selected to maintain an aromatic ring system;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a single covalent bond when Q is hydrido;

K is $(CR^{4a}R^{4b})_n$ wherein n is an integer selected from 1 through 2;

$R^{4a}$ and $R^{4b}$ are independently selected from the group consisting of halo, hydrido, hydroxy, cyano, hydroxyalkyl, alkyl, alkenyl, alkoxyalkyl, aralkyl, heteroaralkyl, alkylthioalkyl, haloalkyl, haloalkenyl, and cyanoalkyl;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, P(O)($R^8$), N($R^7$)P(O)($R^8$), P(O)($R^8$)N($R^7$), N($R^7$), ON($R^7$), $CR^{4a}$=$CR^{4b}$, ethynylidene (C≡C; 1,2-ethynyl), and C=$CR^{4a}R^{4b}$;

K is optionally $(CH(R^{14}))_j$—T wherein j is selected from a integer from 0 through 2 and T is selected from the group consisting of single covalent bond, O, S, and -N($R^7$) with the proviso that $(CH(R^{14}))_j$ is bonded to the pyridone ring;

$E^0$ is optionally $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N($R^7$), ($R^7$)NC(O), C(S)N($R^7$), ($R^7$)NC(S), ($R^7$)NC(O)O, ($R^7$)NC(S)S, ($R^7$)NC(O)S, ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N(H)C(O), C(O)N(H)S(O)$_2$, P(O)($R^8$), N($R^7$)P(O)($R^8$), P(O)($R^8$)N($R^7$), and N($R^7$);

K is optionally G—$(CH(R^{15}))_k$ wherein k is selected from an integer from 1 through 2 and G is selected from the group consisting of O, S, and N($R^7$) with the proviso that $R^{15}$ is other than hydroxy, cyano, halo, amino, alkylamino, dialkylamino, and sulfhydryl when k is 1;

$E^O$ is optionally $E^3$ when K is G—(CH($R^{15}$))$_k$, wherein $E^3$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N ($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, P(O)($R^8$), N($R^7$)P (O)($R^8$), P(O)($R^8$)N($R^7$), N($R^7$), ON($R^7$), $CR^{4a}$=$CR^{4b}$, ethynylidene (C≡C; 1,2-ethynyl), and C=$CR^{4a}R^{4b}$;

$Y^O$ is formula (IV):

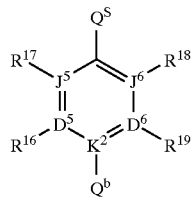

(IV)

wherein $D^5$, $D^6$, $J^5$, and $J^6$ are independently selected from the group consisting of C, N, O, S and a covalent bond with the provisos that no more than one is a covalent bond, $K^2$ is independently selected from the group consisting of C and $N^+$, no more than one of $D^5$, $D^6$, $J^5$, and $J^6$ is O, no more than one of $D^5$, $D^6$, $J^5$, and $J^6$ is S, one of $D^5$, $D^6$, $J^5$ and $J^6$ must be a covalent bond when two of $D^5$, $D^6$, $J^5$, and $J^6$ are O and S, no more than three of $D^5$, $D^6$, $J^5$, and $J^6$ is N when $K^2$ is $N^+$, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$R^{16}$ and $R^{17}$ are optionally independently taken together to form a linear moiety spacer having from 3 through 6 atoms connected to form a ring selected from the group consisting of a cycloalkenyl ring having from 5 through 8 members, a partially saturated heterocyclyl ring having from 5 through 8 members, a heteroaryl having from 5 through 6 members, and an aryl;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, $^+NR^{20}R^{21}R^{22}$, oxy, alkyl, alkylamino, dialkylamino, dialkylsulfoniumalkyl, acylamino and hydrido, wherein and $R^{20}$, $R^{21}$, and $R^{22}$ are independently selected from the group consisting of hydrido, amino, alkyl, hydroxy, alkoxy, alkylamino, dialkylamino, and hydroxyalkyl with the provisos that no more than one of $R^{20}$, $R^{21}$, and $R^{22}$ is hydroxy, alkoxy, alkylamino, amino, and dialkylamino at the same time and that $R^{20}$, $R^{21}$, and $R^{22}$ must be other than be hydroxy, alkoxy, alkylamino, amino, and dialkylamino when $K^2$ is $N^+$;

$R^{20}$ and $R^{21}$, $R^{20}$ and $R^{22}$, and $R^{21}$ and $R^{22}$ are independently optionally selected to form a spacer pair wherein a spacer pair is taken together to form a linear moiety having from 4 through 7 atoms connecting the points of bonding of said spacer pair members to form a heterocyclyl ring having 5 through 8 members with the proviso that no more than one of the group consisting of spacer pairs $R^{20}$ and $R^{21}$, $R^{20}$ and $R^{22}$, and $R^{21}$ and $R^{22}$ is used at the same time;

$Q^b$ is optionally selected from the group consisting of $N(R^{26})SO_2N(R^{23})(R^{24})$, $N(R^{26})C(O)OR^5$, $N(R^{26})C(O)SR^5$, $N(R^{26})C(S)OR^5$ and $N(R^{26})C(S)SR^5$ with the proviso that no more than one of $R^{23}$, $R^{24}$, and $R^{26}$ is hydroxy, alkoxy, alkylamino, amino, and dialkylamino when two of the group consisting of $R^{23}$, $R^{24}$, and $R^{26}$ are bonded to the same atom;

$Q^b$ is optionally selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})N(R^{23})(R^{24})$, $N(R^{26})N(R^{26})C(NR^{25})N(R^{23})(R^{24})$, $ON(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, aminoalkyl, alkylamino, dialkylamino, amino, and hydroxyalkyl;

$R^{23}$ and $R^{24}$ are optionally taken together to form a linear spacer moiety having from 4 through 7 atoms connecting the points of bonding to form a heterocyclyl ring having 5 through 8 members;

$Q^S$ is selected from the group consisting of a single covalent bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N ($R^{14}$), ($R^{14}$)NC(O), C(S)N($R^{14}$), ($R^{14}$)NC(S), OC(O)N ($R^{14}$), SC(S)N($R^{14}$), SC(O)N($R^{14}$), OC(S)N($R^{14}$), N($R^{15}$)C (O)N($R^{14}$), ($R^{14}$)NC(O)N($R^{15}$), N($R^{15}$)C(S)N($R^{14}$), ($R^{14}$) NC(S)N($R^{15}$), S(O), S(O)$_2$, S(O)$_2$N($R^{14}$), N($R^{14}$)S(O)$_2$, P(O)($R^8$), N($R^7$)P(O)($R^8$), P(O)($R^8$)N($R^7$), N($R^{14}$), ON($R^{14}$), $(CH(R^{14}))_c$—$W^1$—$(CH(R^{15}))_d$ wherein c and d are integers independently selected from 1 through 4, and $W^1$ is selected from the group consisting of O, S, C(O), C(S), C(O)O, C(S)O, C(O)S, C(S)S, C(O)N($R^{14}$), ($R^{14}$)NC (O), C(S)N($R^{14}$), ($R^{14}$)NC(S), OC(O)N($R^{14}$), ($R^{14}$)NC(O) O, SC(S)N($R^{14}$), ($R^{14}$)NC(S)S, SC(O)N($R^{14}$), ($R^{14}$)NC(O) S, OC(S)N($R^{14}$), ($R^{14}$)NC(S)O, N($R^{15}$)C(O)N($R^{14}$), ($R^{14}$) NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P (O)($R^8$), P(O)($R^8$)N($R^7$), N($R^{14}$), ON($R^{14}$), and $(CH(R^{14}))_e$—$W^{22}$—$(CH(R^{15}))_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,4-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ and are bonded to $E^O$;

$Y^O$ is optionally $Y^{AT}$ wherein $Y^{AT}$ is $Q^b$—$Q^s$;

$Y^O$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—$(CH(R^{15}))_d$ wherein c and d are integers independently selected from 1 through 4, and $W^1$ is selected from the group consisting of O, S, C(O), C(S), C(O)O, C(S)O, C(O)S, C(S)S, C(O)N($R^{14}$), ($R^{14}$)NC (O), C(S)N($R^{14}$), ($R^{14}$)NC(S), OC(O)N($R^{14}$), ($R^{14}$)NC(O) O, SC(S)N($R^{14}$), ($R^{14}$)NC(S)S, SC(O)N($R^{14}$), ($R^{14}$)NC(O) S, OC(S)N($R^{14}$), ($R^{14}$)NC(S)O, N($R^{15}$)C(O)N($R^{14}$), ($R^{14}$) NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P (O)($R^8$), P(O)($R^8$)N($R^7$), N($R^{14}$), ON($R^{14}$), and $(CH(R^{14}))_e$—$W^2$—$(CH(R^{15}))_h$ wherein e and h are integers independently selected from 0 through 2 and is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N and that $(CR^{37}R^{38})_p$, $(CH(R^{14}))_c$, and $(CH(R^{14}))_e$ are bonded to $E^0$;

$Y^0$ is optionally $Q^b$—$Q^{sss}$ wherein $Q^{sss}$ is $(CH(R^{38}))_r$—$W^3$, r is an integer selected from 1 through 3, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 3, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,7-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,5-isoquinolinyl, 3,4-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7- benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In another embodiment of compounds of Formula I or a pharmaceutically acceptable salt thereof, J is selected from the group consisting of O and S;

B is formula (V):

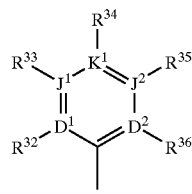

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, arakylamino, arylthio, arylthioalkyl, heteroaralkoxyalkyl, alkylsulfinyl, alkylsulfinylalkyl, arylsulfinylalkyl, arylsulfonylalkyl, heterarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl, C5–C10 cycloalkenyl, and C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

A is selected from the group consisting of single covalent bond, $(W^7)_{rr}$—$CH(R^{15})_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(O)N(R⁷), C(S)N(R⁷), (R⁷)NC(O), (R⁷)NC(S), and N(R⁷) with the proviso that no more than one of the group consisting of rr and pa can be 0 at the same time;

R⁷ and R⁸ are independently selected from the group consisting of hydrido, hydroxy, alkyl, and alkoxyalkyl;

R¹⁴, R¹⁵, R³⁷, and R³⁸ are independently selected from the group consisting of hydrido, hydroxy, halo, alkyl, alkoxyalkyl, haloalkyl, haloalkoxy, and haloalkoxyalkyl;

R¹⁴ and R³⁸ can be independently selected from the group consisting of aroyl and heteroaroyl, wherein R³⁸ is optionally substituted at from one through three of the ring carbons with a substituent selected from the group consisting of R¹⁶, R¹⁷, R¹⁸, and R¹⁹;

Ψ is selected from the group consisting of NR⁵, C(O), and S(O)₂;

R⁵ is selected from the group consisting of hydrido, hydroxy, alkyl, and alkoxy;

R³⁹ and R⁴⁰ are independently selected from the group consisting of hydrido, hydroxy, halo, hydroxyalkyl, alkyl, alkoxyalkyl, haloalkyl, haloalkoxy, and haloalkoxyalkyl;

R¹ and X⁰ are independently selected from the group consisting of hydrido, alkyl, alkenyl, cyano, halo, haloalkyl, haloalkoxy, haloalkylthio, amino, aminoalkyl, alkylamino, amidino, guanidino, hydroxy, hydroxyamino, alkoxy, hydroxyalkyl, alkoxyamino, thiol, alkylthio, and phosphono;

X⁰ and R¹ or R¹ and R² is optionally —W=X—Y=Z— wherein —W=X—Y=Z— forms an aryl or C5–C6 heteroaryl;

W, X, Y, and Z are independently selected from the group consisting of C(R⁹), C(R¹⁰), C(R¹¹), C(R¹²), N, N(R¹⁰), O, S, and a covalent bond with the provisos that one of W, X, Y, and Z is independently selected to be a covalent bond when one of W, X, Y, and Z is O or S, no more than one of W, X, Y, and Z is optionally O or S, and no more than three of W, X, Y, and Z are optionally N or N(R¹⁰);

X⁰ and R¹ or R¹ and R² is optionally bonded together to form C5–C8 cycloalkenyl ring or a partially saturated C5–C8 heterocyclyl ring, wherein said ring is optionally substituted with one or more of the group consisting of R⁹, R¹⁰, R¹¹, R¹², and R¹³;

R² is Z⁰—Q;

Z⁰ is selected from the group consisting of covalent single bond, (CR⁴¹R⁴²)_q wherein q is an integer selected from 1 through 3, (CH(R⁴¹))_g—W⁰—CH(R⁴²))_p wherein g and p are integers independently selected from 0 through 3 and W⁰ is selected from the group consisting of O, S, C(O), S(O), S(O)₂, N(R⁴¹), and ON(R⁴¹), and (CH(R⁴¹))_e—W²²—(CH(R⁴²))_h wherein e and h are integers independently selected from 0 through 2 and W²² is selected from the group consisting of CR⁴¹=CR⁴², 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that Z⁰ is directly bonded to the pyridone ring and W²² is optionally substituted with one or more substituents selected from the group consisting of R⁹, R¹⁰, R¹¹, R¹², and R¹³;

R⁴¹ and R⁴² are independently selected from the group consisting of amidino, hydroxyamino, hydrido, hydroxy, amino, and alkyl;

Q is selected from the group consisting of hydrido, with the proviso that Z⁰ is other than covalent single bond, the formula (II):

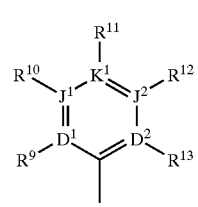

(II)

wherein

D¹, D², J¹, J² and K¹ are independently selected from the group consisting of C, N, O, S and a covalent bond with the provisos that no more than one is a covalent bond, no more than one of D¹, D², J¹, J² and K¹ is O, no more than one of D¹, D², J¹, J² and K¹ is S, one of D¹, D², J¹, J² and K¹ must be a covalent bond when two of D¹, D², J¹, J² and K¹ are O and S, and no more than four of D¹, D², J¹, J² and K¹ is N, with the provisos that D¹, D², J¹, J² and K¹ are selected to maintain an aromatic ring system and that R⁹, R¹⁰, R¹¹, R¹², and R¹³ are each independently selected to maintain the tetravalent nature of carbon, trivalent nature of nitrogen, the divalent nature of sulfur, and the divalent nature of oxygen;

K is (CR⁴ᵃR⁴ᵇ)_n wherein n is 1 or 2;

R⁴ᵃ and R⁴ᵇ are independently selected from the group consisting of halo, hydrido, hydroxyalkyl, alkyl, alkoxyalkyl, alkylthioalkyl, and haloalkyl;

E⁰ is selected from the group consisting of a covalent single bond, C(O), C(S), C(O)N(R⁷), (R⁷)NC(O), S(O)₂, (R⁷)NS(O)₂, and S(O)₂N(R⁷);

Y⁰ is formula (IV):

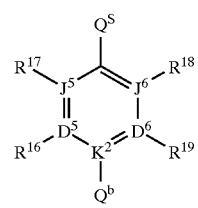

(IV)

wherein

D⁵, D⁶, J⁵, and J⁶ are independently selected from the group consisting of C, N, O, S and a covalent bond with the provisos that no more than one is a covalent bond, K is C, no more than one of D⁵, D⁶, J⁵, and J⁶ is O, no more than one of D⁵, D⁶, and J⁵, and J⁶ is S, one of D⁵, D⁶, J⁵, and J⁶ must be a covalent bond when two of D⁵, D⁶, J⁵, and J⁶ are O and S, and no more than four of D⁵, D⁶, J⁵, and J⁶ are N when K² is carbon, with the provisos that R¹⁶, R¹⁷, R¹⁸, and R¹⁹ are each independently selected to maintain the tetravalent nature of carbon, trivalent nature of nitrogen, the divalent nature of sulfur, and the divalent nature of oxygen and that D⁵, D⁶, J⁵, and J⁶ are selected to maintain an aromatic ring system;

Qᵇ is selected from the group consisting of NR²⁰R²¹, ⁺NR²⁰R²¹R²², and hydrido, wherein R²⁰, R²¹, and R²² are independently selected from the group consisting of hydrido, alkyl, hydroxy, amino, dialkylamino, alkylamino, and hydroxyalkyl with the proviso that no more than one of R²⁰ and R²¹ is selected from the group consisting of hydroxy, amino, alkylamino, and dialkylamino at the same time;

Qᵇ is optionally selected from the group consisting of C(NR²⁵)NR²³R²⁴, N(R²⁶)C(NR²⁵)N(R²³)(R²⁴), C(O)N ($R^{26}$)C(N$R^{25}$)N($R^{23}$)($R^{24}$), N($R^{26}$)N($R^{26}$)C(N$R^{25}$)N($R^{23}$)($R^{24}$), and ON($R^{26}$)C(N$R^{25}$)N($R^{23}$)($R^{24}$) with the provisos that no more than one of $R^{23}$, $R^{24}$, and $R^{26}$ is selected from the group consisting of hydroxy, amino, alkylamino, and dialkylamino when two of the group consisting of $R^{23}$, $R^{24}$, and $R^{26}$ are bonded to the same atom;

$R^{23}$, $R^{24}$, $R^{25}$, and $R^{26}$ are independently selected from the group consisting of hydrido, alkyl, hydroxy, amino, aminoalkyl, dialkylamino, alkylamino, and hydroxyalkyl;

$Q^s$ is selected from the group consisting of a single covalent bond, $(CR^{37}R^{38})_b$—$(W^0)_{az}$ wherein az is an integer selected from 0 through 1, b is an integer selected from 1 through 5, and $W^0$ is selected from the group consisting of O, C(O), S(O), S(O)$_2$, S(O)$_2$N($R^{14}$), N($R^{14}$)S(O)$_2$, and N($R^{14}$), (CH($R^{14}$))$_c$—$W^1$—(CH($R^{15}$))$_d$ wherein c and d are integers independently selected from 1 through 4 and $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P(O)($R^8$), P(O)($R^8$)N($R^7$), N($R^{14}$), ON($R^{14}$), and (CH($R^{14}$))$_e$—$W^{22}$—(CH($R^{15}$))$_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, (CH($R^{14}$))$_c$, and (CH($R^{14}$))$_e$ are bonded to $E^0$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is selected from the group consisting of $(CR^{37}R^{38})_f$ wherein f is an integer selected from 1 through 4, (CH($R^{14}$))$_c$—$W^1$—(CH($R^{15}$))$_d$ wherein c and d are integers independently selected from 1 through 2, and $W^1$ is selected from the group consisting of $W^1$ is selected from the group consisting of O, S, C(O), C(O)N($R^{14}$), ($R^{14}$)NC(O), N($R^{15}$)C(O)N($R^{14}$), ($R^{14}$)NC(O)N($R^{15}$), N($R^{14}$), ON($R^{14}$), and (CH($R^{14}$))$_e$—$W^2$—(CH($R^{15}$))$_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo when directly bonded to N and that $(CR^{37}R^{38})_f$, (CH($R^{14}$))$_c$, and (CH($R^{14}$))$_e$ are bonded to $E^0$;

$Y^0$ is optionally $Q^b$—$Q^{sss}$ wherein $Q^{sss}$ is (CH($R^{38}$))$_r$—$W^3$, r is an integer selected from 1 through 2, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that (CH($R^{38}$))$_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is (CH($R^{38}$))$_r$—$W^4$, r is an integer selected from 1 through 2, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,3-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^4$ other than the points of attachment is optionally substituted with one or more of the group consisting of $R^9$, $R^{10}$, $R^{11}$, and $R^{12}$, with the provisos that (CH($R^{38}$))$_r$ is bonded to $E^0$ and $Q^b$ is bonded to highest number substituent position of each $W^4$;

$Y^0$ is optionally $Q^b$—$Q^{ssss}$ wherein $Q^{ssss}$ is (CH($R^{38}$))$_r$—$W^5$, r is an integer selected from 1 through 2, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,4-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6- benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 2, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In a preferred embodiment of compounds of Formula I or a pharmaceutically acceptable salt thereof, J is O;

B is the Formula:

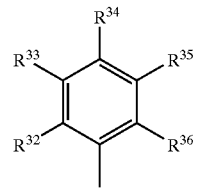

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, alkoxyalkyl, haloalkoxylalkyl, hydroxy, amino, alkoxyamino, nitro, alkylamino, alkylthio, alkylthioalkyl, alkylsulfinyl, alkylsulfonyl, alkylsulfonylalkyl, aryl, aralkyl, cycloalkyl, cycloalkylalkyl, alkylsulfonamido, alkylaminosulfonyl, amidosulfonyl, monoalkyl amidosulfonyl, dialkyl amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^9$, $R^{10}$, $R^{11}$, $R^{12}$, and $R^{13}$ are optionally selected from the group consisting of heteroaryl and heterocyclyl with the proviso that $R^9$, $R^{10}$, $R^{11}$, $R^{12}$, and $R^{13}$ are substituents for other than B;

$R^{16}$, $R^{19}$, $R^{32}$, $R^{33}$, $R^{34}$, $R^{35}$, and $R^{36}$ are independently optionally $Q^b$;

B is optionally, with the proviso that $R^1$ and $R^2$ are selected from the group consisting of a spacer pair and —W═X—Y═Z—, Formula (V):

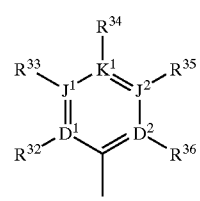

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is selected from the group consisting of C3–C12 cycloalkyl and C4 heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

B is optionally, with the proviso that $R^1$ and $R^2$ are selected from the group consisting of a spacer pair and —W=X—Y=Z—, a C5–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

Ψ is selected from the group consisting of NH and NOH;

$R^1$ and $X^0$ are independently selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$X^0$ and $R^1$ and $R^1$ and $R^2$, with the proviso that no more than one of the group consisting of spacer pair $X^0$ and $R^1$ and spacer pair $R^1$ and $R^2$ is be used at the same time, are optionally selected to be —W=X—Y=Z— wherein —W=X—Y=Z— forms a ring selected from the group consisting of a heteroaryl ring having from 5 through 6 members and an aryl;

W, X, Y, and Z are independently selected from the group consisting of $C(R^9)$, $C(R^{10})$, $C(R^{11})$, $C(R^{12})$, N, $N(R^{10})$, O, S and a covalent bond with the provisos that W, X, Y, and Z can be independently selected to be a covalent bond when one of W, X, Y, and Z is selected from the group consisting of N, $N(R^{10})$, O, and S, no more than one of W, X, Y, and Z can be selected from the group consisting of O and S, and no more than three of W, X, Y, and Z can be selected from the group consisting of N and $N(R^{10})$;

$X^0$ and $R^1$ and $R^1$ and $R^2$ spacer pairs are independently optionally selected to be taken together to form a spacer pair wherein the spacer pair forms a linear moiety having from 3 through 6 atoms connecting the points of bonding of said spacer pair members to form a ring selected from the group consisting of a cycloalkenyl ring having from 5 through 8 members and a partially saturated heterocyclyl ring having from 5 through 8 members, wherein said spacer pair is optionally substituted with one or more of the group consisting of $R^9$, $R^{10}$, $R^{11}$, $R^{12}$, and $R^{13}$ and with the proviso that no more than one of the group consisting of spacer pair $X^0$ and $R^1$ and spacer pair $R^1$ and $R^2$ is present at the same time;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$, and $(CH(R^{41}))_e$—$W^{22}$—$(CH(R^{42}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyridone ring;

$R^{41}$ and $R^{42}$ are independently selected from the group consisting of amidino, hydroxyamino, hydrido, hydroxy, amino, and alkyl;

Q is selected from the group consisting of hydrido, with the proviso that $Z^0$ is other than a covalent single bond, and the formula (II):

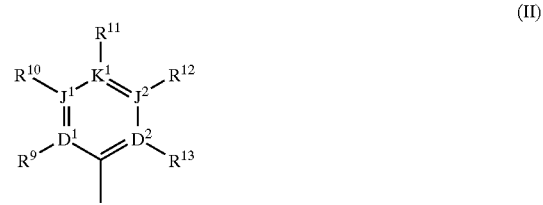

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is an integer selected from 1 through 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is $E^1$, when K is $(CR^{4a}R^{4b})_n$, wherein $E^1$ is selected from the group consisting of a covalent single bond, C(O), C(S), $C(O)N(R^7)$, $(R^7)NC(O)$, $S(O)_2$, $(R^7)NS(O)_2$, and $S(O)_2 N(R^7)$;

$Y^0$ is formula (IV):

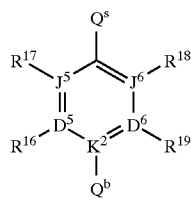

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N with the proviso that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, alkylamino, alkylthio, alkylsulfinyl, alkylsulfonyl, alkanoyl, haloalkanoyl, alkyl, alkenyl, halo, haloalkyl, haloalkoxy, hydroxyalkyl, alkylenylamino, haloalkoxyalkyl, carboalkoxy, and cyano;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, aminoalkyl, dialkylamino, alkylamino, and hydroxyalkyl;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14}))_c$ are bonded to $E^0$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^0$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=$CR^{4b}$ with the proviso that $(CH(R^{14}))_e$ is bonded to $E^0$;

$Y^0$ is optionally selected from the group consisting of $Q^b$—$Q^{ssss}$ and $Q^b$—$Q^{ssssr}$ wherein $Q^{ssss}$ is $(CH(R^{38}))_r$—$W^5$ and $Q^{ssssr}$ is $(CH(R^{38}))_r$—$W^6$, r is an integer selected from 1 through 2, and $W^5$ and $W^6$ are independently selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 3,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ and of the ring of the $W^6$, other than the points of attachment of $W^5$ and $W^6$, is optionally substituted with one or more of the group consisting of $R^9$, $R^{10}$, $R^{11}$, and $R^{12}$, with the provisos that $Q^b$ is bonded to lowest number substituent position of each $W^5$, $Q^b$ is bonded to highest number substituent position of each $W^6$, and $(CH(R^{38}))_r$ is bonded to $E^0$.

In another preferred embodiment of compounds of Formula I or a pharmaceutically acceptable salt thereof, J is O;

B is phenyl or a heteroaryl of 5 or 6 ring members, wherein a nitrogen with a removable hydrogen or a carbon adjacent to the carbon at the point of attachment is optionally substituted by $R^{32}$, a nitrogen with a removable hydrogen or a carbon at the other position adjacent to the point of attachment is optionally substituted by $R^{36}$, a nitrogen with a removable hydrogen or a carbon adjacent to $R^{32}$ and two atoms from the point of attachment is optionally substituted by $R^{33}$, a nitrogen with a removable hydrogen or a carbon adjacent to $R^{36}$ and two atoms from the point of attachment is optionally substituted by $R^{35}$, and a nitrogen with a removable hydrogen or a carbon adjacent to both $R^{33}$ and $R^{35}$ is substituted by $R^{34}$;

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, cycloalkoxy, cycloalkylalkoxy, aralkoxy, aryloxy, heteroaryloxy, heteroaralkoxy, heterocyclyloxy, heterocyclylalkoxy, alkoxyalkyl, haloalkoxyalkyl, hydroxy, amino, alkoxyamino, nitro, alkylamino, N-alkyl-N-arylamino, arylamino, aralkylamino, heteroarylamino, heteroaralkylamino, heterocyclylamino, heterocyclylalkylamino, alkylthio, alkylthioalkyl, alkylsulfinyl, arylsulfinyl, aralkylsulfinyl, cycloalkylsulfinyl, heteroarylsulfinyl, alkylsulfonyl, arylsulfonyl, aralkylsulfonyl, cycloalkylsulfonyl, heteroarylsulfonyl, alkylsulfonylalkyl, aryl, aralkyl, cycloalkyl, cycloalkylalkyl, heteroaryl, heterocyclyl, alkylsulfonamido, amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or a C4–C9 heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbons and nitrogens adjacent to the carbon at the point of attachment may be optionally substituted with $R^9$ or $R^{13}$, a ring carbon or nitrogen adjacent to the $R^9$ position and two atoms from the point of attachment may be substituted with $R^{10}$, a ring carbon or nitrogen adjacent to the $R^{13}$ position and two atoms from the point of attachment may be substituted with $R^{12}$, a ring carbon three atoms from the point of attachment and adjacent to the $R^{10}$ position may be substituted with $R^{11}$, a ring carbon three atoms from the point of attachment and adjacent to the $R^{12}$ position may be substituted with $R^{33}$, and a ring carbon four atoms from the point of attachment and adjacent to the $R^{11}$ and $R^{33}$ positions may be substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is 0 or 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

Ψ is NH or NOH;

$R^1$ and $X^0$ are independently selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$X^0$ and $R^1$ or $R^1$ and $R^2$ is optionally —W=X—Y=Z— wherein —W=X—Y=Z— forms an aryl or C5–C6 heteroaryl;

W, X, Y, and Z are independently selected from the group consisting of $C(R^9)$, $C(R^{10})$, $C(R^{11})$, $C(R^{12})$, N, $N(R^{10})$, O, S, and a covalent bond with the provisos that one of W, X, Y, and Z is independently selected to be a covalent bond when one of W, X, Y, and Z is or S, no more than one of W, X, Y, and Z is optionally O or S, and no more than three of W, X, Y, and Z are optionally N or $N(R^{10})$;

$X^0$ and $R^1$ or $R^1$ and $R^2$ is optionally bonded together to form C5–C8 cycoalkenyl ring or a partially saturated C5–C8 heterocyclyl ring, wherein said ring is optionally substituted with one or more of the group consisting of $R^9$, $R^{10}$, $R^{11}$, $R^{12}$, and $R^{13}$;

$R^2$ is $Z^0$—Q;

$Z^0$ is selected from the group consisting of a covalent single bond, $W^0$—$(CH(R^{42}))_p$ wherein p is an integer selected from 0 through 3 and $W^0$ is selected from the group consisting of O, S, C(O), S(O), $N(R^{41})$, and $ON(R^{41})$, $(CH(R^{41}))_g$—O wherein g is an integer selected from 1 through 3, $(CH(R^{41}))_g$—S wherein g is an integer selected from 1 through 3 with the proviso that $Z^0$ is directly bonded to the pyridone ring;

$Z^0$ is optionally $W^{22}$—$(CH(R^{42}))_h$ wherein h is 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,5-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the pyridone ring and $W^{22}$ is optionally substituted with one or more substituents selected from the group consisting of $R^9$, $R^{10}$, $R^{11}$, $R^{12}$, and $R^{13}$, with the proviso that $W^{22}$ is selected from other than a cycloalkyl when $Y^0$ is selected as a thiazolyl, imidazolyl, or pyridyl and any one of $Q^b$, $R^{16}$ and $R^{19}$ is selected as hydrido, amino, aminoalkyl, hydroxyalkyl, halo, trifluoromethyl, alkyl, or alkoxy;

$R^{41}$ is selected from the group consisting of hydrido, hydroxy, and alkyl;

$R^{42}$ is selected from the group consisting of amidino, hydroxyamino, hydrido, hydroxy, amino, and alkyl;

Q is phenyl or a heteroaryl of 5 or 6 ring members, wherein a nitrogen with a removably hydrogen or a carbon adjacent to the carbon at the point of attachment is optionally substituted by $R^9$, a nitrogen with a removable hydrogen or a carbon at the other position adjacent to the point of attachment is optionally substituted by $R^{13}$, a nitrogen with a removable hydrogen or a carbon adjacent to $R^9$ and two atoms from the point of attachment is optionally substituted by $R^{10}$, a nitrogen with a removable hydrogen or a carbon adjacent to $R^{13}$ and two atoms from the point of attachment is optionally substituted by $R^{12}$, and a nitrogen with a removable hydrogen or a carbon adjacent to both $R^{10}$ and $R^{12}$ is substituted by $R^{11}$, with the proviso that Q is other than phenyl when $Z^0$ is a covalent single bond;

Q is optionally hydrido with the proviso that $Z^0$ is other than a covalent single bond;

K is $(CR^{4a}R^{4b})_n$ wherein n is 1 or 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is $E^1$, when K is $(CR^{4a}R^{4b})_n$, wherein $E^1$ is selected from the group consisting of a covalent single bond, C(O), C(S), $C(O)N(R^7)$, $(R^7)NC(O)$, $S(O)_2$, $(R^7)NS(O)_2$, and $S(O)_2N(R^7)$;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, lower alkylamino, alkylthio, alkylsulfinyl, alkylsulfonyl, alkanoyl, haloalkanoyl, alkyl, alkenyl, halo, haloalkyl, haloalkoxy, hydroxyalkyl, aminoalkyl, haloalkoxyalkyl, carboalkoxy, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, aminoalkyl, hydrido, $N(R^{26})C(NR^{25})N(R^{23})(R^{24})$, and $C(NR^{25})NR^{23}R^{24}$, with the provisos that no more than one of $R^{20}$ and $R^{21}$ is selected from the group consisting of hydroxy, amino, alkylamino, and dialkylamino at the same time and that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, aminoalkyl, amino, dialkylamino, alkylamino, and hydroxyalkyl;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14}))_c$ are bonded to $E^0$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally aroyl or heteroaroyl, wherein $R^{38}$ is optionally substituted at from one through three of the ring carbons with a substituent selected from the group consisting of $R^{16}$, $R^{17}$, $R^{18}$, and $R^{19}$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is $(CH(R^{14}))_e$—$W^2$—$(CH(R^{15})_h$, wherein e and h are independently 1 or 2 and $W^2$ is $CR^{4a}$=$CR^{4b}$ with the proviso that $(CH(R^{14}))_e$ is bonded to $E^0$;

$Y^0$ is optionally selected from the group consisting of $Q^b$—$Q^{ssss}$ and $Q^b$—$Q^{ssssr}$ wherein $Q^{ssss}$ is $(CH(R^{38}))_r$—$W^5$ and $Q^{ssssr}$ is $(CH(R^{38}))_r$—$W^6$, r is 1 or 2, and $W^5$ and $W^6$ are independently selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,5-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,9-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ and of the ring of the $W^6$, other than the points of attachment of $W^5$ and $W^6$, is optionally substituted with one or more of the group consisting of $R^9$, $R^{10}$, $R^{11}$, and $R^{12}$, with the provisos that $W^5$ and $w^6$ are selected from other than 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, and 3,7-benzisoxazolyl, when r is the integer one, $Q^b$ is bonded to lowest number substituent position of each $W^5$, $Q^b$ is bonded to highest number substituent position of each $W^6$, and $(CH(R^{38}))_r$ is bonded to $E^0$.

In a more preferred embodiment of compounds of Formula I or a pharmaceutically acceptable salt thereof, J is O;

B is the Formula:

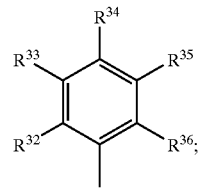

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, alkanoyl, haloalkanoyl, nitro, alkylamino, alkylthio, aryl, aralkyl, cycloalkyl, cycloalkylalkyl, alkylsulfonamido, amidosulfonyl, monoalkyl amidosulfonyl, dialkyl amidosulfonyl, alkyl, alkenyl, halo, haloalkyl, haloalkenyl, haloalkoxy, hydroxyalkyl, alkylenylamino, carboalkoxy, carboxy, carboxamido, cyano, and $Q^b$;

B is optionally, with the proviso that $R^1$ and $R^2$ are selected from the group consisting of a spacer pair and —W=X—Y=Z—, Formula (V):

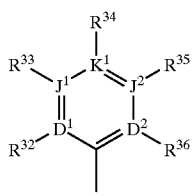
(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is selected from the group consisting of C3–C12 cycloalkyl and C4 heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment are optionally substituted with $R^{12}$, a ring carbon three atoms from the point of attachment and adjacent to the $R^{10}$ position is optionally substituted with $R^{11}$, a ring carbon three atoms from the point of attachment and adjacent to the $R^{12}$, position is optionally substituted with $R^{33}$, and a ring carbon four atoms from the point of attachment and adjacent to the $R^{11}$ and $R^{33}$ positions is optionally substituted with $R^{34}$;

B is optionally, with the proviso that $R^1$ and $R^2$ are selected from the group consisting of a spacer pair and —W=X—Y=Z—, a C5–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, hydroxy, amino, alkylamino, alkylthio, alkylsulfinyl, alkylsulfonyl, alkylsulfonamido, amidosulfonyl, monoalkyl amidosulfonyl, dialkyl amidosulfonyl, alkyl, halo, haloalkyl, haloalkoxy, hydroxyalkyl, aminoalkyl, carboalkoxy, carboxyalkyl, carboxy, carboxamido, and cyano;

$R^9$, $R^{10}$, $R^{11}$, $R^{12}$, and $R^{13}$ are optionally selected from the group consisting of heteroaryl and heterocyclyl with the proviso that $R^9$, $R^{10}$, $R^{11}$, $R^{12}$, and $R^{13}$ are substitutents for other than B;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

$\Psi$ is NH;

$R^1$ and $X^0$ are independently selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^1$ and $R^2$ is optionally selected to be —W=X—Y=Z— wherein —W=X—Y=Z— forms a ring selected from the group consisting of a heteroaryl ring having from 5 through 6 members and an aryl;

W, X, Y, and Z are independently selected from the group consisting of $C(R^9)$, $C(R^{10})$, $C(R^{11})$, $C(R^{12})$, N, $N(R^{10})$, O, S and a covalent bond with the provisos that W, X, Y, and Z can be, independently selected to be a covalent bond when one of W, X, Y, and Z is selected from the group consisting of N, $N(R^{10})$, O, and S, no more than one of W, X, Y, and Z can be selected from the group consisting of O and S, and no more than three of W, X, Y, and Z can be selected from the group consisting of N and $N(R^{10})$;

$R^1$ and $R^2$ spacer pairs are independently optionally selected to be taken together to form a spacer pair wherein the spacer pair forms a linear moiety having from 3 through 6 atoms connecting the points of bonding of said spacer pair members to form a ring selected from the group consisting of a cycloalkenyl ring having from 5 through 8 members and a partially saturated heterocyclyl ring having from 5 through 8 members, wherein said spacer pair is optionally substituted with one or more of the group consisting of $R^9$, $R^{10}$, $R^{11}$, $R^{12}$, and $R^{13}$;

$R^2$ is $Z^0$—Q;

$Z^0$ is selected from the group consisting of covalent single bond and $(CR^{41}R^{42})_q$ wherein q is an integer selected from 1 through 2, $(CH(R^{41}))_g$—$W^0$—$(CH(R^{42}))_p$ wherein g and p are integers independently selected from 0 through 3 and $W^0$ is selected from the group consisting of O, S, and $N(R^{41})$, and $(CH(R^{41}))_e W^{22}$—$(CH(R^{42}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5- pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^o$ is directly bonded to the pyridone ring;

$R^{41}$ and $R^{42}$ are independently selected from the group consisting of hydrido, hydroxy, and amino;

Q is selected from the group consisting of hydrido, with the proviso that $Z^o$ is other than a covalent single bond, aryl, and heteroaryl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CHR^{4a}$ wherein $R^{4a}$ is selected from the group consisting of hydrido, hydroxyalkyl, alkyl, alkoxyalkyl, alkylthioalkyl, and haloalkyl;

$E^o$ is selected from the group consisting of a covalent single bond, C(O)N(H), (H)NC(O), $(R^7)NS(O)_2$, and $S(O)_2N(R^7)$;

$Y^o$ is formula (IV):

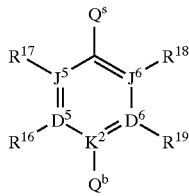

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$ and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14}))_c$ are bonded to $E^o$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^o$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=CH with the proviso that $(CH(R^{14}))_e$ is bonded to $E^o$.

In another more preferred embodiment of compounds of Formula I or a pharmaceutically acceptable salt thereof, J is O;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, lower alkylamino, alkylthio, aryl, aralkyl, cycloalkyl, cycloalkylalkyl, heteroaryl, heterocyclyl, alkylsulfonamido, amidosulfonyl, monoalkyl amidosulfonyl, dialkyl amidosulfonyl, alkyl, alkenyl, halo, haloalkyl, haloalkenyl, haloalkoxy, hydroxyalkyl, hydroxyhaloalkyl, aminoalkyl, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or C4–C9 heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbons and nitrogens adjacent to the carbon at the point of attachment may be optionally substituted with $R^9$ or $R^{13}$, a ring carbon or nitrogen adjacent to the $R^9$ position and two atoms from the point of attachment may be substituted with $R^{10}$, a ring carbon or nitrogen adjacent to the $R^{13}$ position and two atoms from the point of attachment may be substituted with $R^{12}$, a ring carbon three atoms from the point of attachment and adjacent to the $R^{10}$ position may be substituted with $R^{11}$, a ring carbon three atoms from the point of attachment and adjacent to the $R^{12}$ position may be substituted with $R^{33}$, and a ring carbon four atoms from the point of attachment and adjacent to the $R^{11}$ and $R^{33}$ positions may be substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkylamino, N-alkyl-N-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, alkylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is a single covalent bond or $(CH(R^{15}))_{pa}$—$(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

Ψ is NH;

$R^1$ and $X^0$ are independently selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$X^0$ and $R^1$ or $R^1$ and $R^2$ is optionally —W=X—Y=Z— wherein —W=X—Y=Z— forms an aryl or heteroaryl of 5 or 6 ring-members;

W, X, Y, and Z are independently selected from the group consisting of $C(R^9)$, $C(R^{10})$, $C(R^{11})$, $C(R^{12})$, N, $N(R^{10})$, O, S and a covalent bond with the provisos that one of W, X, Y, and Z is independently selected to be a covalent bond when one of W, Y, and Z is O or S, no more than one of W, X, Y, and Z is optionally selected from the group consisting of O and S, and no more than three of W, X, Y, and Z are optionally selected from the group consisting of N and $N(R^{10})$;

$X^0$ and $R^1$ or $R^1$ and $R^2$ is optionally bonded together to form C5–C8 cycloalkenyl ring or a partially saturated C5–C8 heterocyclyl ring, wherein said ring is optionally substituted with one or more of the group consisting of $R^9$, $R^{10}$, $R^{11}$, $R^{12}$, and $R^{13}$;

$R^2$ is $Z^0$—Q;

$Z^0$ is selected from the group consisting of a covalent single bond, $W^0$—$(CH(R^{42}))_p$ wherein p is an integer selected from 0 through 3 and $W^0$ is selected from the group consisting of O, S, and $N(R^{41})$, and $(CH(R^{41}))_g$—O wherein g is an integer selected from 1 through 3, with the proviso that $Z^0$ is directly bonded to the pyridone ring;

$Z^0$ is optionally $W^{22}$—$(CH(R^{42}))_h$ wherein h is 0 or 1 and $W^{22}$ is selected from the group consisting of 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the pyridone ring and $W^{22}$ is optionally substituted with one or more substituents selected from the group consisting of $R^9$, $R^{10}$, $R^{11}$, $R^{12}$, and $R^{13}$, with the proviso that $W^{22}$ is selected from other than a cycloalkyl when $Y^0$ is selected as a thiazolyl, imidazolyl, or pyridyl and any one of $Q^b$, $R^{16}$ and $R^{19}$ is selected as hydrido, amino, aminoalkyl, hydroxyalkyl, halo, trifluoromethyl, alkyl, or alkoxy;

$R^{41}$ is selected from the group consisting of hydrido, hydroxy, and alkyl;

$R^{42}$ is selected from the group consisting of amidino, hydroxyamino, hydrido, hydroxy, amino, and alkyl;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^0$ is a covalent single bond;

Q is optionally hydrido with the proviso that $Z^0$ is selected from other than a covalent single bond;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, lower alkyl amino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$, with the provisos that no more than one of $R^{20}$ and $R^{21}$ is selected from the group consisting of hydroxy, amino, alkylamino, and dialkylamino at the same time and that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of C(O)N(R$^{14}$), (R$^{14}$)NC(O), S(O), S(O)$_2$, S(O)$_2$N(R$^{14}$), N(R$^{14}$)S(O)$_2$, and N(R$^{14}$), with the provisos that R$^{14}$ is selected from other than halo when directly bonded to N and that (CR$^{37}$R$^{38}$)$_b$, and (CH(R$^{14}$))$_c$ are bonded to E$^0$;

R$^{14}$ is selected from the group consisting of hydrido, halo, alkyl, and haloalkyl;

R$^{37}$ and R$^{38}$ are independently selected from the group consisting of hydrido, alkyl, and haloalkyl;

R$^{38}$ is optionally aroyl or heteroaroyl, wherein R$^{38}$ is optionally substituted at from one through three of the ring carbons with a substituent selected from the group consisting of R$^{16}$, R$^{17}$, R$^{18}$, and R$^{19}$;

Y$^0$ is optionally Y$^{AT}$ wherein Y$^{AT}$ is Q$^b$—Q$^s$;

Y$^0$ is optionally Q$^b$—Q$^{ss}$ wherein Q$^{ss}$ is (CH(R$^{14}$))$_e$—W$^2$—(CH(R$^{15}$))$_h$, wherein e and h are independently 1 or 2 and W$^2$ is CR$^{4a}$=CH with the proviso that (CH(R$^{14}$))$_e$ is bonded to E$^0$.

In an even more preferred embodiment of compounds of Formula I or a pharmaceutically acceptable salt thereof, J is O;

B is the Formula:

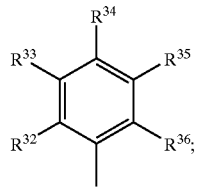

R$^{32}$, R$^{33}$, R$^{34}$, R$^{35}$, and R$^{36}$ are independently selected from the group consisting of hydrido, acetamido, haloacetamido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and Q$^b$;

A is selected from the group consisting of single covalent bond and (CH(R$^{15}$))$_{pa}$—(W$^7$)$_{rr}$ wherein rr is an integer selected from 0 through 1, pa is an integer selected from 0 through 3, and W$^7$ is selected from the group consisting of (R$^7$)NC(O) and N(R$^7$);

R$^7$ is selected from the group consisting of hydrido, hydroxy and alkyl;

R$^{15}$ is selected from the group consisting of hydrido, halo, alkyl, and haloalkyl;

Ψ is NH;

R$^1$ and X$^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

R$^2$ is Z$^0$—Q;

Z$^0$ is selected from the group consisting of a covalent single bond, O, S, NH, and CH$_2$;

Q is selected from the group consisting of aryl and heteroaryl wherein a carbon adjacent to the carbon at the point of attachment is optionally substituted by R$^9$, the other carbon adjacent to the carbon at the point of attachment is optionally substituted by R$^{13}$, a carbon adjacent to R$^9$ and two atoms from the carbon at the point of attachment is optionally substituted by R$^{10}$, a carbon adjacent to R$^{13}$ and two atoms from the carbon at the point of attachment is optionally substituted by R$^{12}$, and any carbon adjacent to both R$^{10}$ and R$^{12}$ is optionally substituted by R$^{11}$;

R$^9$, R$^{11}$, and R$^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

R$^{10}$ and R$^{12}$ are independently selected from the group consisting of hydrido, acetamido, haloacetamido, amidino, guanidino, alkyl, alkoxy, hydroxy, amino, alkoxyamino, alkylamino, alkylsulfonamido, amidosulfonyl, monoalkyl amidosulfonyl, dialkyl amidosulfonyl, hydroxyalkyl, aminoalkyl, carboalkoxy, carboxy, carboxyalkyl, carboxamido, halo, haloalkyl, and cyano;

K is CH$_2$;

E$^0$ is C(O)N(H);

Y$^0$ is formula (IV):

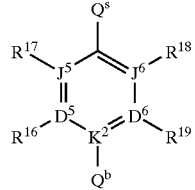

(IV)

wherein

D$^5$, D$^6$, J$^5$, and J$^6$ are independently selected from the group consisting of C, N, O, S and a covalent bond with the provisos that no more than one is a covalent bond, K$^2$ is C, no more than one of D$^5$, D$^6$, J$^5$, and J$^6$ is optionally O, no more than one of D$^5$, D$^6$, J$^5$, and J$^6$ is optionally S, one of D$^5$, D$^6$, J$^5$, and J$^6$ must be a covalent bond when two of D$^5$, D$^6$, J$^5$, and J$^6$ are O and S, and no more than four of D$^5$, D$^6$, J$^5$, and J$^6$ are N;

R$^{16}$, R$^{17}$, R$^{18}$, and R$^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

R$^{16}$ and R$^{19}$ are optionally Q$^b$ with the proviso that no more than one of R$^{16}$ and R$^{19}$ is Q$^b$ at the same time and that Q$^b$ is Q$^{be}$;

Q$^b$ is selected from the group consisting of NR$^{20}$R$^{21}$, Q$^{be}$ wherein Q$^{be}$ is hydrido, and C(NR$^{25}$)NR$^{23}$R$^{24}$, with the provisos that no more than one of R$^{20}$ and R$^{21}$ is hydroxy at the same time and that no more than one of R$^{23}$ and R$^{24}$ is hydroxy at the same time;

R$^{20}$, R$^{21}$, R$^{23}$, R$^{24}$, and R$^{25}$ are independently selected from the group consisting of hydrido, alkyl, and hydroxy;

Q$^s$ is selected from the group consisting of a single covalent bond, CH$_2$, and CH$_2$CH$_2$.

In another even more preferred embodiment of compounds of Formula I or a pharmaceutically acceptable salt thereof, J is O;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of R$^{32}$, R$^{33}$, R$^{34}$, R$^{35}$, and R$^{36}$;

R$^{32}$, R$^{33}$, R$^{34}$, R$^{35}$, and R$^{36}$ are independently selected from the group consisting of hydrido, acetamido, haloacetamido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and Q$^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

$\Psi$ is NH;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of covalent single bond, O, S, NH, and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, alkylamino, alkylsulfonamido, amidosulfonyl, monoalkyl amidosulfonyl, dialkyl amidosulfonyl, hydroxyalkyl, alkylenylamino, carboalkoxy, carboxy, carboxyalkyl, carboxamido, halo, haloalkyl, and cyano;

K is $CH_2$;

$E^0$ is $C(O)N(H)$;

$Y^0$ is formula (IV):

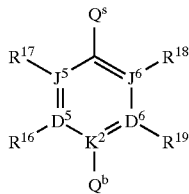

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$ and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a single covalent bond, $CH_2$, and $CH_2CH_2$.

In still another even more preferred embodiment of compounds of Formula I or a pharmaceutically acceptable salt thereof, J is O;

B is selected from the group consisting of C3–C7 cycloalkyl and C4 heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon three atoms from the point of attachment and adjacent to the $R^{10}$ position is optionally substituted with $R^{11}$, a ring carbon three atoms from the point of attachment and adjacent to the $R^{12}$ position is optionally substituted with $R^{33}$, and a ring carbon four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, alkylamino, alkylsulfonamido, amidosulfonyl, monoalkyl amidosulfonyl, dialkyl amidosulfonyl, hydroxyalkyl, alkylenylamino, carboalkoxy, carboxy, carboxyalkyl, carboxamido, halo, haloalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl and haloalkyl;

$\Psi$ is NH:

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^O$—Q;

$Z^O$ is selected from the group consisting of covalent single bond, O, S, NH, and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CH_2$;

$E^O$ is C(O)N(H);

$Y^O$ is formula (IV):

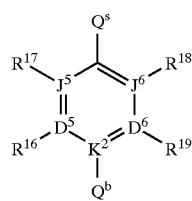

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In a further even more preferred embodiment of compounds of Formula I or a pharmaceutically acceptable salt thereof, said compound is the formula:

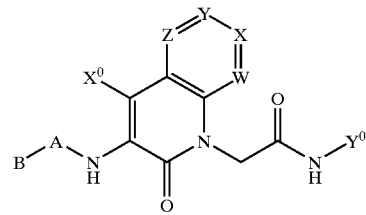

wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is a C3–C7 cycloalkyl or C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

A is a single covalent bond or $(CH(R^{15}))_{pa}-(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$X^o$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio; W, X, Y, and Z are independently selected from the group consisting of $C(R^9)$, $C(R^{10})$, $C(R^{11})$, $C(R^{12})$, N, $N(R^{10})$, O, S and a covalent bond with the provisos that one of W, X, Y, and Z is independently selected to be a covalent bond when one of W, X, Y, and Z is O or S, no more than one of W, X, Y, and Z is optionally O or S, and no more than three of W, X, Y, and Z are optionally N or $N(R^{10})$;

$Y^o$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$ and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a single covalent bond, $CH_2$, and $CH_2CH_2$.

In a fifth even more preferred embodiment of compounds of Formula I or a pharmaceutically acceptable salt thereof, said compound is the formula:

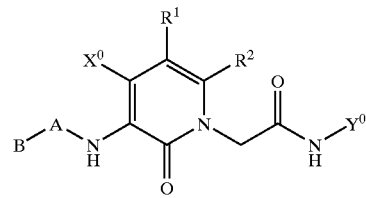

wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a single covalent bond or $(CH(R^{15}))_{pa}-(W^7)_{rr}$ wherein rr is 0 or 1, pa is an integer selected from 0 through 3, and W is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o-Q$;

$Z^o$ is a covalent single bond or $W^o-(CH(R^{42}))_p$ wherein p is 0 or 1 and $W^o$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano:

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfinyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In a sixth even more preferred embodiment of compounds of Formula I or a pharmaceutically acceptable salt thereof, said compound is the formula:

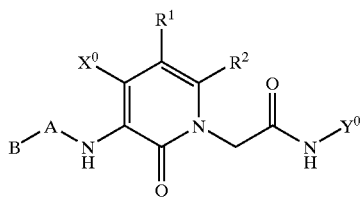

wherein;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$ and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and W is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond or $W^0$—$(CH(R^{42}))_p$ wherein p is 0 or 1 and $W^0$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^0$ is a covalent single bond;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $C(NR^{25})NR^{23}R^{24}$, and $N(R^{26})C(NR^{25})N(R^{23})(R^{24})$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a single covalent bond, $CH_2$, and $CH_2CH_2$.

In a seventh even more preferred embodiment of compounds of Formula I or a pharmaceutically acceptable salt thereof, said compound is the formula:

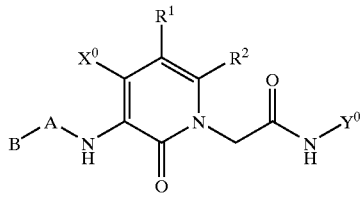

wherein;

B is a C3–C7 cycloalkyl or a C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$R^{33}$ and $R^{34}$ independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is a covalent single bond or $W^o$—$(CH(R^{42}))_p$ wherein p is 0 or 1 and $W^o$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$Y^o$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In a most preferred embodiment of compounds of Formula I or a pharmaceutically acceptable salt thereof, J is O;

B is the Formula:

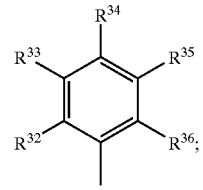

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

$\Psi$ is NH;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

K is $CH_2$;

$E^0$ is C(O)N(H);

$Y^0$ is formula (IV):

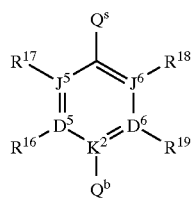

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$, are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl;

$Q^s$ is $CH_2$.

In another most preferred embodiment of compounds of Formula I or a pharmaceutically acceptable salt thereof, J is O;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

$\Psi$ is NH;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

K is $CH_2$;
$E^0$ is $C(O)N(H)$;
$Y^0$ is formula (IV):

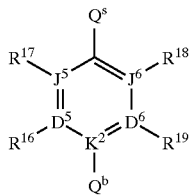

(IV)

wherein
$D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;
$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;
$R^{16}$ and $R^{19}$ are optionally $Q^b$ with the proviso that no more than one of $R^{16}$ and $R^{19}$ is $Q^b$ at the same time and that $Q^b$ is $Q^{be}$;
$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$;
$R^{20}$, $R^{21}$, $R^{23}$, $R^{24}$, $R^{25}$, and $R^{26}$ are independently selected from the group consisting of hydrido and alkyl;
$Q^s$ is $CH_2$.

In still another most preferred embodiment of compounds of Formula I or a pharmaceutically acceptable salt thereof,
J is O;
B is selected from the group consisting of C3–C7 cycloalkyl and C4 heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and nitrogens adjacent to the carbon at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon three atoms from the point of attachment and adjacent to the $R^{10}$ position is optionally substituted with $R^{11}$, a ring carbon three atoms from the point of attachment and adjacent to the $R^{12}$ position is optionally substituted with $R^{33}$, and a ring carbon four atoms from the point of attachment and adjacent to the $R^{11}$ and $R^{33}$ positions is optionally substituted with $R^{34}$;
$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;
$R^{33}$ and $R^{34}$ are independently selected from the group consisting of hydrido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, and cyano;
$R^{33}$ is optionally $Q^b$;
A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;
$R^7$ is selected from the group consisting of hydrido, hydroxy and alkyl;
$R^{15}$ is selected from the group consisting of hydrido, halo, alkyl, and haloalkyl;
$\Psi$ is NH;
$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;
$R^2$ is $Z^0$—Q;
$Z^0$ is a covalent single bond;
Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;
K is $CH_2$;
$E^0$ is $C(O)N(H)$;
$Y^0$ is formula (IV):

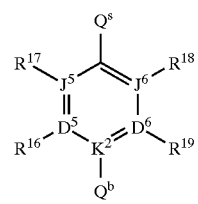

(IV)

wherein
$D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;
$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl;

$Q^s$ is $CH_2$.

In a further most preferred embodiment of compounds of Formula I or a pharmaceutically acceptable salt thereof, said compound is the formula:

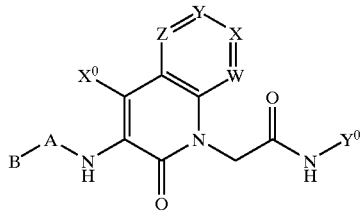

wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C7 cycloalkyl or C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent is to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

A is a single covalent bond or $(CH(R^{15}))_{pa}$—$(W^7)_{rr}$ wherein rr is 0 or 1, pa is an integer selected from 0 through 3, and $W^7$ is $N(R^7)$;

$R^7$ is selected from the group consisting of hydrido, hydroxy and alkyl;

$R^{15}$ is selected from the group consisting of hydrido, halo, alkyl, and haloalkyl;

$X^0$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

W, X, Y, and Z are independently selected from the group consisting of $C(R^9)$, $C(R^{10})$, $C(R^{11})$, $C(R^{12})$, and N with the proviso that no more than three of W, X, Y, and Z are N at the same time;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently hydrido or alkyl;

$Q^s$ is $CH_2$.

In a fifth most preferred embodiment of compounds of Formula I or a pharmaceutically acceptable salt thereof, said compound is the formula:

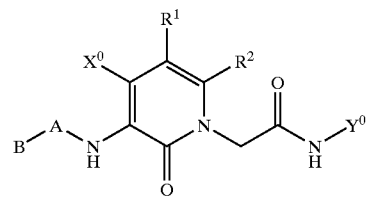

wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond or $W^0$—$(CH_2)_p$ wherein p is 0 or 1 and $W^0$ is selected from the group consisting of O, S, and N(H);

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^0$ is a covalent single bond;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$Y^o$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$; and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl;

$Q^s$ is $CH_2$.

In a sixth most preferred embodiment of compounds of Formula I or a pharmaceutically acceptable salt thereof, said compound is the formula:

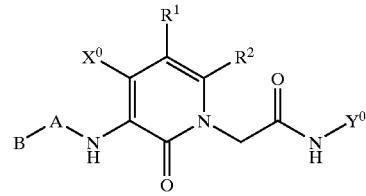

wherein;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond or $W^0$—$(CH_2)_p$ wherein p is 0 or 1 and $W^0$ is selected from the group consisting of O, S, and N(H);

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^0$ is a covalent single bond;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently selected from the group consisting of hydrido and alkyl;

$Q^s$ is $CH_2$.

In a seventh most preferred embodiment of compounds of Formula I or a pharmaceutically acceptable salt thereof, said compound is the formula:

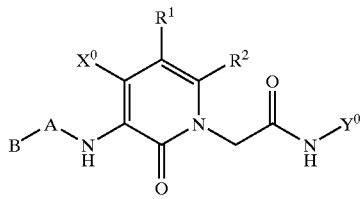

wherein;

B is a C3–C7 cycloalkyl or a C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, and cyano;

$R^{33}$ is optionally $Q^b$;

A is a single covalent bond or $(CH(R^{15}))_{pa}-(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0-Q$;

$Z^0$ is a covalent single bond or $W^0-(CH_2)_p$ wherein p is 0 or 1 and $W^0$ is selected from the group consisting of O, S, and N(H);

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^0$ is a covalent single bond;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl;

$Q^s$ is $CH_2$.

In a preferred specific embodiment of Formula I, compounds have the Formula I-S:

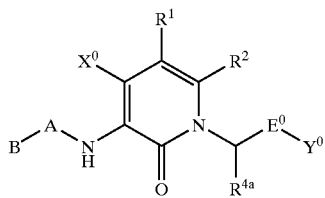

(I-S)

or a pharmaceutically acceptable salt thereof, wherein;
B is the Formula:

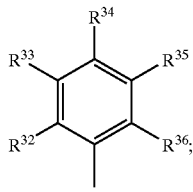

$R^{32}$, $R^{33}$, $R^{34}$, $R^{35}$, and $R^{36}$ are independently selected from the group consisting of hydrido, amidino, guanidino, carboxy, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro 1-trifluoromethyl-1-hydroxyethyl, carboxymethyl, methoxycarbonyl, ethoxycarbonyl, amidocarbonyl, N-methylamidocarbonyl, N,N-dimethylaminocarbonyl, cyano, and $Q^b$;

B is selected from the group consisting of hydrido, trimethylsilyl, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1methyl-2-pentenyl, 1-methyl-3-pentenyl, 1-methylpentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl, 6-octynyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-2-heptynyl, 1-methyl-3-heptynyl, 1-methyl-4-heptynyl, 1-methyl-5-heptynyl, 1-methyl-6-heptynyl, 1-methyl-2-heptynyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl-4-hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propylpentenyl, 1-butyl-2-butenyl, 1-propyl-2-pentynyl, 1-propyl-3-pentynyl, 1-butyl-2-butynyl, 1-butyl-3-butenyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

B is optionally selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, cyclopentyl, cyclohexyl, adamantyl, norbornyl, 3-trifluoromethylnorbornyl, bicyclo[3.1.0]hexanyl, cycloheptyl, and cyclooctyl, wherein each ring carbon is optionally substituted with $R^{33}$, ring carbons or a nitrogen adjacent to the carbon atom at the point of attachment are optionally substituted with $R^9$ or $R^{13}$, a ring carbon or a nitrogen adjacent to the $R^9$ position and two atoms from the point of attachment is optionally substituted with $R^{10}$, and a ring carbon or a nitrogen adjacent to the $R^{13}$ position and two atoms from the point of attachment is optionally substituted with $R^{12}$;

$R^9$, $R^{10}$, $R^{11}$, $R^{12}$, and $R^{13}$ are independently selected from the group consisting of hydrido, amidino, guanidino, carboxy, carboxymethyl, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, and cyano;

A is selected from the group consisting of single covalent bond, O, S, NH, N(CH$_3$), N(OH), C(O), CH$_2$, CH$_3$CH, CF$_3$CH, NHC(O), N(CH$_3$)C(O), C(O)NH, C(O)N(CH$_3$), CF$_3$CC(O), C(O)CCH$_3$, C(O)CCF$_3$, CH$_2$C(O), (O)CCH$_2$, CH$_2$CH$_2$, CH$_2$CH$_2$CH$_2$, CH$_3$CHCH$_2$, CF$_3$CHCH$_2$, CH$_3$CC(O)CH$_2$, CF$_3$CC(O)CH$_2$, CH$_2$C(O)CCH$_3$, CH$_2$C(O)CCF$_3$, CH$_2$CH$_2$C(O), and CH$_2$(O)CCH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$R^1$ and $X^o$ are independently selected from the group consisting, of hydrido, hydroxy, amino, thiol, amidino, hydroxyamino, aminomethyl, 1-aminoethyl, 2-aminoethyl, methylamino, dimethylamino, cyano, methyl, ethyl, isopropyl, propyl, trifluoromethyl, pentafluoroethyl, 2,2,2-trifluoroethyl, 2,2,3,3,3-pentafluoropropyl, methoxy, ethoxy, propoxy, hydroxymethyl, 1-hydroxyethyl, 2-hydroxyethyl, methoxyamino, ethoxyamino, methylthio, ethylthio, trifluoromethoxy, 1,1,2,2-tetrafluoroethoxy, fluoro, chloro, and bromo;

$R^2$ is $Z^0$—Q;

$Z^0$ is selected from the group consisting of covalent single bond, O, S, NH, $CH_2$, $CH_2CH_2$, CH(OH), $CH(NH_2)$, $CH_2CH(OH)$, $CH_2CHNH_2$, $CH(OH)CH_2$, and $CH(NH_2)CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazinyl, 1,2,3-triazin-4-yl, and 1,2,3-triazin-5-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CHR^{4a}$ wherein $R^{4a}$ is selected from the group consisting of methyl, ethyl, propyl, isopropyl, hydroxymethyl, 1-hydroxyethyl, methoxymethyl, trifluoromethyl, pentafluoroethyl, 2,2,2-trifluoromethyl, methylthiomethyl, and hydrido;

$E^0$ is a covalent single bond, C(O)N(H), (H)NC(O), and $S(O)_2N(H)$;

$Y^0$ is selected from the group of formulas consisting of:

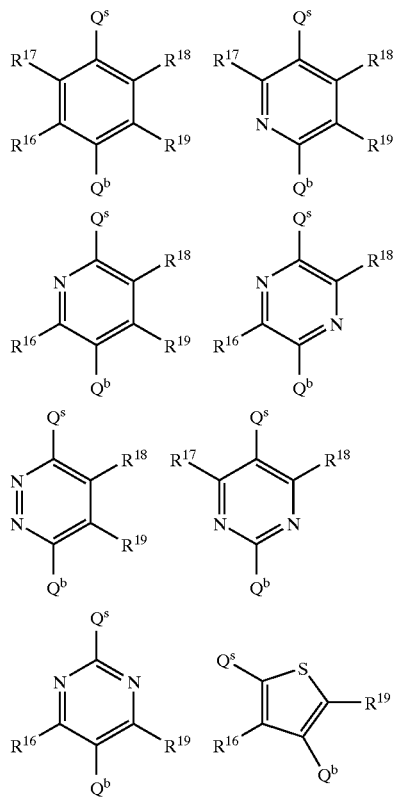

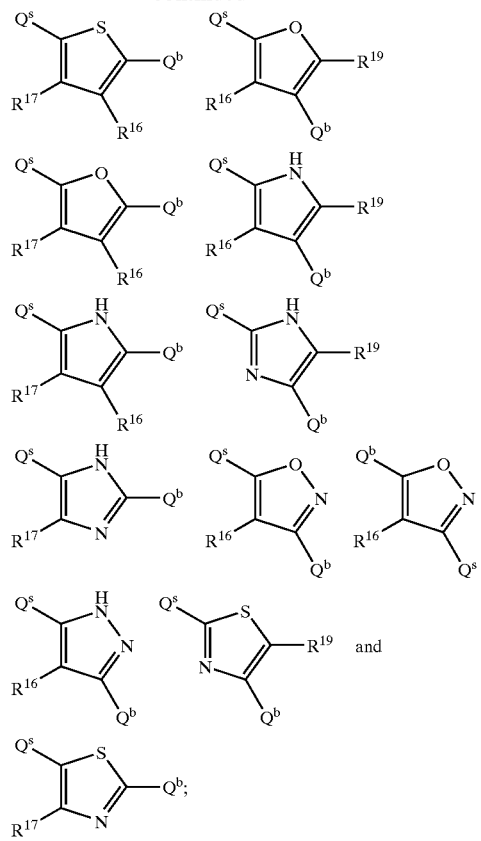

$R^{16}$, $R^{17}$, $R^{18}$, and $R^{19}$ are independently selected from the group consisting of hydrido, methyl, ethyl, isopropyl, propyl, amidino, guanidino, carboxy, methoxy, ethoxy, isopropoxy, propoxy, hydroxy, amino, methoxyamino, ethoxyamino, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$ and $N(R^{26})C(NR^{25})N(R^{23})(R^{24})$, with the proviso that no more than one of $R^{20}$ and $R^{21}$ is hydroxy, N-methylamino, and N,N-dimethylamino at the same time and that no more than one of $R^{23}$ and $R^{24}$ is hydroxy, N-methylamino, and N,N-dimethylamino at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, hydroxy, 2-aminoethyl, 2-(N-methylamino)ethyl, and 2-(N,N-dimethylamino)ethyl;

$Q^s$ is selected from the group consisting of a single covalent bond, $CH_2$, $CH_2CH_2$, $CH_3CH$, $CF_3CH$, $CH_3CHCH_2$, $CF_3CHCH_2$, $CH_2(CH_3)CH$, CH=CH, CF=CH, $C(CH_3)$=CH, CH=$CHCH_2$, CF=$CHCH_2$, $C(CH_3)$=$CHCH_2$, $CH_2CH$=CH, $CH_2CF$=CH, $CH_2C$ ($CH_3$)=CH, $CH_2CH$=$CHCH_2$, $CH_2CF$=$CHCH_2$, $CH_2C$($CH_3$)=$CHCH_2$, $CH_2CH$=$CHCH_2CH_2$, $CH_2CF$=$CHCH_2CH_2$, and $CH_2C(CH_3)$=$CHCH_2CH_2$.

In a more preferred specific embodiment of Formula I, compounds have the Formula I-MPS wherein B is an aromatic:

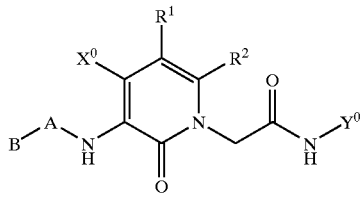

(I-MPS wherein B is aromatic)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, N($CH_3$), N(OH), $CH_2$, $CH_3CH$, $CF_3CH$, NHC(O), N($CH_3$)C(O), C(O)NH, C(O)N($CH_3$), $CH_2CH_2$, $CH_2CH_2CH_2$, $CH_3CHCH_2$, and $CF_3CHCH_2$;

$R^1$ and $X^o$ are independently selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^o$—Q;

$Z^o$ is selected from the group consisting of covalent single bond, O, S, NH, N($CH_3$), $OCH_2$, $SCH_2$, N(H)$CH_2$, and N($CH_3$)$CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylanidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamin, 4-chloro-3-ethylphenylamino, 3-chlorobenzyloxy, 4-chlorobenzyloxy, 4-chlorobenzylsulfonyl, 4-clorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluor-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$R^{16}$ or $R^{19}$ is optionally $C(NR^{25})NR^{23}R^{24}$ with the proviso that $R^{16}$, $R^{19}$, and $Q^b$ are not simultaneously hydrido;

$Q^b$ is $C(NR^{25})NR^{23}R^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

In another more preferred specific embodiment of Formula I, compounds have the Formula I-MPS wherein B is a non-cyclic substituent:

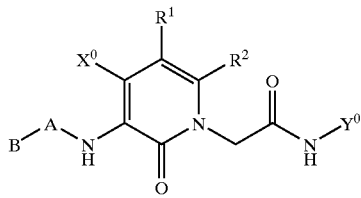

(I-MPS wherein B is a non-cyclic substituent)
or a pharmaceutically acceptable salt thereof, wherein;

B is selected from the group consisting of hydrido, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethyl amino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, $N(CH_3)$, N(OH), $CH_2$, $CH_3CH$, $CF_3CH$, NHC(O), $N(CH_3)C(O)$, C(O)NH, $C(O)N(CH_3)$, $CH_2CH_2$, $CH_2CH_2CH_2$, $CH_3CHCH_2$, and $CF_3CHCH_2$;

A is optionally selected from the group consisting of $CH_2N(CH_3)$, $CH_2N(CH_2CH_3)$, $CH_2CH_2N(CH_3)$, and $CH_2CH_2N(CH_2CH_3)$ with the proviso that B is hydrido;

$R^1$ and $X^o$ are independently selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^o$—Q;

$Z^o$ is selected from the group consisting of covalent single bond, O, S, NH, $N(CH_3)$, $OCH_2$, $SCH_2$, $N(H)CH_2$, and $N(CH_3)CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cycloalkylaminocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$R^{16}$ or $R^{19}$ is optionally selected from the group consisting of $NR^{20}R^{21}$, $C(NR^{25})NR^{23}R^{24}$, and $N(R^{26})C(NR^{25})N(R^{23})(R^{24})$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy.

In still another more preferred specific embodiment of Formula I, compounds have the Formula I-MPS wherein B is a non-aromatic cyclic substituent:

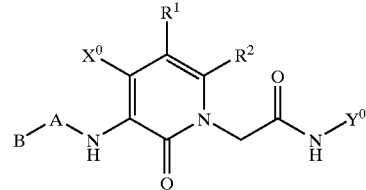

(I-MPS wherein B is a non-aromatic cyclic substituent) or a pharmaceutically acceptable salt thereof, wherein;

B is selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, 7-oxabicyclo[2.2.1]heptan-2-yl, bicyclo[3.1.0]hexan-6-yl, cycloheptyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, and a ring carbon or nitrogen adjacent to the $R^{13}$ position and two atoms from the point of attachment is optionally substituted with $R^{12}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethyl amino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroetylphenoxy, 3-(1,1,2,2-tetrafluoroethoxy)phenoxy, and 3-trifluoromethylthiophenoxy;

$R^{33}$ is selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-methylamidocarbonyl, cyano, and $Q^b$;

A is selected from the group consisting of single covalent bond, NH, N(CH$_3$), N(OH), CH$_2$, CH$_3$CH, CF$_3$CH, NHC(O), N(CH$_3$)C(O), C(O)NH, C(O)N(CH$_3$), CH$_2$CH$_2$, CH$_2$CH$_2$CH$_2$, CH$_3$CHCH$_2$, and CF$_3$CHCH$_2$;

$R^1$ and $X^o$ are independently selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^o$—Q;

$Z^o$ is selected from the group consisting of covalent single bond, O, S, NH, N(CH$_3$), OCH$_2$, SCH$_2$, N(H)CH$_2$, and N(CH$_3$)CH$_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$R^{16}$ or $R^{19}$ is optionally C(NR$^{25}$)NR$^{23}$R$^{24}$ with the proviso that $R^{16}$, $R^{19}$, and $Q^b$ are not simultaneously hydrido;

$Q^b$ is C(NR$^{25}$)NR$^{23}$R$^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

In a further even more preferred embodiment of compounds of Formula I, compounds have the Formula I-FARMPS wherein there are two fused aromatic rings:

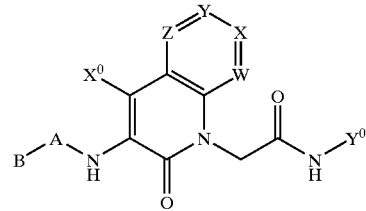

(I-FARMPS)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5- triazin-2-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

B is selected from the group consisting of hydrido, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-difluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

B is optionally selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, 7-oxabicyclo[2.2.1]heptan-2-yl, bicyclo[3.1.0]hexan-6-yl, cycloheptyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

$R^9$ and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, aminocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifuoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluorethoxy)phenoxy, and 3-trifluoromethylthiophenoxy;

A is selected from the group consisting of single covalent bond, NH, N(CH$_3$), N(OH), CH$_2$, CH$_3$CH, CF$_3$CH, NHC(O), N(CH$_3$)C(O), C(O)NH, C(O)N(CH$_3$), CH$_2$CH$_2$, CH$_2$CH$_2$CH$_2$, CH$_3$CHCH$_2$, and CF$_3$CHCH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$X^o$ is selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

W, X, Y, and Z are independently selected from the group consisting of CH, N, CF, CCl, C—CN, C—CH$_3$, C—CH$_2$CH$_3$, C—NH$_2$, C—CH$_2$NH$_2$, C—CH$_2$NHCH$_3$, C—NHCH$_3$, C—N(CH$_3$)$_2$, C—CH(NH$_2$)CH$_3$, C—CH$_2$CH$_2$NH$_2$, C—NHOCH$_3$, C—NHOCH$_2$CH$_3$, C—C(NH)NH$_2$, C—C(NOH)NH$_2$, C—OH, C—CH$_2$OH, C—CH$_2$CH$_2$OH, C—CH(OH)CH$_3$, C—OCH$_3$, C—OCH$_2$CH$_3$, C—CO$_2$H, C—CO$_2$CH$_3$, C—C(O)NH$_2$, C—C(O)NHCH$_3$, C—C(O)N(CH$_3$)$_2$, N-benzylamidocarbonyl-C, N-(2-chlorobenzyl)amidocarbonyl-C, N-(3-fluorobenzyl)amidocarbonyl-C, N-(2-trifluoromethylbenzyl)amidocarbonyl-C, N-(1-phenylethyl)amidocarbonyl-C, N-(1-methyl-1-phenylethyl)amidocarbonyl-C, N-benzylamidosulfonyl-C, N-(2-chlorobenzyl)amidosulfonyl-C, N-ethylaminocarbonyl-C, N-isopropylamidocarbonyl-C, N-propylamidocarbonyl-C, N-isobutylamidocarbonyl-C, N-(2-butyl)amidocarbonyl-C, N-cyclobutylamidocarbonyl-C, N-cyclopentylamidocarbonyl-C, N-cyclohexylamidocarbonyl-C, C—NH(O)CCH$_3$, and C—NH(O)CCF$_3$;

$R^{16}$ or $R^{19}$ is optionally selected from the group consisting of $NR^{20}R^{21}$, $C(NR^{25})NR^{23}R^{24}$, and $N(R^{26})C(NR^{25})N(R^{23})(R^{24})$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy.

The more preferred specific embodiment (I-MPS) and (I-FARMPS) compounds of the present invention having the Formula:

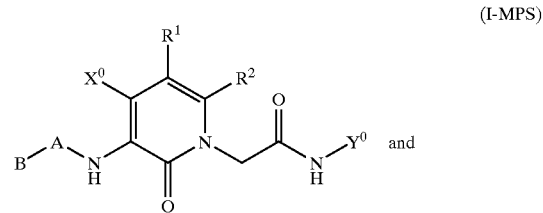

(I-MPS)

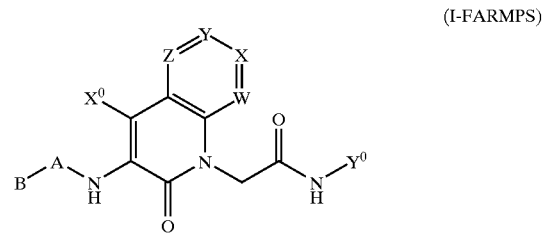

(I-FARMPS)

or a pharmaceutically acceptable salt thereof, have common structural units, wherein;

$Y^0$ is selected from the group of formulas consisting of:

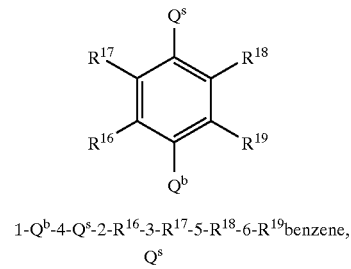

1-$Q^b$-4-$Q^s$-2-$R^{16}$-3-$R^{17}$-5-$R^{18}$-6-$R^{19}$benzene,

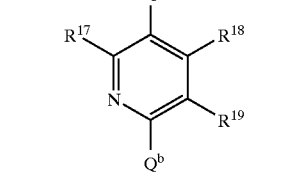

2-$Q^b$-5-$Q^s$-6-$R^{17}$-4-$R^{18}$-3-$R^{19}$pyridine,

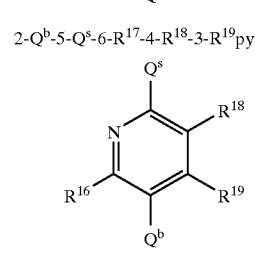

3-$Q^b$-6-$Q^s$-2-$R^{16}$-5-$R^{18}$-4-$R^{19}$pyridine,

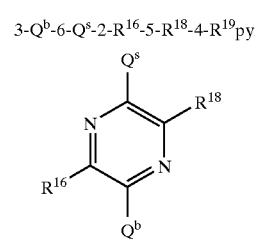

2-$Q^b$-5-$Q^s$-3-$R^{16}$-6-$R^{18}$pyrazine,

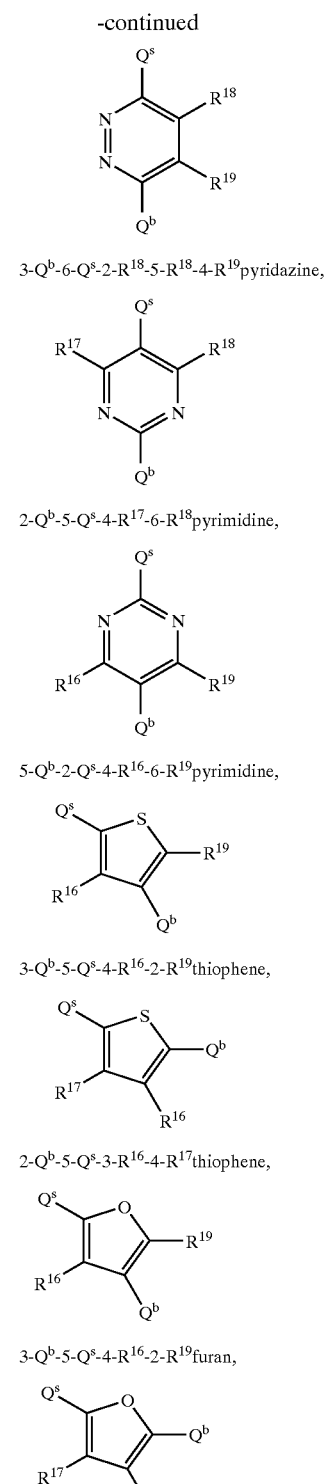

3-Q$^b$-6-Q$^s$-2-R$^{18}$-5-R$^{18}$-4-R$^{19}$pyridazine,

2-Q$^b$-5-Q$^s$-4-R$^{17}$-6-R$^{18}$pyrimidine,

5-Q$^b$-2-Q$^s$-4-R$^{16}$-6-R$^{19}$pyrimidine,

3-Q$^b$-5-Q$^s$-4-R$^{16}$-2-R$^{19}$thiophene,

2-Q$^b$-5-Q$^s$-3-R$^{16}$-4-R$^{17}$thiophene,

3-Q$^b$-5-Q$^s$-4-R$^{16}$-2-R$^{19}$furan,

2-Q$^b$-5-Q$^s$-3-R$^{16}$-4-R$^{17}$furan,

3-Q$^b$-5-Q$^s$-4-R$^{16}$-2-R$^{19}$pyrrole,

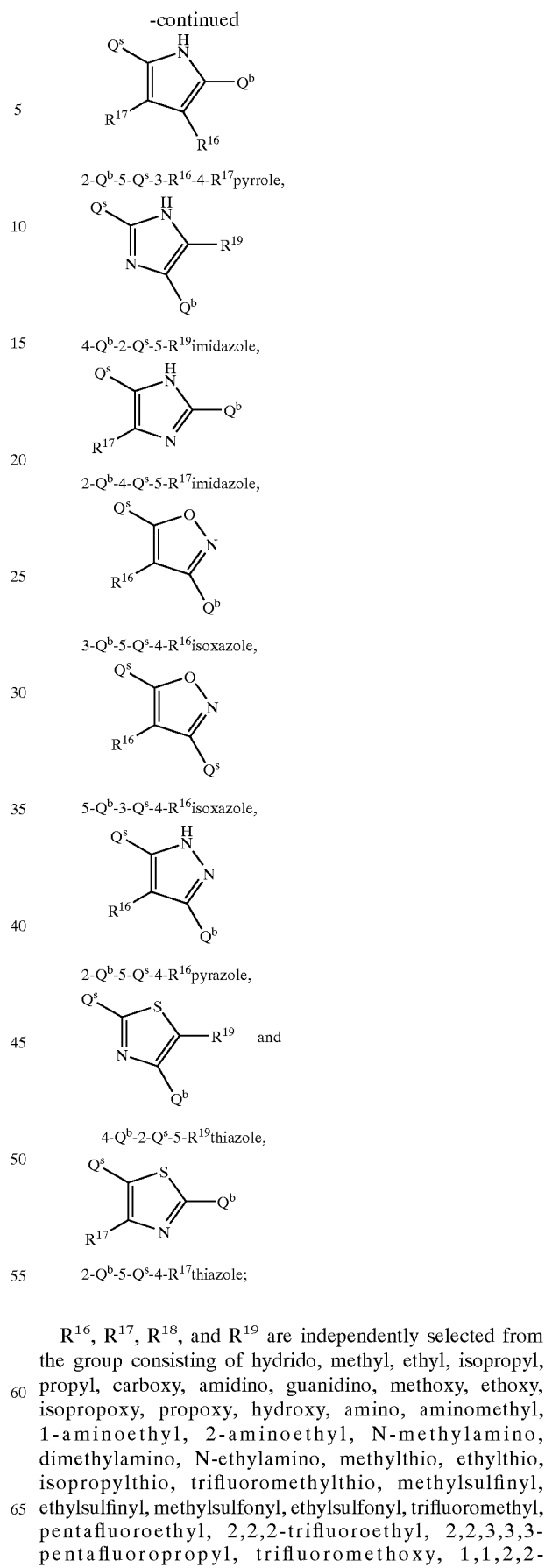

2-Q$^b$-5-Q$^s$-3-R$^{16}$-4-R$^{17}$pyrrole,

4-Q$^b$-2-Q$^s$-5-R$^{19}$imidazole,

2-Q$^b$-4-Q$^s$-5-R$^{17}$imidazole,

3-Q$^b$-5-Q$^s$-4-R$^{16}$isoxazole,

5-Q$^b$-3-Q$^s$-4-R$^{16}$isoxazole,

2-Q$^b$-5-Q$^s$-4-R$^{16}$pyrazole,

4-Q$^b$-2-Q$^s$-5-R$^{19}$thiazole,

2-Q$^b$-5-Q$^s$-4-R$^{17}$thiazole;

and

R$^{16}$, R$^{17}$, R$^{18}$, and R$^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2- tetrafluoroethoxy, fluoro, chloro, bromo, hydroxymethyl, 1-hydroxyethyl, 2-hydroxyethyl, and cyano;

$Q^s$ is selected from the group consisting of a single covalent bond, $CH_2$, and $CH_2CH_2$.

In a most preferred specific embodiment of Formula I, compounds have the Formula I-EMPS wherein B is an aromatic:

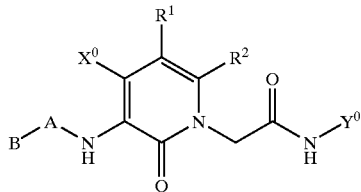

(I-EMPS wherein B is aromatic)
or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, and 5-isoxazolyl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, $N(CH_3)$, $CH_2$, $CH_3CH$, and $CH_2CH_2$;

$X^o$ is selected from the group consisting of hydrido, hydroxy, amino, amidino, aminomethyl, cyano, methyl, trifluoromethyl, hydroxymethyl, chloro, and fluoro;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is $Z^o$—Q;

$Z^o$ is selected from the group consisting of covalent single bond, O, S, NH, $OCH_2$, $SCH_2$, and $N(H)CH_2$;

Q is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-benzylamidocarbonyl, N-(2-chlorobenzyl) amidocarbonyl, N-(3-fluorobenzyl)amidocarbonyl, N-(2-trifluoromethylbenzyl)amidocarbonyl, N-(1-phenylethyl) amidocarbonyl, N-(1-methyl-1-phenylethyl)amidocarbonyl, N-benzylamidosulfonyl, N(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromxethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$Q^b$ is $NR^{20}R^{21}$ or $C(NR^{25})NR^{23}R^{24}$;

$R^{20}$, $R^{21}$, $R^{23}$, $R^{24}$, and $R^{25}$ are independently selected from the group consisting of hydrido, methyl, and ethyl.

In another most preferred specific embodiment of Formula I, compounds have the Formula I-EMPS wherein B is a non-cyclic substituent:

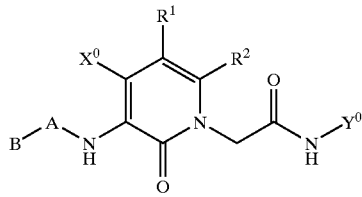

(I-EMPS wherein B is a non-cyclic substituent)
or a pharmaceutically acceptable salt thereof, wherein;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5 trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, N(CH$_3$), CH$_2$, CH$_3$CH, and CH$_2$CH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$X^o$ is selected from the group consisting of hydrido, hydroxy, amino, amidino, aminomethyl, cyano, methyl, trifluoromethyl, hydroxymethyl, chloro, and fluoro;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is $Z^o$—Q;

$Z^o$ is a covalent single bond;

Q is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^o$ is a covalent single bond;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-(3-fluorobenzyl) amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, (amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$Q^b$ is selected from the group consisting of NR$^{20}$R$^{21}$, C(NR$^{25}$)NR$^{23}$R$^{24}$, and N(R$^{26}$)C(NR$^{25}$)N(R$^{23}$)(R$^{24}$), with the proviso that said $Q^b$ group is bonded directly to a carbon atom;

$R^{20}$, $R^{21}$, $R^{23}$, $R^{24}$, $R^{25}$, and $R^{26}$ are independently selected from the group consisting of hydrido, methyl, and ethyl.

In still another most preferred specific embodiment of Formula I, compounds have the Formula I-EMPS wherein B is a non-aromatic cyclic substituent:

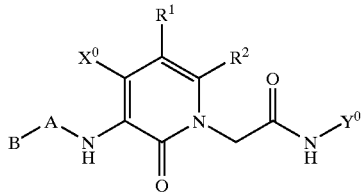

(I-EMPS wherein B is a non-aromatic cyclic substituent) or a pharmaceutically acceptable salt thereof, wherein;

B is selected from the group consisting of cyclopropyl, cyclobutyl, cyclopentyl, cyclohexyl, cycloheptyl, oxalan-2-yl, 2-(2R)bicyclo[2.2.1]-heptyl, oxetan-3-yl, azetidin-1-yl, azetidin-2-yl, azetidin-3-yl, bicyclo[3.1.0]hexan-6-yl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment are optionally substituted with $R^{10}$, and a ring carbon or nitrogen atom adjacent to the $R^{13}$ position and two atoms from the point of attachment is optionally substituted with $R^{12}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-(3-fluorobenzyl) amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guaridino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$R^{33}$ is selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, N(CH$_3$), CH$_2$, CH$_3$CH, CH$_2$CH$_2$, and CH$_2$CH$_2$CH$_2$;

$X^o$ is selected from the group consisting of hydrido, hydroxy, amino, amidino, aminomethyl, cyano, methyl, trifluoromethyl, hydroxymethyl, chloro, and fluoro;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is $Z^0$—Q;

$Z^0$ is selected from the group consisting of covalent single bond, O, S, NH, OCH$_2$, SCH$_2$, and N(H)CH$_2$;

Q is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$, with the proviso that Q is other than a phenyl when $Z^0$ is a covalent single bond;

$Q^b$ is NR$^{20}$R$^{21}$ or C(NR$^{25}$)NR$^{23}$R$^{24}$;

$R^{20}$, $R^{21}$, $R^{23}$, $R^{24}$, and $R^{25}$ are independently selected from the group consisting of hydrido, methyl, and ethyl.

In a further most preferred embodiment of compounds of Formula I, compounds have the Formula I-FARMPS wherein there are two fused aromatic rings:

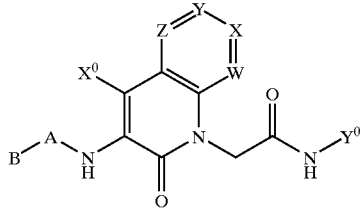

(I-FARMPS)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, and 5-isoxazolyl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

B is selected from the group consisting of cyclopropyl, cyclobutyl, cyclopentyl, cyclohexyl, cycloheptyl, oxalan-2-yl, 2-(2R)bicyclo[2.2.1]-heptyl, oxetan-3-yl, azetidin-1-yl, azetidin-2-yl, azetidin-3-yl, bicyclo[3.1.0]hexan-6-yl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment are optionally substituted with $R^{10}$, and a ring carbon or nitrogen atom adjacent to the $R^{13}$ position and two atoms from the point of attachment is optionally substituted with $R^{12}$;

$R^9$ and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-(3-fluorobenzyl) amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

A is selected from the group consisting of single covalent bond, NH, N(CH$_3$), CH$_2$, CH$_3$CH, and CH$_2$CH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

X$^o$ is selected from the group consisting of hydrido, hydroxy, amino, amidino, aminomethyl, cyano, methyl, trifluoromethyl, hydroxymethyl, chloro, and fluoro;

W and Z are independently selected from the group consisting of CH, N, CF, CCl, C—CN, C—NH$_2$, C—CH$_2$NH$_2$, C—NHCH$_3$, C—OH, C—CH$_2$OH, C—CO$_2$H, and C—C(O)NH$_2$;

X and Y are independently selected from the group consisting of CH, N, CF, C—CN, C—CH$_3$, C—NH$_2$, C—CH$_2$NH$_2$, C—CH$_2$NHCH$_3$, C—NHCH$_3$, C—CH(NH$_2$)CH$_3$, C—CH$_2$CH$_2$NH$_2$, C—NHOCH$_3$, C—C(NH)NH$_2$, C—C(NOH)NH$_2$, C—OH, C—CH$_2$OH, C—CH$_2$CH$_2$OH, C—CH(OH)CH$_3$, C—OCH$_3$, C—CO$_2$H, C—C(O)NH$_2$, C—C(O)NHCH$_3$, C—CH$_2$CO$_2$H, N-benzylamidocarbonyl-C, N-(2-chlorobenzyl)amidocarbonyl-C, N-(3-fluorobenzyl)amidocarbonyl-C, N-(2-trifluoromethylbenzyl)amidocarbonyl-C, N-(1-phenylethyl)amidocarbonyl-C, N-(1-methyl-1-phenylethyl)amidocarbonyl-C, N-benzylamidosulfonyl-C, N-(2-chlorobenzyl)amidosulfonyl-C, N-ethylamidocarbonyl-C, N-isopropylamidocarbonyl-C, N-propylamidocarbonyl-C, N-isobutylamidocarbonyl-C, N-(2-butyl)amidocarbonyl-C, N-cyclobutylamidocarbonyl-C, N-cyclopentylamidocarbonyl-C, N-cyclohexylamidocarbonyl-C;

Q$^b$ is selected from the group consisting of NR$^{20}$R$^{21}$, C(NR$^{25}$)NR$^{23}$R$^{24}$, and N(R$^{26}$)C(NR$^{25}$)N(R$^{23}$)(R$^{24}$), with the proviso that said Q$^b$ group is bonded directly to a carbon atom;

R$^{20}$, R$^{21}$, R$^{23}$, R$^{24}$, R$^{25}$, and R$^{26}$ are independently selected from the group consisting of hydrido, methyl, and ethyl.

The most preferred specific embodiment (I-EMPS) compounds of the present invention having the Formula:

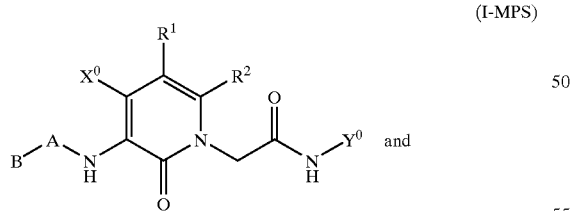

(I-MPS)

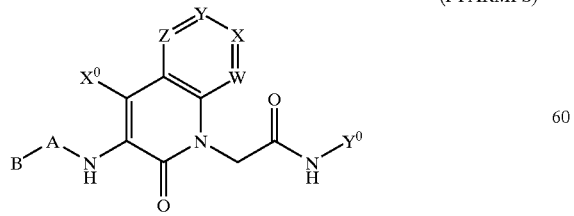

(I-FARMPS)

or a pharmaceutically acceptable salt thereof, have common structural units, wherein;

Y$^O$ is selected from the group of formulas consisting of:

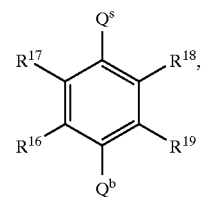

1-Q$^b$-4-Q$^s$-2-R$^{16}$-3-R$^{17}$-5-R$^{18}$-6-R$^{19}$benzene

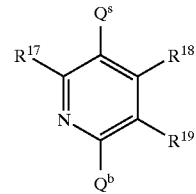

2-Q$^b$-5-Q$^s$-6-R$^{17}$-4-R$^{18}$-3-R$^{19}$pyridine,

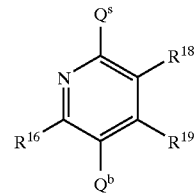

3-Q$^b$-6-Q$^s$-2-R$^{16}$-5-R$^{18}$-4-R$^{19}$pyridine,

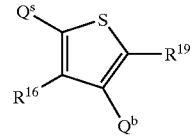

3-Q$^b$-5-Q$^s$-4-R$^{16}$-2-R$^{19}$thiophene,

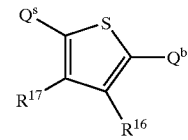

2-Q$^b$-5-Q$^s$-3-R$^{16}$-4-R$^{17}$thiophene,

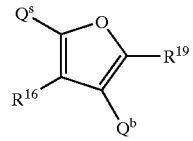

3-Q$^b$-5-Q$^s$-4-R$^{16}$-2-R$^{19}$furan,

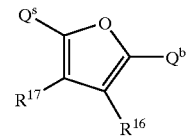

2-Q$^b$-5-Q$^s$-3-R$^{16}$-4-R$^{17}$furan,

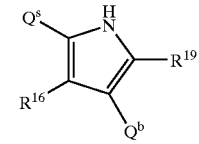

3-Q$^b$-5-Q$^s$-4-R$^{16}$-2-R$^{19}$pyrrole,

-continued

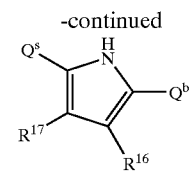

2-$Q^b$-5-$Q^s$-3-$R^{16}$-4-$R^{17}$pyrrole,

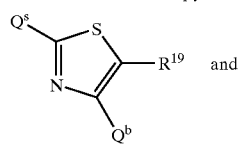 and

4-$Q^b$-2-$Q^s$-5-$R^{19}$thiazole,

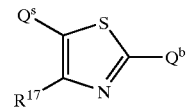

2-$Q^b$-5-$Q^s$-4-$R^{17}$thiazole;

$R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, hydroxymethyl, carboxy, and cyano;

$Q^s$ is $CH_2$.

The compounds of this invention can be used in anticoagulant therapy for the treatment and prevention of a variety of thrombotic conditions including coronary artery and cerebrovascular disease. The compounds of this invention can be used to inhibit serine protease associated with the coagulation cascade and factors II, VII, VIII, IX, X, XI, or XII. The compounds of the invention can inhibit the formation of blood platelet aggregates, inhibit the formation of fibrin, inhibit thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds can also be used in prophylactic treatment of subjects who are at risk of developing such disorders. The compounds can be used to lower the risk of atherosclerosis. The compounds of Formula (I) would also be useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In yet another embodiment of the present invention, the novel compounds are selected from the compounds set forth in Examples 1 through Example 29 and Example Table 1.

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a, nitrogen atom unless used as a prefix before a substituent on an amine or amide. The symbol "P" represents a phosphorus atom. The symbol "S" represents a sulfur atom. The symbol "H" represents a hydrido atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical —CH=, or two hydrido radicals may be attached to a carbon atom to form a "methylene" (—$CH_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene (CH$_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydroxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated and partially saturated heteroatom-containing ring-shaped radicals having from 4 through 15 ring members, herein referred to as "C4–C15 heterocyclyl", selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like. Said "heterocyclyl" group may be substituted as defined herein. Preferred heterocyclic radicals include five to twelve membered fused or unfused radicals.

The term "heteroaryl" embraces fully unsaturated heteroatom-containing ring-shaped aromatic radicals having from 4 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include the unsaturated heteromonocyclyl group of 5 to 6 contiguous members containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazole, tetrazolopyridazinyl [e.g., tetrazolo [1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5 to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazoyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heteroaryl" group may be substituted as defined herein. Preferred heteroaryl radicals include five and six membered unfused radicals. Non-limiting examples of heteroaryl radicals include 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyriridinyl, 3-pyridazinyl, 4-pyridazinyl, 1,3,5-triazin-2-yl, 1,2,4-triazin-3-yl, 1,2,4-triazin-5-yl, 1,2,4-triazinyl, 1,2,3-triazin-4-yl, and 1,2,3-triazin-5-yl, and the like.

The term "sulfonyl", whether used alone or linked to other terms such as alkylsulfonyl, denotes respectively divalent radicals —$SO_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl, embraces haloalkylsulfonyl radicals attached to an alkyl radical, where alkyl is defined as above.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to 15 carbon atoms. More preferred cycloalkyl radicals are "cycloalkyl" radicals having three to seven carbon atoms. Examples include radicals such as cyclopropyl, cyclobutyl, cyclopentyl, cyclohexyl and cycloheptyl. The term cyloalkyl embraces radicals having seven to 15 carbon atoms and having two to four rings. Examples include radicals such as norbornyl (i.e., bicyclo[2.2.1]heptyl) and adamantyl. The term "cycloalkylalkyl" embraces cycloalkyl-substituted. alkyl radicals. Preferable cycloalkylalkyl radicals are "cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "alkylthio" radicals having one to six carbon atoms. An example of "alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The term alkylamino denotes "monoalkylamino" and "dialkylamino" containing one or two alkyl radicals, respectively, attached to an amino radical. One or two alkyl radicals of the alkylamino may be optionally substituted with hydrogen bonding substitutents selected from the group consisting of hydroxy, amino, monoalkylamino, dialkylamino, amidino, guanidino, thiol, and alkoxy provided the alkyl radicals comprises two or more carbons.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylanino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 3-pentafluoroethylphenoxy, 3-(1,1,2,2-tetrafluoroethoxy)-phenoxy, and 4-tert -butylphenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "aralkoxy" radicals having phenyl radicals attached to alkoxy radical as described above. Examples of such radicals include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "heteroaralkoxy" radicals having heteroaryl radicals attached to alkoxy radical as described above. The term "heterocyclylalkoxy" embraces oxy-containing heterocyclylatkyl radicals attached through an oxygen atom to other radicals.

The term "haloheteroaryloxyalkyl" embraces heteroaryloxyalkyl radicals, as defined above, wherein one to four halo radicals are attached to an heteroaryloxy group.

The term "heteroarylamino" embraces heteroaryl radicals, as defined above, attached to an amino group. Examples of such radicals include pyridylamino. The term "heterocyclylamino" embraces heterocyclyl radicals, as defined above, attached to an amino group.

The term "heteroaralkylamino" embraces heteroaralkyl radicals, as defined above, attached to an amino group. Examples of such radicals include pyridylmethylamino. The term "heterocyclylalkylamino" embraces heterocyclylalkyl radicals, as defined above, attached to an amino group.

The term "heteroaryloxy" embraces heteroaryl radicals, as defined above, attached to an oxy group. Examples of such radicals include 2-thiophenyloxy, 2-pyrimidyloxy, 2-pyridyloxy, 3-pyridyloxy, and 4-pyridyloxy. The term "heterocyclyloxy" embraces heterocyclyl radicals, as defined above, attached to an oxy group.

The term, "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl. The term "heterocyclyloxyalkyl" embraces heterocyclyloxy radicals, as defined above, attached to an alkyl group.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamido" embraces amino, monoalkylamino, dialkylamino, monocycloalkylamino, alkylcycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a carbonyl group. The term "carboxamidoalkyl" embraces carboxamido radicals, as defined above, attached to an alkyl group. The term "carboxyalkyl" embraces a carboxy radical, as defined above, attached to an alkyl group. The term "carbalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl.

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "amino" denotes a nitrogen atom containing two substituents such as hydrido, hydroxy or alkyl and having one covalent bond available for bonding to a single atom such as carbon. Examples of such amino radicals include, for example, —NH₂, —NHCH₃, —NHOH, and —NHOCH₃. The term "imino" denotes a nitrogen atom containing one substituent such as hydrido, hydroxy or alkyl and having two covalent bonds available for bonding to a single atom such as carbon. Examples of such imino radicals include, for example, =NH, =NCH₃, =NOH, and =NOCH₃. The term "imino carbonyl" denotes a carbon radical having two of the four covalent bond sites shared with an imino group. Examples of such imino carbonyl radicals include, for example, C=NH, C=NCH₃, C=NOH, and C=NOCH₃. The term "amidino" embraces a substituted or unsubstituted amino group bonded to one of two available bonds of an iminocarbonyl radical. Examples of such amidino radicals include, for example, NH₂—C=NH, NH₂—C=NCH₃, NH₂—C=NOCH₃ and CH₃NH—C=NOH. The term "guanidino" denotes an amidino group bonded to an amino group as defined above where said amino group can be bonded to a third group. Examples of such guanidino radicals include, for example, NH₂—C(NH)—NH—, NH₂—C(NCH₃)—NH—, NH₂—C(NOCH₃)—NH—, and CH₃NH—C(NOH)—NH—.

The term "sulfonium" denotes a positively charged trivalent sulfur atom where said sulfur is substituted with three carbon based groups such as alkyl, alkenyl, aralkyl, or aryl. The term "dialkyl sulfonium" denotes a sulfonium group where said sulfur is substituted with two alkyl groups. Examples of such dialkylsulfonium radicals include, for example, (CH₃)₂S⁺—. The term "dialkyl sulfonium alkyl" denotes a dialkyl sulfonium group where said group is bonded to one bond of an alkylene group as defined above. Examples of such dialkylsulfoniumalkyl radicals include (CH₃)₂S⁺—CH₂CH₂—.

The term "phosphonium" denotes a positively charged tetravalent phosphorus atom where said phosphorus is substituted with four carbon based groups such as alkyl, alkenyl, aralkyl, or aryl. The term "trialkyl phosphonium" denotes a phosphonium group where said phosphorus is substituted with three alkyl groups. Examples of such trialkylphosphonium radicals include, for example, (CH₃)₃P⁺—.

Said "alkyl", "alkenyl", "alkynyl", "alkanoyl", "alkylene", "alkenylene", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroaralkylamino", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl", "amidino", "guanidino", "dialkylsulfonium", "trialkylphosphonium", and "dialkylsulfoniumalkyl" groups defined above may optionally have 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxyycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroaralkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxy-phosphonoalkyl.

The term "spacer" can include a covalent bond and a linear moiety having a backbone of 1 to 7 contiguous atoms. The spacer may have 1 to 7 atoms of a univalent or multi-valent chain. Univalent chains may be constituted by a radical selected from =C(H)—, =C(R²ᵃ)—, —O—, —S—, —S(O), —S(O)₂—, —NH—, —N(R²ᵃ)—, —N=, —CH(OH)—, =C(OH)—, —CH(OR²ᵃ)—, =C(OR²ᵃ)—, and —C(O)— wherein R²ᵃ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: alkylene, alkenyl, —O—, —O—CH₂—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$^{2a}$)O—, —O(CH$_2$CHR$^{2a}$)O—, —OCF$_2$—, —O(CF$_2$)$_2$O—, —S—, —S(O), —S(O)$_2$—, —N(H)—, —N(H)O—, —N(R$^{2a}$)O—, —N(R$^{2a}$)—, —C(O)—, —C(O)NH—, —C(O)NR$^{2a}$—, —N=, —OCH$_2$—, —SCH$_2$—, S(O)CH$_2$—, CH$_2$C(O)—, —CH(OH)—, =C(OH)—, —CH(OR$^{2a}$)—, =C(OR$^{2a}$), S(O)$_2$CH$_2$—, and —NR$^{2a}$CH$_2$— and many other radicals defined above or generally known or ascertained by one of skill-in-the art. Side chains may include substituents such as 1 or more non-hydrido substituents such as amidino, guanidino, dialkylsulfonium, trialkylphosphonium, dialkylsulfoniumalkyl, perhaloaralkyl, aralkylsulfonyl, arakylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, 1-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms. Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The present invention also comprises a treatment and prophylaxis in anticoagulant therapy for the treatment and prevention of a variety of thrombotic conditions including coronary artery and cerebrovascular disease in a subject, comprising administering to the subject having such disorder a therapeutically-effective amount of a compound of Formula (I):

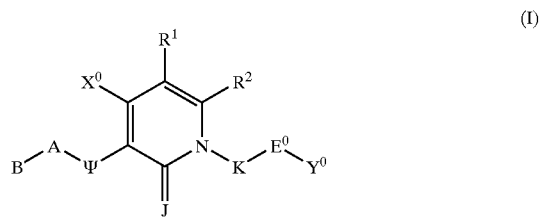

(I)

or a pharmaceutically-acceptable salt thereof.

As a further embodiment, compounds of the present invention of Formula (I) or a pharmaceutically-acceptable salt thereof as defined above, comprise a treatment and prophylaxis of coronary artery disease, cerebrovascular disease and other coagulation cascade related disorders in a subject, comprising administering to the subject having such disorder a therapeutically-effective amount of compounds of formula (I) of the present invention or a pharmaceutically-acceptable salt thereof.

Compounds of the present invention of Formula (I) or a pharmaceutically-acceptable salt thereof can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular gs, stents, orthopedic prothesis, cardiac prosthesis, and extracorporeal circulation systems.

Compounds of Formula (I) are capable of inhibiting activity of serine proteases related to the coagulation cascade, and thus could be used in the manufacture of a medicament, a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds also can be used to study the mechanism of action of coagulation cascade serine proteases to enable the design of better inhibitors and development of better assay methods. The compounds of Formula (I) would be also useful in prevention of cerebral vascular accident (CVA) or stroke.

Also included in the family of compounds of Formula (I) are the pharmaceutically-acceptable salts thereof. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula (I) may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula (I) include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula (I) by reacting, for example, the appropriate acid or base with the compound of Formula (I).

The present invention also comprises a pharmaceutical composition comprising a therapeutically-effective amount of a compound of Formulas (I) in association with at least one pharmaceutically-acceptable carrier, adjuvant or diluent. Pharmaceutical compositions of the present invention can comprise the active compounds of Formula (I) in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, ocular, or topically. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramusculary as depot injections or implants. Implants may employ inert materials such as biodegradable polymers or synthetic silicones, for example, Silastic, silicone rubber or other silicon containing polymers.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyphenyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil. peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions including coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be co-administered with suitable anti-platelet agreggation agents, including, but not limited to ticlopidine or clopidrogel, fibrinogen receptor antagonists (e.g. to treat or prevent unstable angina or to prevent reocculsion after angioplasty and restenosis), anticoagulants such as aspirin, warfarin or heparins, thrombolytic agents such as plasminogen activators or streptokinase to achieve synergistic effects in the treatment of various pathologies, lipid lowering agents including antihypercholesterolemics (e.g. HMG CoA reductase inhibitors such as mevastatin, lovastatin, simvastatin, pravastatin, and fluvastatin, HMG CoA synthatase inhibitors, etc.), anti-diabetic drugs, or other cardiovascular agents (loop diuretics, thiazide type diuretics, nitrates, aldosterone antagonistics (i.e., spironolactone and epoxymexlerenone), angiotensin converting enzyme (e.g. ACE) inhibitors, angiotensin II receptor antagonists, beta-blockers, antiarrythmics, anti-hypertension agents, and calcium channel blockers) to treat or prevent atheriosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

The present novel methods preferably employ compounds which selectively inhibit human TF-VIIA over the inhibition of both human Thrombin II and human factor Xa Preferably, the compounds have a human TF-VIIA $IC_{50}$ of less than 0.5 $\mu$M and also have a selectivity ratio of TF-VIIA inhibition over both human Thrombin II and human factor Xa inhibition of at least 10, and more preferably at least 100. Even more preferably, the compounds have a human TF-VIIA $IC_{50}$ of less than 0.1 µM and also have a selectivity ratio of TF-VIIA inhibition over both human Thrombin II and human factor Xa inhibition of at least 1000, and most preferably at least 10,000.

All mentioned references are incorporated by reference as if here written.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR, mass spectrometry, elemental composition, and similar procedures. These compounds also may be formed in vivo. The following examples contain detailed descriptions of the methods of preparation of compounds of Formula (I). These detailed descriptions fall within the scope and are presented for illustrative purposes only and are not intended as a restriction on the scope of the invention. All parts are by weight and temperatures are Degrees centigrade unless otherwise indicated.

The following general synthetic sequences are useful in making the present invention. Abbreviations used in the schemes and tables include: "AA" represents amino acids, "AcCN" represents acetonitrile, "AcOH" represents acetic acid, "BINAP" represents 2,2'-bis(diphenylphosphino-1,1'-binaphthyl, "BnOH" represents benzyl alcohol, "BnCHO" represents 2-phenylethanal, "BnSO$_2$Cl" represents benzylsulfonyl chloride, "Boc" represents tert-butyloxycarbonyl, "BOP" represents benzotriazol-1-yl-oxy-tris (dimethylamino), "bu" represents butyl, "dba" represents dibenzylideneacetone, "DCC" represents 1,3-dicyclohexylcarbodiimide, "DCM" represents dichloromethane or methylene chloride, "DIBAH" or "DIBAL" represents diisobutylaluminum hydride, "DMF" represents dimethylformamide, "DMSO" represents dimethylsulfoxide, "DPPA" represents diphenylphosphoryl azide", "EDC" represents 1-[3-(dimethylamino)propyl]-3-ethylcarbodiimide hydrochloride, "Ex. No." represents Example Number, "Fmoc" represents 9-fluorenylmethoxycarbonyl, "HOBt" represents hydroxybenzoltriazole", "LDA" represents lithium diisopropylamide, "MW" represents molecular weight, "NMM" represents N-methylmorpholine, "Ph" represents phenyl or aryl, "PHTH" represents a phthaloyl group, "pnZ" represents 4-nitrobenzyloxy-carbonyl, "PTC" represents a phase transfer catalyst, "py" represents pyridine, "RNH$_2$" represents a primary organic amine, "SEM" represents 2-(trimethylsilyl)ethoxy-methyl chloride, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, "TMSCN" represents trimethylsilyl cyanide, and "Cbz" or "Z" represents benzyloxycarbonyl.

GENERAL SYNTHETIC PROCEDURES AND SPECIFIC EXAMPLES

The pyridone compounds of the present invention can be synthesized, for example, according to the following procedures and Schemes given below.

A pyridone having a fused aryl or heteroaryl group can be considered to be a quinolone. A generic quinolinone analogous structure to the basic pyridone ring type is shown in FIG. 1. W, X, Y and Z are optionally selected, for example, from CH,

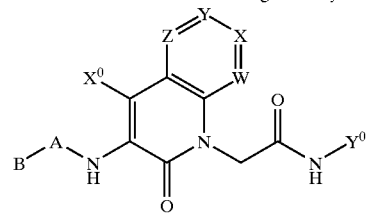

FIG. 1
Quinolinone Analogues of Pyridones

N, CF, CCl, C—CN, C—CH$_3$, C—CH$_2$CH$_3$, C—NH$_2$, C—CH$_2$NH$_2$, C—CH$_2$NHCH$_3$, C—NHCH$_3$, C—N(CH$_3$)$_2$, C—CH(NH$_2$)CH$_3$, C—CH$_2$CH$_2$NH$_2$, C—NHOCH$_3$, C—NHOCH$_2$CH$_3$, C—C(NH)NH$_2$, C—C(NOH)NH$_2$, C—OH, C—CH$_2$OH, C—CH$_2$CH$_2$OH, C—CH(OH)CH$_3$, C—OCH$_3$, C—OCH$_2$CH$_3$, C—CO$_2$H, C—CO$_2$CH$_3$, C—C(O)NH$_2$, C—CH(NH$_2$)CH$_3$, C—CH$_2$CH$_2$NH$_2$, C—NHOCH$_3$, C—C(NH)NH$_2$, C—C(NOH)NH$_2$, C—OH, C—CH$_2$OH, C—CH$_2$CH$_2$OH, C—CH(OH)CH$_3$, C—OCH$_3$, C—CO$_2$H, C—C(O)NH$_2$, C—C(O)NHCH$_3$, C—CH$_2$CO$_2$H, N-benzylamidocarbonyl-C, N-(2-chlorobenzyl)amidocarbonyl-C, N-(3-fluorobenzyl)amidocarbonyl-C, N-benzylamidosulfonyl-C, N-(2-trifluoromethylbenzyl)amidocarbonyl-C, N-ethylamidocarbonyl-C, N-(1-phenylethyl)amidocarbonyl-C, N-propylamidocarbonyl-C, N-(1-methyl-1-phenylethyl)amidocarbonyl-C, N-(2-chlorobenzyl)amidosulfonyl-C, N-isopropylamidocarbonyl-C, N-isobutylamidocarbonyl-C, N-(2-butyl)amidocarbonyl-C, N-cyclobutylamidocarbonyl-C, N-cyclopentylamidocarbonyl-C, N-cyclohexylamidocarbonyl-C. Quinolones in which W of W—X=Y—Z is attached to the four and five positions of the pyridone instead of the five and six positions can be prepared by comparable procedures. A general procedure for the preparation a wide variety of quinolone type 2-pyridones is summarized in Scheme 1 and Scheme 2. These procedures can accommodate the introduction of a wide range of substituents into the fused ring either as such, precursors groups for desired groups (for example, a nitro for subsequent conversion to an amino, an acetoxymethyl for subsequent hydrolysis to an hydroxymethyl or oxidation to an aldehyde or carboxylic acid, and the like) or using protected groups. The preparation of specific quinolinone analogues of a pyridone of this invention are exemplified as in Example 1 through Example 16.

Scheme 1: General Quinolone Synthesis-I
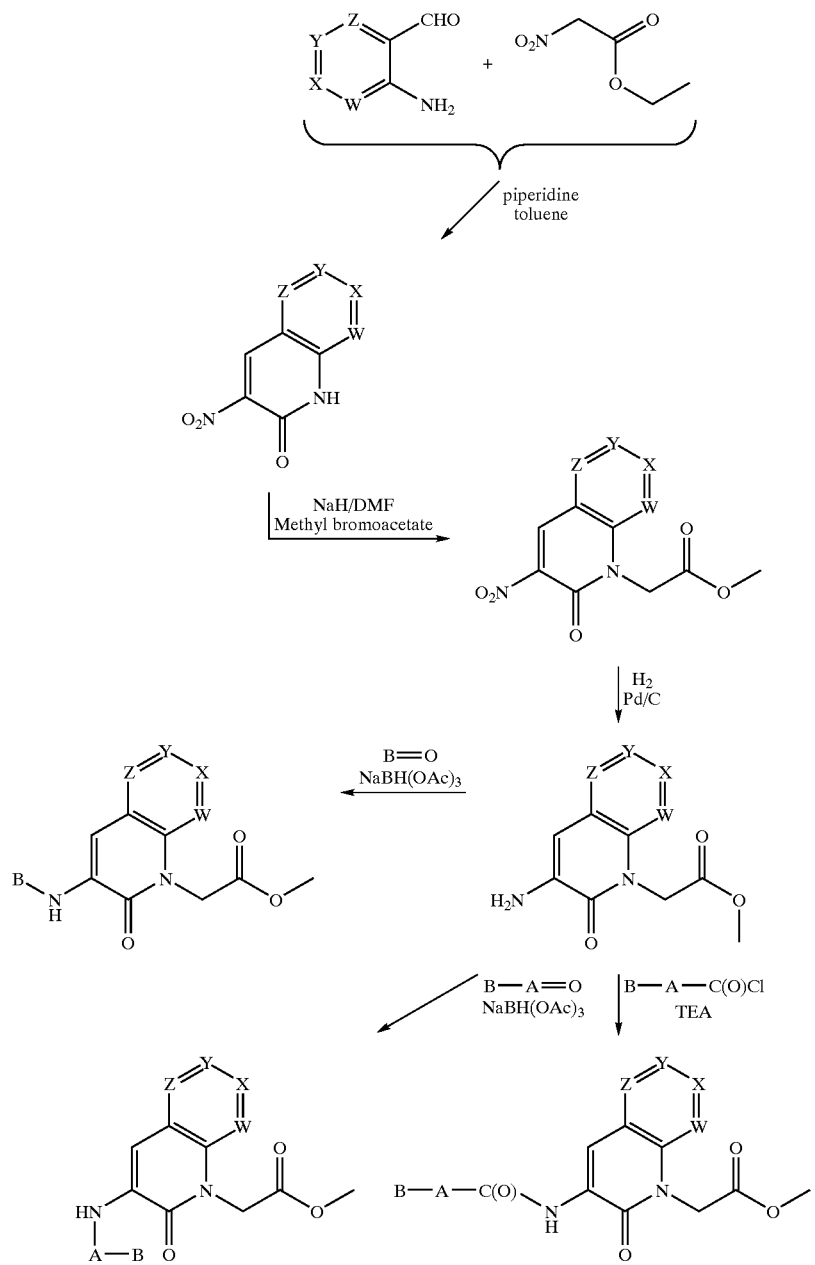
Scheme 2: General Quinolone Synthesis-1 (Concluded)
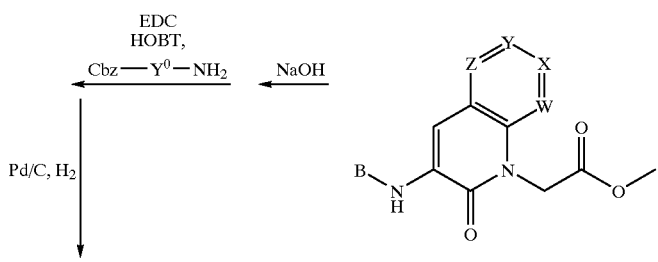

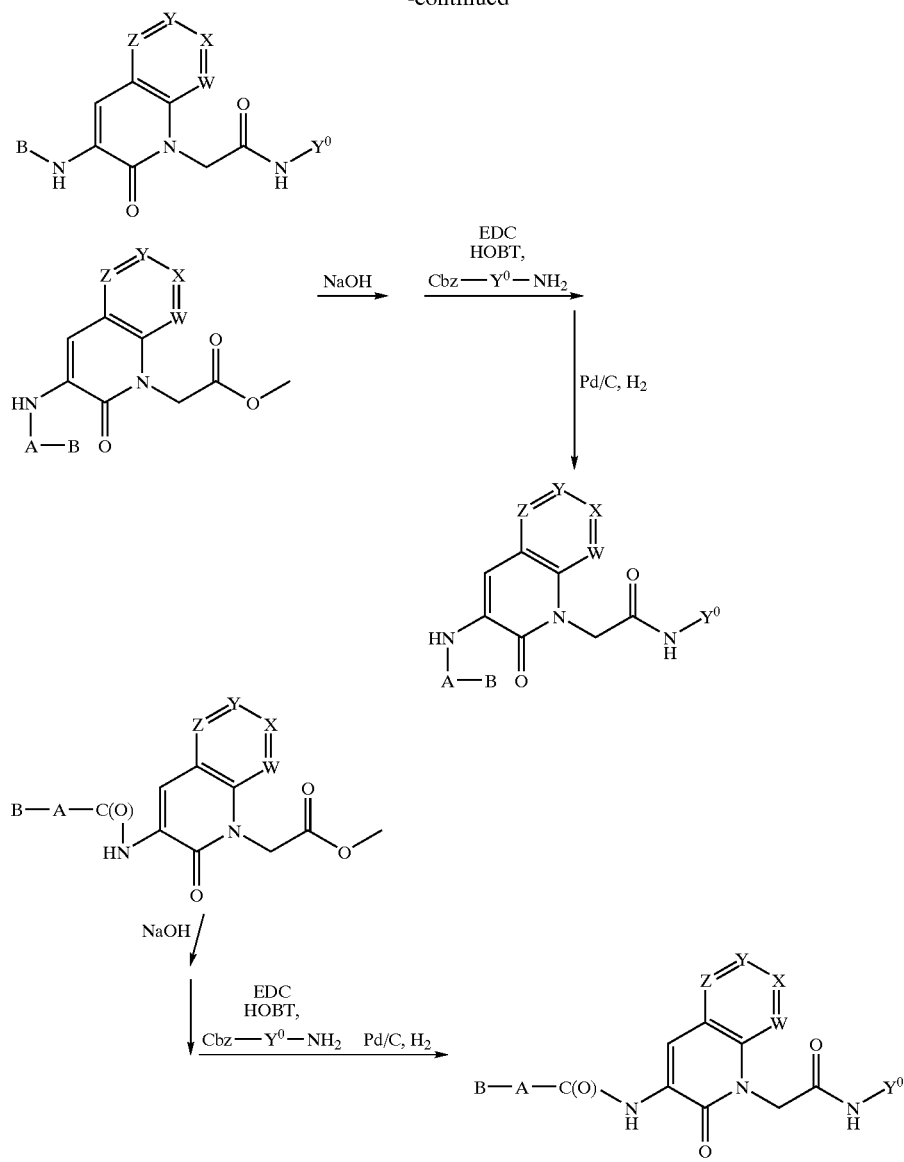

Example 1

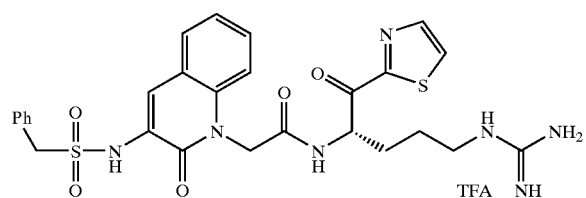

EX-1A)

3-Nitro-1H-Quinolin-2-One (2.35 g, 1237 mmole) in 50 ml anhydrous DMF was mixed with NaH 60% in mineral oil (0.59 g, 14.87 g), and the mixture was stirred for five minutes. To this mixture, 2-methyl-2-bromoacetate (2.27 g, 14.84 mmole) was added dropwise. After stirring the reaction mixture for 2 hours at 20° C., DMF was removed via vacuum rotary evaporation to lead to a yellow oil residue. The residue was triturated in water to yield a yellow solid that was washed with water and hexane. The yellow solid was re-crystallized in ethylacetate to yield a yellow needle crystal solid (1.38 g) as the expected product, methyl-(3-nitro-2-oxo-2H-quinolin-1-yl)acetate. More product (1.20 g) was obtained from the mother liquor via silica gel flash chromatography to separate it from the O-alkylated side product (0.334 g). The desired product (EX-1A) yield was 80%. HPLC-MS (0 to 95% AcCN/6 min @ 1.0 mL/Min @ 254 min @ 50° C.): retention time 2.48 min, M+H$^+$=2632 for formula $C_{12}H_{10}N_2O_5$. $^1$H NMR (400 MHz, CDCl$_3$): δ 3.80 (s, 3H), 5.17 (s, 2H), 7.19 (d, J=8.4 Hz, 1H), 7.40 (t, J=7.6 Hz, 1H), 7.76 (t, J=7.6 Hz, 1H), 7.78 (d, J=8.4 Hz, 1H), 8.61 (s, 1H). $^{13}$C NMR (101 MHz, CDCl$_3$): δ 44.2. 52.9, 14.2, 117.1, 124.0. 131.7, 134.8, 137.9, 140.6, 154.0, 167.6.

EX-1B)

Compound EX-1A (251 g, 9.58 mmole) was mixed with 10% Pd on activated carbon (0.51 g, 0.48 mmole) in 150 ml methanol. The mixture was stirred under H$_2$ that was introduced through a rubber balloon for 2 hours. The reaction mixture was filtered, and the methanol was removed to yield a white crystalline solid (2.06 g, y=93%) as methyl-(3- amino-2-oxo-2H-quinolin-1-yl)acetate (3). HPLC-MS (0 to 95% AcCN/6 min @ 1.0 mL/Min @ 254 nm @ 50° C.): retention time 2.12 min, M+H$^+$=233.1 for formula $C_{12}H_{12}N_2O_3$. Compound 3 (2.04 g, 8.79 mmole) and pyridine (3.55 ml, 43.95 mmoles) were dissolved in 200 ml acetonitrile. This mixture was cooled down to −10° C. with a water-acetone-dry ice mixture bath. To this mixture, a-tolunesulfonyl chloride (4.19 g, 21.98 mmoles) dissolved in 10 ml acetonitrile was added dropwise quickly. The reaction mixture was stirred for 2.5 hours from −10° C. to 0° C. During the reaction, the product as a white solid precipitated from the solution. The pure product, methyl-(3-benzylsulfonylamido-2-oxo-2H-quinotin-1-yl)acetate (EX-1B) (2.92 g) was obtained by filtration and washing it with acetonitrile. More product (0.34 g) was obtained by working up the filtrate and subjecting it to a Biotage-40 silica gel column chromatography using 25% ethylacetate in hexane as the elute. HPLC-MS (0 to 95% AcCN/6 min @ 1.0 mL/Min @ 254 nm @ 50° C.): retention time 3.52 min, M+Na$^+$=408.9 for formula $C_{19}H_{18}N_2O_5SNa$. $^1$H NMR (400 MHz, CDCl$_3$): δ 3.81 (s, 3H), 4.42 (s, 2H), 5.14 (s, 2H), 7.09 (d, J=8.8 Hz, 1H), 7.27 (m, 5H), 7.48 (t, J=7.6 Hz, 2H), 7.61 (d, J=10 Hz, 1H), 8.61 (s, 1H). $^{13}$C NMR (101 MHz, CDCl$_3$): δ 44.5, 52.8, 58.5, 113.3, 119.5, 120.4, 123.5, 127.2, 127.8, 128.7, 128.8, 129.0, 129.2, 130.8, 135.2, 157.3, 167.9.

EX-1C)

Compound EX-1B (3.19 g, 8.26 mmole) was dissolved in 50 ml THF, 30 ml MeOH and 50 ml 1 M LiOH. The mixture was stirred at 20° C. for one hour. The mixture was concentrated to remove the organic solvents. The remaining aqueous solution was acidified to pH=1 with 1M HCl, and a solid precipitated from the solution. The solid was purified by filtration, washing with 1M HCl and water, and drying via vacuum to give a white solid as the pure product (3-benzylsulfonylamino-2-oxo-2H-quinolin-1-yl)acetic acid (EX-1C) (2.98 g, yield of 97%). HPLC-MS (0 to 95% AcCN/6 min @ 1.0 mL/Min @ 254 nm @ 50° C.): retention time 3.09 min, M+Na$^+$=395.2 for formula $C_{18}H_{16}N_2O_5Na$. $^1$H NMR (400 MHz, CDCl$_3$): δ 4.54 (s, 2H), 5.13 (s, 2H), 7.15 (t, J=87.2 Hz, 1H). 7.23 (m, 3H), 7.33 (m, 3H), 7.50 (t, J=7.6 Hz, 2H), 7.59 (s, 1H).

EX-1D)

Compound EX-1C (0.209 g, 0.56 mmol), EDC (0.140 g, 0.73 mmol) and HOBt (0.112 g, 0.73 mmol) were mixed in 1.5 ml DMF, and the mixture was stirred at 20° C. for 10 minutes. To this mixture was added the premixed solution of (4S)-(9Cl)-N[[[4-amino-5-hydroxy-5-(2-thiazolyl)pentyl] amino]iminomethyl]-4-methoxy-2,3,6-trimethylbenzenesulfonamide HCl salt (0.387 g, 0.73 mmol), diisopropylethylamine (0.65 ml, 3.93 mmol) in 1.5 ml DMF. The combined reaction mixture was stirred for 45 minutes at 20° C. The reaction mixture was partitioned between ethylacetate and saturated ammonium chloride aqueous solution. The organic phase was washed with saturated aqueous potassium carbonate and ammonium chloride solution, dried over Na$_2$SO$_4$. After removing the ethylacetate, the residue was subjected to a Biotage silica gel column chromatography to yield a white solid as the product N-[2(S)-1(R,S)-2-[1-hydroxy-1-(2-thiazolyl)]-5-[[(4-methoxy-2,3,6-trimethyl)sulfonylamino]-iminomethyl] aminopentyl]-2-[3-benzylsulfonylamino-2-oxo-2H-quinolin-1-ylacetamide (EX-1D) (0.347 g, y=76%). HPLC-MS (0 to 95% AcCN/6 min @ 1.0 mL/Min @ 254 nm @ 50° C.): retention time 3.75 min, M+H$^+$=810.3 for formula $C_{37}H_{43}N_7O_8S_3$. Since the compound is a mixture of two diastereomers, the $^1$H NMR and $^{13}$C NMR was complex.

EX-1E)

Compound EX-1D (0.32 g, 0.395 mmol) was mixed with 1,3-dihydro-1-hydroxy-3,3-bis(trifluoromethyl)-1-oxide-1,2-benziodoxole (0.238 g, 0.593 mmole) in 5 ml acetonitrile. The mixture was stirred at 20° C. for 2 hours. It was then mixed with 30 ml 1M NaHSO$_3$ aqueous solution. The combined solution was extracted with ethylacetate, and the organic phase was washed with saturated NaHCO$_3$ aqueous solution and dried over Na$_2$SO$_4$. After removing the ethylacetate, the remaining residue was subjected to a silica gel flash column chromatography using 30% ethylacetate in hexane as elute to yield a white solid as the product N-[2(S)-2-[1-Oxo-1-(2-thiazolyl)]-5-[[[(4-methoxy-2,3,6-trimethyl)sulfonylamino]iminomethyl]amino]pentyl]-2-[3-benzylsulfonylamino-2-oxo-2H-quinolin-1-yl]acetamide (EX-1E) (0.296 g, 93%). HPLC-MS (0 to 95% AcCN/6 min @ 1.0 mL/Min @ 254 nm @ 50° C.): retention time 4.07 min, M+H$^+$=808.2 for formula $C_{37}H_{41}N_7O_8S_3$. $^1$H NMR (400 MHz, acetone-d$_6$): d 1.71 (b, 4H), 2.07 (s, 3H), 2.59 (s, 3H), 2.64 (s, 3H), 3.24 (m, 2H), 3.80 (s, 3H), 4.62 (s, 2H), 5.17 (d, J=−16.4 Hz, 1H), 5.22(d, J=16.4 Hz, 1H), 5.62 (m, 1H), 6.47 (b, 2H), 6.64(s, 1H), 7.24 (m, 4H), 7.36 (m, 3H), 7.44 (m, 2H), 7.59 (t, J=7.2 Hz, 2H), 7.95 (b, 1H), 8.08 (m, 3H). $^{13}$C NMR (101 MHz, CDCl$_3$): d 12.0, 15.6, 18.6, 24.2, 41.1, 46.6, 55.8, 55.9, 58.5, 66.1, 112.3, 120.3, 121.2, 123.8, 124.8, 128.5, 129.1, 129.2, 129.3, 129.6, 129.7, 129.9, 123.0, 131.9, 135.8, 136.7, 137.0, 139.0, 146.1, 157.4, 158.0, 158.8, 165.6, 167.7, 192.0.

Compound EX-1E (0.240 g, 0.296 mmol) was treated with thioanisole (0.220 g, 1.78 mmol) and 8 ml trifluoroacetic acid for 5 hours. After removing the TFA, the residue was triturated in diethylether twice and ethylacetate once to give a white amorphous solid as the product N-[2(S)-2-[1-Oxo-1-(2-thiazolyl)]-5-[[(amino)iminomethyl]]amino] pentyl]-2-[3-benzylsulfonylamino-2-oxo-2H-quinolin-1-yl] acetamide trifluoroacetic acid salt (0.183 g, yield of 87%). HPLC-MS (0 to 95% AcCN/6 min @ 1.0 mL/Min @ 254 nm @ 50° C.): retention time 3.07 min, M+H$^+$=596.2 for formula $C_{27}H_{29}N_7O_5S_2$. $^1$H NMR (400 MHz, DMSO-d$_6$): d 1.58 (bm, 2H), 1.67 (bm, 1H), 1.90 (b, 1H), 3.10 (bm, 2H), 4.60 (s, 2H), 3.80 (s, 3H), 4.62 (s, 2H), 5.01 (d, J=−17.2 Hz, 1H), 5.11 (d, J=−17.2 Hz, 1H), 5.38 (m, 1H), 6.80–7.70 (m, 15H), 8.14(s, 1H), 8.23 (s, 1H), 8.88 (b, 1H), 9.99 (d, J=8.0 Hz, 1H). $^{13}$C NMR (101 MHz, DMSO-d$_6$): d 25.3, 28.0, 44.9, 48.6, 54.4, 58.0, 114.2, 119.7, 121.9, 124.8, 126.1, 128.2, 128.3, 128.7, 131.0, 135.9, 137.1, 138.7, 144.7, 145.4, 156.6, 157.4, 164.4, 166.8, 191.4.

Example 2

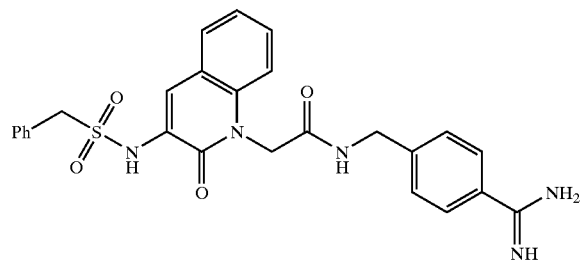

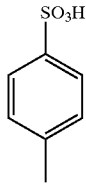

EX-2A)

3-Benzylsulfonylamino-2-oxo-2H-quinolin-1-yl)acetic acid was coupled with benzyl-[[(4-aminomethylphenyl)iminomethyl]amino]carbamate hydrogen chloride salt using EDC, HOBt as coupling agents in the presence of DIEA in DMF. Work up procedure gave a white amorphous solid as the product, N-[[4-[(benzylcarbonylamino)iminomethyl]phenyl]methyl]-2-[3-benzylsulfonylamino-2-oxo-2H-quinolin-1-yl]acetamide. HPLC-MS (0 to 95% AcCN/6 min @ 1.0 mL/Min @ 254 nm @ 50° C.): retention time 3.38 min, M+H+=638.3 for formula $C_{34}H_{31}N_5O_6S$. $^1$H NMR (400 MHz, CDCl$_3$): d 4.38 (s, 2H), 4.50 (d, J=6.0 Hz, 2H), 4.92 (s, 2H), 5.14 (s, 2H), 7.06 (t, J=7.2 Hz, 1H), 7.13 (t, J=7.6 Hz, 2H), 7.15–7.24 (m, 6H), 7.30–7.40 (m, 6H), 7.45 (m, 3H), 7.52 (m, 1H), 7.57 (d, J=8.4 Hz, 2H), 8.65(b, 1H), 9.09 (b, 1H).

Compound EX-2A (0.118 g, 0.185 mmol), p-toluenesulfonic acid mono hydrate (0.035 g, 0.185 mmol) and 10% Pd on activated carbon (0.029 g, 0.018 mmol) were mixed with 5 ml methanol. The mixture was stirred for 2 hours under an atmosphere of hydrogen that was introduced through a rubber balloon. After filtering off the catalyst and removing the methanol, the remaining residue was recrystallized in a solvent of 2:1 ether to methanol to yield a white amorphous solid as the product, N-[[4-[(amino)iminomethyl]phenyl]methyl]-2-[3-benzylsulfonyl-amino-2-oxo-2H-quinolin-1-yl]acetamide p-toluenesulfonic acid salt, (0.080 g, yield=64%). HPLC-MS (0 to 95% AcCN/6 min @ 1.0 mL/Min @ 254 nm @ 50° C.): retention time 2.81 min, M+H+=504.5 for formula $C_{26}H_{25}N_5O_4S$. $^1$H NMR (400 MHz, CD$_3$OD): d 2.36 (s, 3H), 4.52 (s, 2H), 4.57 (s, 2H), 5.15 (s, 2H), 7.18–7.32 (m, 7H), 7.36 (t, J=7.2 Hz, 2H), 7.48–7.55 (m, 4H), 7.59 (s, 1H), 7.70 (d, J=8.0 Hz, 2H), 7.74 (d, J=8.4 Hz, 2H).

Example 3

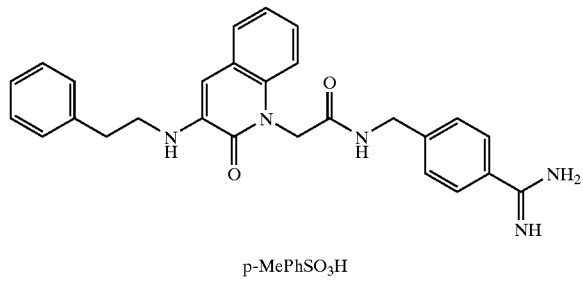

p-MePhSO₃H

EX-3A)

Methyl 2-[3-amino-2-oxo-2H-quinolin-1-yl]acetate, (9.1 g, 39.2 mmol) was mixed with Boc anhydride (9.41 g 43.1 mmol), triethylamine (6 ml, 43.1 mmol) and DMAP (50 mg, 0.4 mmol) in 200 ml DCM. The reaction mixture was stirred at 20° C. for 14 hours. The reaction solution was washed with 1M citric acid solution twice, saturated sodium bicarbonate solution three times, saturated ammonium chloride once and it was dried over anhydrous MgSO$_4$. After filtration and removing the solvent, the residue was treated with methanol. A white solid was precipitated. Filtration and washing with methanol, the pure product, EX-3A, was obtained as a white powder (9.90 g, 87%). HPLC-MS (0 to 95% AcCN/6 min @ 1.0 mL/Min @ 254 nm @ 50° C.): retention time 2.85 min, M+H+=291.1 for formula $C_{14}H_{15}N_2O_3$. $^1$H NMR (400 MHz, Methanol-d$_4$): d 3.76 (s, 3H), 3.82 (s, 3H), 5.15 (s, 2H), 7.09 (d, J=8.4 Hz, 1H), 7.26 (t, J=7.6 Hz, 1H), 7.43 (t, J=7.6 Hz, 2H), 7.61 (d, J=7.6 Hz, 1H), 7.96 (s, 1H), 8.39 (s, 1H). $^{13}$C NMR (101 MHz, Methanol-d$_4$): d (ppm) 4.44, 52.5, 52.6, 113.1, 118.9, 21.0, 123.3, 127.4, 128.4, 128.5, 134.5, 153.9, 157.6, 168.1.

EX-3B)

Compound EX-3A (1.09 g, 3.75 mmol) was mixed with KOH (5.2 g, 92.8 mmol) in 30 ml water and 30 ml methanol. After refluing for three hours, the reaction solution was concentrated to 10 ml and acidified with concentrated HCl to pH=2. After cooling down to 0° C., the product was filtered out, washed with water and dried via vacuum, A yellow powder acid was obtained as the pure product (0.733 g, y=90%). HPLC-MS (0 to 95% AcCN/6 min @ 1.0 mL/Min @ 254 nm @ 50° C.): retention time 1.60 min, M+H+=219.1 for formula $C_{11}H_{11}N_2O_3$.

EX-3C)

Compound EX-3B (0.296 g, 1.16 mmol) was treated with phenylacetaldehyde (0.21 g, 1.74 mmol) in 15 ml methanol for 10 minutes. To this mixture was added sodium cyanoborohydride (0.08 g, 1.28 mmol). After two hours, the reaction was completed. Methanol was removed under reduced pressure and the residue was mixed with water. The product 2-[3-(2-phenylethylamino)-2-oxo-2H-quinolin-1-yl]acetic acid (EX-3C) was obtained after filtration and washed with water as a white powder (0.225 g, 60%). HPLC-MS (0 to 95% AcCN/6 min @ 1.0 mL/Min @ 254 nm @ 50° C.): retention time 3.55 min, M+H+=323.2 for formula $C_{19}H_{19}N_2O_3$. $^1$H NMR (400 MHz, Methanol-d$_4$): d 2.97 (t, J=7.2 Hz, 2H), 3.45 (t, J=7.2 Hz, 2H), 5.02 (s, 2H), 6.65 (s, 1H), 7.13–7.29 (m, 8H), 7.46 (d, J=8.0 Hz, 1H). $^{13}$C NMR (101 MHz, Methanol-d$_4$): d (ppm) 35.9, 455, 46.6, 105.7, 115.1, 123.9, 124.5, 125.9, 127.0, 127.4, 129.6, 129.8, 133.9, 137.8, 140.8, 159.9, 173.1.

EX-3D)

Compound EX-3D was synthesized in same way as described for compound EX-2A. It is a white powder. HPLC-MS (0 to 95% AcCN/6 min @ 1.0 mL/Min @ 254 nm @ 50° C.): retention time 3.65 min, M+H+=588.6 for formula $C_{35}H_{34}N_5O_4$. $^1$H NMR (400 MHz, Methanol-d$_4$): d 2.95 (t, J=7.2 Hz, 2H), 3.43 (t, J=7.2 Hz, 2H), 4.46 (s, 2H), 5.09 (s, 2H), 537 (s, 2H), 6.64 (s, 1H), 7.13–7.29 (m, 9H), 7.38–7.41 (m, 3H), 7.47 (m, 4H), 7.70 (d, J=8.4 Hz, 2H). $^{13}$C NMR (101 MHz, Methanol-d$_4$): d (ppm) 35.8, 43.7, 45.4, 46.9, 70.6, 105.8, 114.9, 124.2, 124.6, 126.0, 127.2, 127.4, 129.1, 129.6, 129.7, 129.8, 129.9, 130.0, 133.8, 137.8, 140.7, 160.2, 170.3.

The product of Example 3 was synthesized in same way as described for compound of Example 2 as a p-toluenesulfonic acid salt and an amorphous solid. HPLC-MS (0 to 95% AcCN/6 min @ 1.0 mL/Min @ 254 nm @ 50° C.): retention time 3.18 min, M+H+=454.1 for formula $C_{27}H_{28}N_5O_2$. $^1$H NMR (400 MHz, Methanol-d$_4$): d 2.32 (s, 3H), 3.03 (t, J=7.2 Hz, 2H), 3.56 (t, J=7.2 Hz, 2H), 4.48 (s, 2H), 5.14 (s, 2H), 7.19 (d, J=8.0 Hz, 4H), 7.26–7.34 (m, 6H), 7.48 (d, J=8.0 Hz, 2H), 7.55 (s, 1H), 7.64 (d, J=7.6 Hz, 1H), 7.69 (t, J=8 Hz, 4H), 8.72 (s, 2H), 9.18 (s, 2H). $^{13}$C NMR (101 MHz, Methanol-d$_4$): d (ppm) 21.3, 34.3, 43.7, 46.8, 59.6, 115.4, 122.0, 124.6, 126.9, 127.8, 128.2, 128.3, 129.0, 129.2, 129.5, 129.7, 129.8, 129.9, 1303, 131.4, 137.4, 138.9, 141.8, 146.7, 159.5, 168.2, 168.3, 169.7.

Example 4

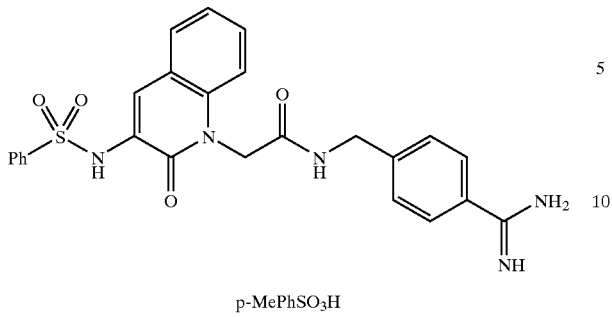

p-MePhSO₃H

Example 5

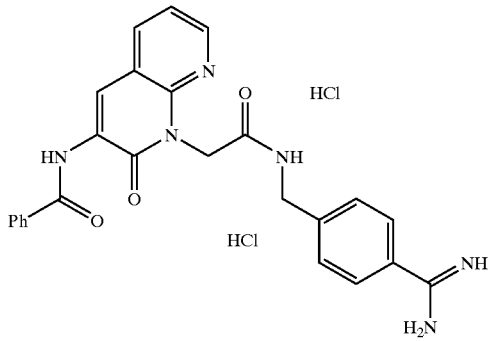

EX-4A)

2-[3-Amino-2-oxo-2H-quinolin-1-yl]acetic acid, (0.206 g, 0.81 mmol) was treated with benzenesulfonyl chloride (0.172 g, 0.97 mmol) in pyridine for one hour. After removing the pyridine, the residue was recrystallized in acetone to yield a white crystal solid as the product, 2-[3-benzenesulfonylamino-2-oxo-2H-quinolin-1-yl]acetic acid, (EX-4A)(0.117 g, y=41%). HPLC-MS (0 to 95% AcCN/6 min @ 1.0 mL/Min @ 254 nm @ 50° C.): retention time 2.85 min, M+H$^+$=359.2 for formula $C_{17}H_{15}N_2O_2S$. $^1$H NMR (400 MHz, Acetone-d$_6$): d 5.12 (s, 2H), 7.28 (t, J=7.2 Hz, 1H), 7.36 (d, J=8.8 Hz, 1H), 7.48–7.63 (m, 4H), 7.75 (dd, J=8, 1.6 Hz, 1H), 7.74 (s, 1H), 8.00–8.03 (m, 2H). $^{13}$C NMR (101 MHz, Acetone-d$_6$): d (ppm) 44.8, 115.0, 120.8, 120.9, 123.9, 127.8, 128.1, 129.4, 129.9, 130.1, 134.2, 136.7, 140.4, 158.2, 169.1.

EX-4B)

Compound EX-4A was synthesized in same way as described for compound EX-2A giving a white powder. HPLC-MS (0 to 95% AcCN/6 min @ 1.0 mL/Min @ 254 nm @ 50° C.): retention time 3.23 min, M+H$^+$=624.2 for formula $C_{33}H_{30}N_5O_6S$. $^1$H NMR (400 MHz, Methanol-d$_4$): d 4.45 (s, 2H), 5.06 (s, 2H), 5.38 (s, 2H), 7.24–7.60 (m, 14H), 7.71 (d, J=8.0 Hz, 2H), 7.84 (s, 1H), 7.94 (d, J=7.2 Hz, 2H). $^{13}$C NMR (101 MHz, Methanol-d$_4$): d (ppm) 43.7, 47.0, 70.7, 115.3, 121.7, 122.5, 124.5, 127.3, 128.4, 129.1, 129.6, 129.7, 129.9, 130.0, 130.1, 130.2, 130.3, 134.4, 135.8, 137.2, 140.8, 147.7, 154.6, 159.3, 167.9, 169.8.

Compound of this example was synthesized in same way as described for compound Example 2. It is an amorphous off-white solid and a p-toluenesulfonic acid salt. HPLC-MS (5 to 95% AcCN/6 min @ 1.0 mL/Min @ 254 nm @ 50° C.): retention time 2.02 min, M+H$^+$=490.1 for formula $C_{25}H_{24}N_5O_4S$. $^1$H NMR (400 MHz, Methanol-d$_4$): d 2.34 (s, 3H), 4.46 (s, 2H), 5.06 (s, 2H), 7.20 (d, J=8.0 Hz, 1H), 7.24–7.29 (m, 2H), 7.46–7.51 (m, 6H), 7.55 (d, J=7.2 Hz, 1H), 7.62 (d, J=8.0 Hz, 1H), 7.71 (m, 4H), 7.86 (s, 1H), 7.95 (d, J=8.0 Hz, 2H). $^{13}$C NMR (101 MHz, Methanol-d$_4$): d (ppm) 21.3, 43.6, 46.9, 115.1, 121.6, 122.4, 124.4, 126.8, 127.9, 128.2, 128.9, 129.0, 129.5, 129.7, 130.1, 130.2, 134.3, 137.0, 140.6, 146.6, 159.2, 169.5, 184.2.

EX-5A)

A solution of 2-amino pyridine (20.42 g, 217.0 mmol) in dichloromethane 500 mL was cooled to 0° C. and treated with triethyl amine (36.29 mL, 260.4 mmol) and pivaloyl chloride (28.06 ml, 227.8 mmol). After 15 minutes, the reaction mixture was allowed to warm to room temperature and stir overnight. The reaction mixture was poured onto ice, and the organic layer was washed with saturated NaHCO$_3$ (aq), and dried over Na$_2$SO$_4$. The volatile components were removed, and a brown oil was isolated. Crystallization with hexanes afforded 31 g of N-(pyrid-2-yl)-2,2-dimethylacetanide (EX-5A)as white crystals in 80% yield. Reference: Turner, J. A. *J. Org. Chem.* 1983, 48, 3401.

EX-5B)

A solution of EX-5A (2.00 g, 11.23 mmol) in THF (115 mL) at −78° C. was treated with n-BuLi (14.1 mL, 28.10 mmol of a 2.0 M solution in hexanes). The reaction mixture was allowed to warm to 0° C. and stir for 2 h. The reaction mixture was again cooled to −78° C., and the mixture was quenched with DMF (2.18 mL, 28.10 mmol). The reaction mixture was allowed to warm to room temperature and to stir overnight. The reaction mixture was poured into a slurry of ice and 6N HCl, and the acidified mixture was stirred for 15 minutes. The organic layer was separated (discard), and the aqueous layer was neutralized with K$_2$CO$_3$ and extracted with ether (3×100 mL). The combined organic layers were washed with water, brine and dried over MgSO$_4$. After filtration and evaporation of the volafiles, a yellow oil was isolated which solidified upon standing. 1.23 g (53%) of EX-5B product was isolated. Reference: Turner, J. A. *J. Org. Chem.* 1990, 55, 4744.

EX-5C)

A mixture of EX-5B (0.62 g, 3.01 mmol) and 3N HCl (30 mL) was refluxed overnight. After the reaction mixture was allowed to cool to room temperature, it was washed with ether (2×50 mL). The organic layer was discarded. The aqueous layer was neutralized with K$_2$CO$_3$, and extracted with ether (4×50 mL). The combined ether layers were dried over K$_2$CO$_3$, filtered, and concentrated to afford 2-aminopyridinecarboxaldehyde (EX-5C) as a yellow oil (0.36 g) which solidified upon standing. The crude material was used with any further purification. Reference: Moormann, A. E.; Yen, C. H.; Yu, S. *Syn. Commun.* 1987, 17, 1695.

EX-5D)

A mixture of hippuric acid (0.54 g, 3.01 mmol) and acetic anhydride (30 mL) was heated to 80° C. After 2 h, the reaction mixture was homogeneous. The hot reaction mixture was treated with a solution of EX-5C (0.37 g, 3.01 mmol) in acetic anhydride. After stirring the reaction mixture for an additional 16 h, the reaction mixture became heterogeneous. The volatile components were removed in vacuo, and the precipitate was filtered. The filter cake was washed with ether (3×30 mL), and 0.36 g of 3-benzamido-2-oxo-2H-1,8-naphthyridine (EX-5D) was isolated as tan colored powder in 45% yield: $^1$H NMR (300 MHz, d-DMSO) d 12.77 (s, 1H), 9.47 (s, 1H), 8.72 (s, 1H), 8.45 (d, J=3.42 Hz, 1H), 8.21–8.18 (m, 1H), 7.95 (d, J=7.6 Hz, 2H), 7.66–7.54 (m, 3H), 7.28 (dd, J$_1$=4.6 Hz, J$_2$=4.8 Hz, 1H); $^{13}$C NMR (75 MHz, CDCl$_3$) d 165.8, 159.4, 149.2, 146.6, 136.6, 134.3, 133.0, 130.3, 129.61 (2C), 129.58, 127.9, 120.2, 119.8, 115.7; HRMS (EI) calcd for C$_{15}$H$_{11}$N$_3$O$_2$ 266.0930, found 266.0939.

EX-5E)

A solution of EX-5D (0.072 g, 0.271 mmol) in DMF (5 mL) was cooled to 0° C., and NaH (60% dispersion in mineral oil, 0.013 g, 0.325 mmol) was slowly added. After five minutes, methyl bromoacetate was added dropwise via syringe. The reaction mixture was allowed to warm to room temperature, and it was stirred until no starting material remained by TLC. DMF was removed in vacuo which afforded a yellow residue. The residue was triturated in water and washed with water and hexanes to afford 0.062 g of methyl 2-[3-benzamido-2-oxo-2H-1,8-naphthyridin-1-yl] acetate (EX-5E) in 68% yield: $^1$H NMR (400 MHz, CDCl$_3$) d 9.30 (s, 1H), 8.88 (s, 1H), 8.45 (d, J=4.6 Hz, 1H), 7.95–7.91 (m, 3H), 7.56–7.46 (m, 3H), 7.23–7.20 (m, 1H), 5.37 (s, 2H), 3.74 (s, 3H); $^{13}$C NMR (100 MHz, CDCl$_3$) d 168.8, 166.1, 159.0, 148.0, 145.5, 136.5, 134.0, 132.6, 129.12, 129.11, 129.08, 128.8, 127.4, 119.8, 119.0, 116.7, 52.7, 43.2; HRMS (EI) calcd for C$_{18}$H$_{15}$N$_3$O$_4$ 338.1156, found 338.1141.

EX-5F)

A solution of EX-5E (0.053 g, 0.157 mmol) in THF and methanol (3:2, 5 mL) was treated with 1.0 M LiOH (aq). The reaction mixture was stirred over night. The mixture was concentrated to remove the volatile components. The resulting aqueous solution was acidified with 1N HCl, and a solid precipitated from the solution. After filtration, the filter cake was washed with 1N HCl and water to afford 0.038 g of 2-[3-benzamido-2-oxo-2H-1,8-naphthyridin-1-yl]acetic acid (EX-5F) as white solid in 74% yield: $^1$H NMR (400 MHz, d-DMSO) d 13.10 (br s, 1H), 9.53 (s, 1H), 8.78 (s, 1H), 8.51–8.50 (m, 1H), 8.26 (d, J=7.8 Hz, 1H), 7.93 (d, J=8.1 Hz, 2H), 7.62–7.51 (m, 3H), 7.36–7.32 (m, 1H), 5.14 (s, 2H); $^{13}$C NMR (100 MHz, d-DMSO) d 169.9, 166.0, 158.7, 148.8, 145.9, 137.5, 134.2, 133.0, 129.5 (2C), 128.8, 128.0 (2C), 120.4, 120.2, 116.2, 43.5; HRMS (EI) calcd for C$_{17}$H$_{13}$N$_3$O$_4$ 324.1004, found 324.098.

EX-5G)

A solution of EX-5F (0.099 g, 0.30 mmol) in 3 mL of DMF was treated with N-hydroxybenzotriazole (0.054 g, 0.40 mmol), and 1-[3-(dimethylamino)propyl]-3-ethylcarbodiimide hydrochloride (0.076 g, 0.40 mmol), and N,N-diisopropylethylamine (0.37 mL, 2.14 mmol). The resulting mixture was allowed to stir for 15 minutes at room temperature. The reaction mixture was then treated with 4-(N-Cbz-amidino)benzylamine (0.127 g, 0.40 mmol) as a solution in DMF (3 mL). The resulting reaction mixture was allowed to stir for 18 hours. The reaction mixture was partitioned between ethyl acetate and a saturated NH$_4$Cl(aq) solution. The separated organic layer was washed with saturated K$_2$CO$_3$ (aq), saturated NH$_4$Cl (aq), and brine. The organic solution was dried (Na$_2$SO$_4$), filtered and concentrated. (EX-5G) was isolated as a white solid, and the crude product was used in the next step without further purification: HRMS (EI) calcd for C$_{33}$H$_{28}$N$_6$O$_5$ 589.2178, found 589.2199.

A solution of Cbz-amidine (EX-5G) (0.090 g, 0.15 mmol) in 6 mL of methanol, and 1 mL of 4 N HCl in dioxane was treated with 25 mg of 10% Pd/C in one portion. The resulting reactin mixture was stirred under hydrogen gas (25 psi) for 18 hours. After filtration of the reaction mixture through a pad of Celite, the solvent was removed under reduced pressure. Slow addition of 1 M HCl precipitated pure product of the invention as a white solid: 1H NMR (400 MHz, d-DMSO) 9.52 (s, 1H), 9.24 (s, 2H), 8.91–8.83 (m, 2H), 8.77 (s, 1H), 8.53–8.52 (m, 1H), 8.27 (d, J=7.5 Hz, 1H), 7.93 (d, J=7.5 Hz, 2H), 7.73 (d, J=8.3 Hz, 2H), 7.63–7.61 (m, 1H), 7.56–7.52 (m, 2H), 7.43 (d, J=8.1 Hz, 2H), 7.37–7.34 (m, 1H), 5.17 (s, 2H), 4.35 (d, J=5.9 Hz, 2H); $^{13}$C NMR (100 MHz, d-DMSO) d 167.7, 166.0, 165.9, 159.0, 148.6, 146.4, 146.2, 137.4, 134.2, 133.1, 129.6, 128.9, 128.8, 127.93 (2C), 127.88 (2C), 127.0, 120.21, 120.16, 1165, 72.9, 60.9, 44.8, 42.4; HRMS (EI) calcd for C$_{25}$H$_{22}$N$_6$O$_3$ 455.1832, found 455.1840.

Additional substituted N-[Substituted]-(3-benzylsulfonylamino-2-oxo-2H-quinolin-1-yl)acetamides can be prepared by one skilled in the art using methods similar to those above. These acetamides as shown in Example Table 1.

EXAMPLE TABLE 1

N-[Substituted]-(3-benzylsulfonylamino-2-oxo-2H-quinolin-1-yl)acetamides.

| Ex. No. | Y$^0$ |
|---|---|
| 6 | 2-[4-Aminophenyl]ethyl |
| 7 | 4-aminobutyl |
| 8 | 5-aminopentyl |
| 9 | 6-(N,N-dimethylamino)hexyl |
| 10 | 4-Aminomethylbenzyl |
| 11 | 3-Aminomethylbenzyl |
| 12 | 3-[Imidazo-1-yl]propyl |
| 13 | 2-[Imidazo-5-yl]ethyl |
| 14 | 2-[Pyrid-3-yl]ethyl |
| 15 | 3-[N-Methylpiperidin-4-yl]propyl |
| 16 | 4-Aminobenzyl |

The pyridone analogs of the present invention have the general structure as shown in FIG. 2.

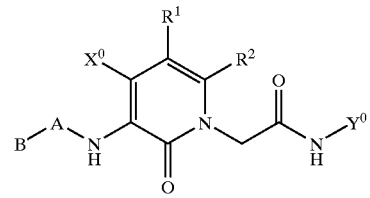

FIG. 2
General Structure of Pyridone Analogues

A general synthetic route is illustrated in Scheme 3 wherein substituents are as defined herein. These compounds are exemplified in Examples 17 through 23.

Scheme 3: General Synthesis of Pyridones

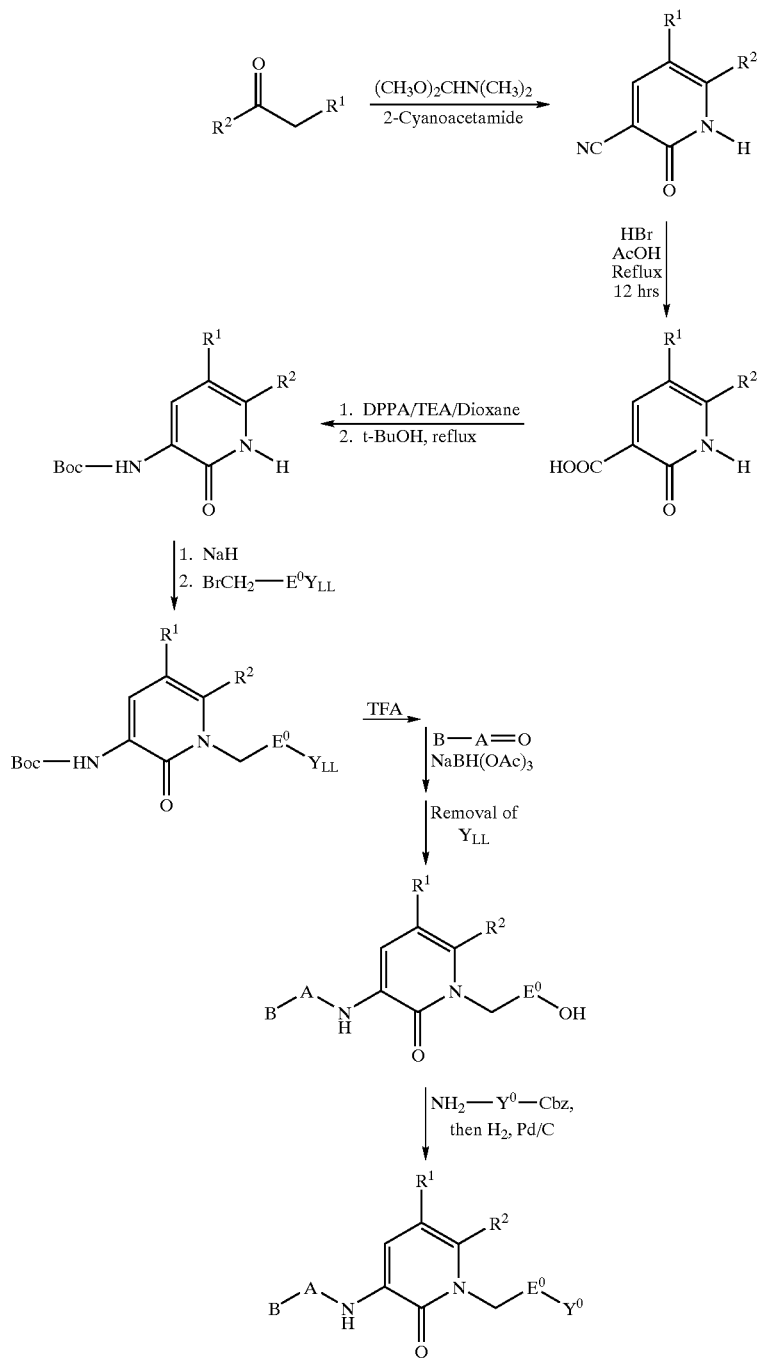

Example 17

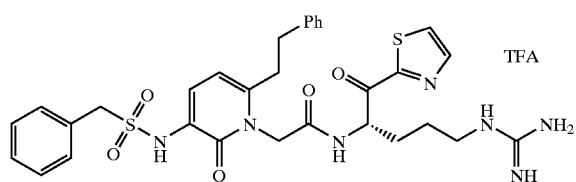

N-[2(S)-2-[1-hydroxy-1-(2-thiazolyl)]-5-[[[(4-methoxy-2,3,6-trimethyl)sulfonylamino]iminomethyl]amino]pentyl]-2-[6-(2-phenylethyl)-2-oxo-3-[[(phenylmethyl)sulfonyl]amino]-1(2H)-pyrid-1-yl]acetamide (0.084 g, 0.098 mmol) was treated with 1,3-dihydro-1-hydroxy-3,3-bis(trifluoromethyl)-1-oxide-1,2-benziodoxole (0.0588 g, 0.147 mmole) in 1 ml acetonitrile. Similar work-up procedure as in preparing EX-1E was used to yield the oxidation product. The oxidation product was treated with thioanisole (0.073 g, 0.59 mmol) and 3 ml trifluoroacetic acid for 6 hours. After removing the TFA, the residue was triturated in ether. It was purified by a preparative C-18 reverse HPLC column using a gradient that proceed from 5% to 95% acetonitrile in H$_2$O in the presence of 0.1% TFA in 30 minutes to yield the product, N-[2(S)-2-[1-Oxo-1-(2-thiazolyl)]-5-[[(amino)iminomethyl]amino]pentyl]-2-[6-(2-phenylethyl)-2-oxo-3-[[(phenylmethyl)sulfonyl]amino]-1(2H)-pyrid-1-yl]acetamide trifluoroacetic acid salt, as a white amorphous solid (0.0232 g, y=31%). HPLC-MS (0 to 95% AcCN/6 min @ 1.0 mL/Min @ 254 nm @ 50° C.): retention time 3.43 min, M+H$^+$=650.2 for formula C$_{31}$H$_{35}$N$_7$O$_5$S$_2$.

Example 18

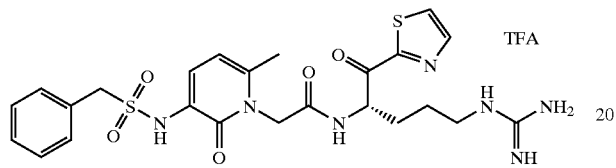

This compound, N-[2(S)-2-[1-Oxo-1-(2-thiazolyl)]-5-[[(amino)iminomethyl]amino]pentyl]-2-[6-methyl-2-oxo-3-[[(phenylmethyl)sulfonyl]amino]-1(2H)-pyrid-1-yl] acetamide trifluoroacetic acid salt, was prepared in a similar fashion as for Example 1. HPLC-MS (0 to 95% AcCN/6 min @ 1.0 mL/Min @ 254 nm @ 50° C.): retention time 2.69 min, M+H$^+$=560.3 for formula C$_{24}$H$_{29}$N$_7$O$_5$S$_2$.

Example 19

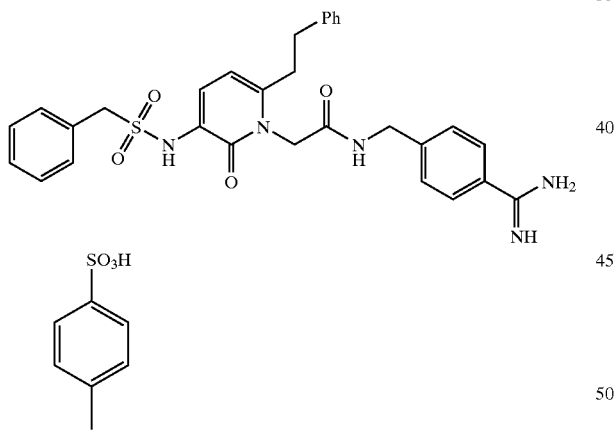

The compound, N-[[4-[(amino)iminomethyl]phenyl]methyl]-2-[6-(2-phenylethyl)-2-oxo-3-[[(phenylmethyl)sulfonyl]amino]-1(2H)-pyrid-1-yl]acetamide p-toluenesulfonic acid salt, was synthesized in a similar fashion as for Example 2 using 2-[6-(2-phenylethyl)-2-oxo-3-[[(phenylmethyl)sulfonyl]amino]-1(2H)-pyrid-1-yl]acetic acid as starting material. HPLC-MS (0 to 95% AcCN/6 min @ 1.0 mL/Min ® 254 nm @ 50° C.): retention time 3.23 min, M+H$^+$=558.5 for formula C$_{30}$H$_{31}$N$_5$O$_4$S. $^1$H NMR (400 MHz, CD$_3$OD): d 2.36 (s, 3H), 2.92 (bm, 4H), 4.43 (s, 2H), 4.54 (s, 2H), 4.87 9s, 2H), 6.10 (d, J=8.0 Hz, 1H), 7.21 (m, 5H), 7.26–7.31 (m, 8H), 7.55 (d, J=8.4 Hz, 2H), 7.69 (d, J=8.0 Hz, 2H), 7.71 (d, J=8.0 Hz, 2H).

Example 20

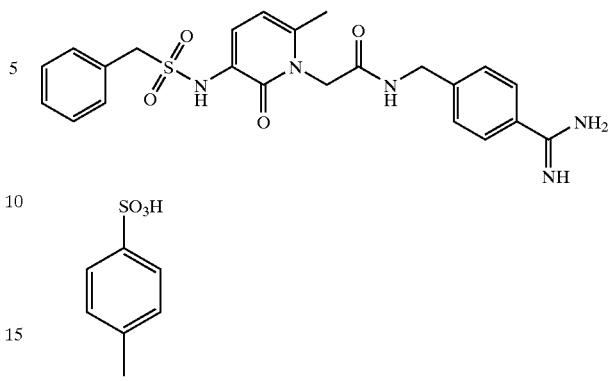

This compound, N-[(4-[[amino)iminomethyl]phenyl]methyl]-2-[6-methyl-2-oxo-3-[[(phenylmethyl)sulfonyl]amino]-1(2H)-pyrid-1-yl]acetamide p-toluenesulfonic acid salt, was synthesized in a similar fashion as for Example 2 using 2-[6-methyl-2-oxo-3-[[(phenylmethyl)sulfonyl]amino]-1(2H)-pyrid-1-yl]acetic acid as starting material. HPLC-MS (0 to 95% AcCN/6 min @ 1.0 mL/1 Min @ 254 nm @ 50° C.): retention time 2.41 min, M+H$^+$=468.1 for formula C$_{23}$H$_{25}$N$_5$O$_4$S. $^1$H NMR (400 MHz, CD$_3$OD): d 2.34 (s, 3H), 2.36 (s, 3H), 4.43 (s, 2H), 4.53 (s, 2H), 4.87 (s, 2H), 6.15 (d, J=7.6 Hz, 1H), 7.21–7.31 (m, 8H), 7.56 (d, J=8.4 Hz, 2H), 7.69 (d, J=8.0 Hz, 2H), 7.72 (d, J=8.0 Hz, 2H), 8.70 (b, 1H), 9.19 (b, 1H).

Example 21

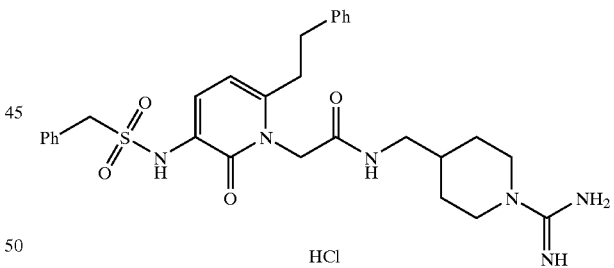

This compound was synthesized in a similar fashion as for Example 2 using 2-[6-(2-phenylethyl)-2-oxo-3-[[(phenylmethyl)sulfonyl]amino]-1(2H)-pyrid-1-yl]acetic acid as starting material and coupling it with 4-[1-(N,N-bis-Boc-amidino)piperidinyl]methylamine The coupling product was treated with 4N HCl in dioxane to generate the product. The compounds were purified by reverse phase C-18 HPLC to generate the final pure products. HPLC-MS (0 to 95% ACCN/6 min @ 1.0 mL/Min @ 254 nm @ 50° C.): retention time 3.10 min, M+H$^+$=565.6 for formula C$_{29}$H$_{37}$N$_6$O$_4$S.

Example 22

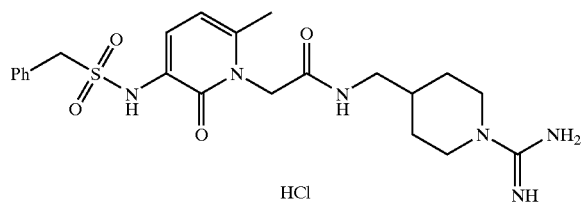

This compound was synthesized in a similar fashion as for Example 2 using 2-[6-methyl-2-oxo-3-[[(phenylmethyl)sulfonyl]amino]-1(2H)-pyrid-1-yl]acetic acid as starting material and coupling it with 4-[1-(N,N-bis-Boc-amidino)piperidinyl]methylamine The coupling product was treated with 4N HCl in dioxane to generate the product. The compounds were purified by reverse phase C-18 HPLC to generate the final pure products. HPLC-MS (0 to 95% AcCN/6 min @ 1.0 mL/Min @ 254 nm @ 50° C.): retention time 2.42 min, M+H$^+$=475.3 for formula $C_{22}H_{31}N_6O_4S$.

One subclass of pyridone analogs have a heteroaryl group substituting the pyridone ring at the 5 or 6 position. Scheme 4 illustrates a process to prepare heteroaryl substituted pyridones. The preparation procedure is exemplified in Example 23 for the preparation of a 6-substituted pyridyl group although it will be readily recognized that a wide variety of substituted pyridines and other 5 and 6 membered heteroaryl groups can be introduced using the procedure described below.

Scheme 4: Preparation of Heteroaryl Pyridones

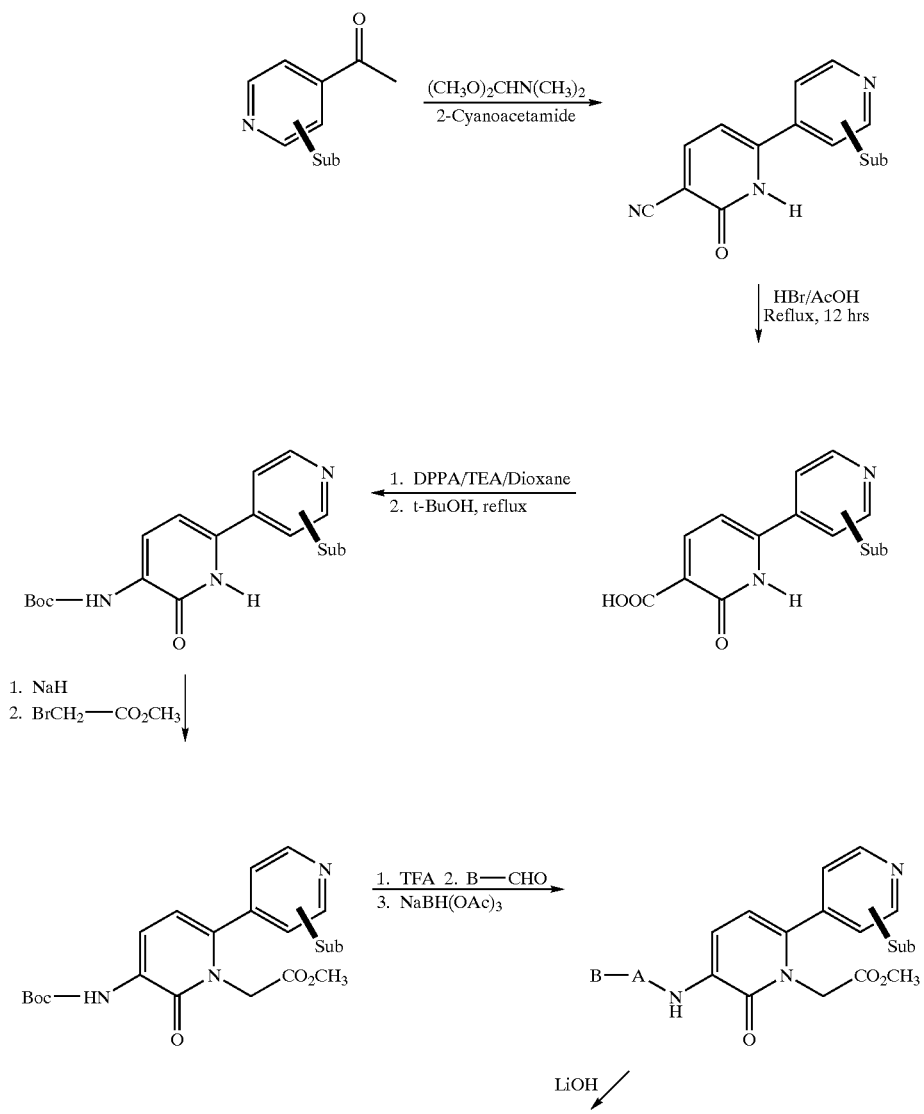

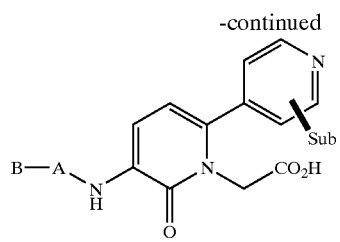
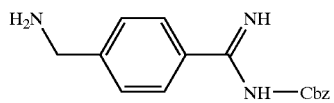
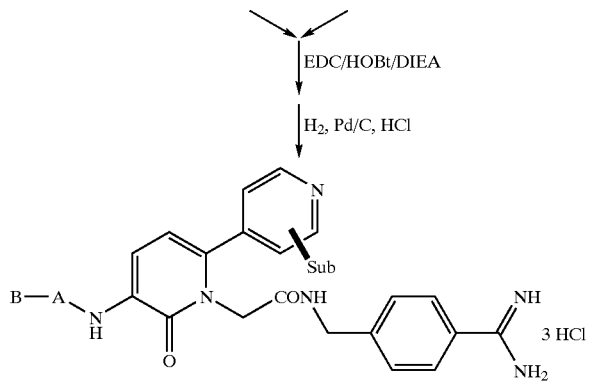

Example 23

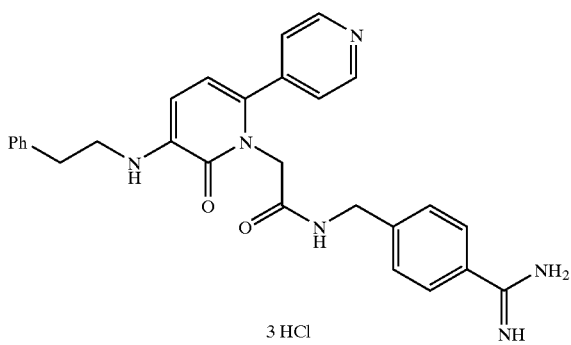

EX-23A)

One equivalent of commercially available 4-acetylpyridine is treated with three equivalents N,N-dimethylformamide dimethyl acetal in refluxing acetonitrile for 12 hours. After removing the solvent and excess amount of N,N-dimethylformamide dimethyl acetal, the resulting yellow solid is dissolved in DMF. To this solution is added one equivalent cyanoacetamide and two equivalents of sodium methoxide. The resulting mixture is heated at 100° C. for 5 hours. After cooling down, the reaction mixture is mixed with water and acidified with HCl to pH 5. The resulting yellow precipitate is filtered, washed with water and dried via vacuum to give the product EX-23A as a yellow solid.

EX-23B)

Compound EX-23A is heated to reflux in one portion of 48% aqueous HBr and two portions of acetic acid for 12 hours. After the mixture is cooled down, mixed with water and adjusted the pH to 5, a light yellow precipitate is formed. The light yellow precipitate is filtered and washed with 1N HCl and water, dried via vacuum to give the product EX-23B as an off-white solid.

EX-23C)

Compound EX-23B is treated with 1.1 equivalent of DPPA, 1 equivalent triethylamine in dioxane at refluxing temperature for two hours. Five equivalents t-butanol is added into the mixture, and the mixture is then refluxed overnight. After removing the solvent, the remaining residue is worked up by standard aqueous work-up procedure. The residue is then purified by silica gel column chromatography to yield Compound EX-23C.

EX-23D)

Compound EX-23C is mixed with one equivalent sodium hydride in DMF and one equivalent methyl bromoacetate subsequently. After stirring at ambient temperature for 12 hours, the reaction is worked up by standard procedure. The product EX-23D is purified by silica gel column chromatography.

EX-23E)

Compound EX-23D is treated with 50% TFA in dichloromethane for 1 hour. After removing the solvent and TFA, the residue is redissolved in THF with one equivalent of triethylamine. To this solution is added one equivalent phenylacetaldehyde and two equivalents sodium triacetoxyborohydride. After stirring for 12 hours, the reaction is quenched with addition of aqueous ammonium chloride. Standard aqueous work-up and silica gel column chromatography yields the desired product EX-23E.

EX-23F)

Compound EX-23E is treated with 1M LiOH in 1:1:1 ratio of THF, methanol and water for half hour. After it is acidified with 1N HCl, the organic solvent is removed and a precipitate will form. The precipitate is filtered, washed with water and dried by vacuum to give the desired product EX-23F. Compound EX-23F is treated with one equivalent EDC and HOBt in the presence of three equivalents diisopropylethylamine in DMF for 10 minutes. One equivalent of 4-aminomethylbenzamidine, which is protected with Cbz at the amidine, is then added into the reaction mixture. After stirring at ambient temperature for four hours, the reaction mixture is worked up by standard procedure and the product EX-23G is purified by silica gel column chromatography.

Compound EX-23G is dissolved in methanol in the presence of 5 equivalents of HCl and 5% equivalent of 10% Pd/C. The mixture is stirred under an atmosphere of hydrogen (ambient pressure) for five hours. After filtration and removing the solvent, Compound 23 is obtained as the pure product.

In a related procedure, 5-substituted pyridones can be prepared as illustrated in Examples 24 and 25.

Example 24

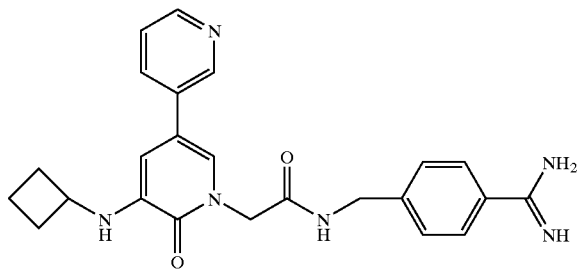

EX-24A)

3-Nitro-2-hydroxylpyridine (49.5 g, 0.35 mol) and 10% Pd/C (4.21 g, 4 mmol) in 500 ml ethanol was stirred under an atmosphere of hydrogen introduced via a balloon for 24 hours. After filtering through a pad of Celite 545 and removing the ethanol, a brown solid was obtained as the pure product, 3-aminopyrid-2-one, (38 g, 97%). HPLC-MS (0 to 30% AcCN/6 mm @ 1.0 mL/Min @ 254 nm @ 50° C.): retention time 0.097 min, M+H$^+$=111.1 for formula $C_5H_7N_2O$.

EX-24B)

Compound EX-24A (27.25 g, 0.248 mol) was treated with Boc anhydride (59.47 g, 0.272 mol), triethylamine (52 ml, 0372 mol) and DMAP (1.5 g, 12.4 mmol) in 500 ml DCM for 4 hours. After an aqueous work-up and removing the solvent, the residue was passed through a short silica gel plug using 40% ethylacetate in hexane as eluent to yield the crude product (28 g, 56%0. Pure product, 3-(N-Boc-amino) pyrid-2-one, was obtained by recrystallization in acetone as a needle-like white crystalline solid. HPLC-MS (0 to 95% AcCN/6 min @ 1.0 mL/Min @ 254 nm @ 50° C.): retention time 239 min, M-Boc+H$^+$=111.1 for formula $C_5H_7N_2O$. $^1$H NMR (400 MHz, CDCl$_3$): d 1.52 (s, 9H), 6.32 (t, J=7.2 Hz, 1H), 7.00(dd, J=6.4, 1.6 Hz, 1H), 7.55(s, 1H), 8.10 (d, J=6.4 Hz, 1H), 12.86(b, 1H). $^{13}$C NMR(101 MHz, CDCl$_3$): d 28.2, 80.8, 107.7, 121.8, 125.2, 129.7, 152.7, 158.8.

EX-24C)

Compound EX-24B (13.58 g, 64.6 mmol) and N-iodosuccinimide (21.8 g, 97 mmol) in 250 ml dichloromethane was stirred at room temperature for 18 hours. After filtration to remove the by-product succinimide, the solvent was removed under reduced pressure. The remaining residue was subjected to a silica gel flash chromatography to yield a brown solid as the product, 3-(N-Boc-amino)-5-iodopyrid-2-one, (17.3 g, 80%). HPLC-MS (0 to 95% AcCN/6 min @ 1.0 mL/Min @ 254 nm @ 50° C.): retention time 3.22 min, M+N$^+$=359.0 for formula $C_{10}H_{13}IN_2O_3Na$.

EX-24D)

Compound EX-24C (9.62 g, 28.6 mmol) was treated with sodium hydride (171 g, 42.9 mmol) 60% in mineral oil in 200 ml THF for 10 minutes. To this mixture was added methyl bromoacetate (433 ml, 45.8 mmol). The resulting structure was stirred at room temperature for 1 hour. After removing the THF, the residue was washed with hexanes to remove the mineral oil. It was then partitioned between ethylacetate and saturated aqueous ammonium chloride. The organic layer was washed with saturated aqueous ammonium chloride three times and dried over anhydrous MgSO$_4$. After removing the solvent, a yellow amorphous solid was obtained as the product, methyl 2-[3-(N-Boc-amino)-5-iodo-2-oxopyrid-2-yl]acetate, (11.1 g, 95%).

EX-24E)

3-Pyridyl boronic acid (2.0 g, 4.93 mmol) was suspended in 80 ml toluene and the mixture was degassed by bubbling nitrogen through for 10 minutes. Tetrakis-(triphenyl) phosphine Palladium (0.54 g, 0.46 mmol) was dissolved in a predegassed mixture of 20 ml toluene and 50 ml methanol. The catalyst solution was added to the boronic acid solution under nitrogen. To this resulting mixture was added compound EX-24D (3.80 g, 9.31 mmol) in 25 ml methanol followed with 22 ml 2M Na$_2$CO$_3$ solution. The reaction solution was heated to reflux for 2.5 hours. After it was cooled down to room temperature, it was mixed with 10 ml 2.5N NaOH and was stirred for an half hour. After removing all the solvent, the remaining residue was re-dissolved in methanol and the pH of the solution was adjusted to 6 with 1N HCl. After removing all the solvent, the residue was absorbed on silica gel and subjected to silica gel flash chromatography using 5% methanol in DCM as the eluate. The pure product, methyl 2-[3-(N-Boc-amino)-5-(pyrid-3-yl)-2-oxopyrid-2-yl]acetate (EX-24E), was obtained as a white amorphous solid (1.01 g, 57%). HPLC-MS (5 to 95% AcCN/6 min @ 1.0 mL/Min @ 254 nm @ 50° C.): retention time 1.89 min, M+H$^+$=346.0 for formula $C_{17}H_{19}N_3O_5$. $^1$H NMR (400 MHz, CDCl$_3$): d 1.53 (s, 9H), 4.82 (s, 2H), 7.62 (d, J=2.4 Hz, 1H), 7.87 (t, J=6.0, 1H), 8.36 (s, 1H), 8.47 (d, J=8.4 Hz, 1H), 8.68 (d, J=4.4 Hz, 1H), 9.05 (s, 1H). $^{13}$C NMR (101 MHz, CDCl$_3$): d 28.0, 50.9, 81.6, 113.8, 117.3, 126.5, 128.9, 130.4, 136.4, 139.8, 140.4, 140.6, 152.7, 156.6, 169.0.

Starting with the intermediate EX-24E, the final inhibitor compound is synthesized in a similar fashion as described in other examples by procedures described above.

Example 25

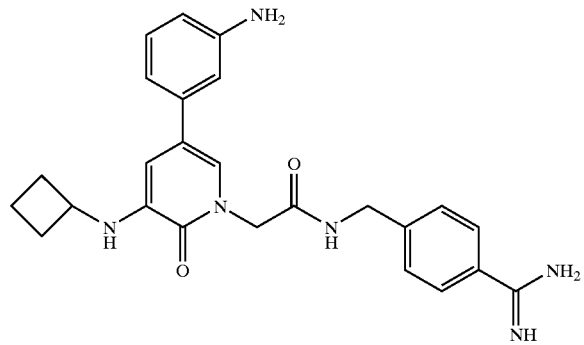

EX-25A)

3-Nitrobenzeneboronic acid (1.41 g, 8.43 mmol) was suspended in 50 ml dioxane and the mixture was degassed with nitrogen. Tetrakis-(triphenyl)phosphine Palladium (0.406 g, 0.35 mmol) dissolved in 10 ml dioxane was added to the boronic acid solution under nitrogen. To this mixture was added compound EX-24D (2.87 g, 7.03 mmol) and 7 ml 2M potassium phosphate solution. The reaction mixture was heated to reflux for 3 hours. After removing the dioxane, the remaining residue was partitioned between ethylacetate and aqueous saturated ammonium chloride. The organic layer was washed with aqueous saturated ammonium chloride and dried over sodium sulfate. The pure product was isolated by a silica gel column flash chromatography to yield a yellow crystalline solid (1.13 g, 40%). The product, methyl 2-[3-N-Boc-amino)-5-(3-nitrophenyl)-2-oxopyrid-2-yl]acetate, showed one peak on LC-MS. However, it is a mixture of two isomers with a ratio of 2.8 to 1 based on $^1$H NMR and $^{13}$C NMR. One isomer has the nitro group at the same side of the Boc amino group, the other in the opposite direction. The NMR data only lists the dominant isomer here. HPLC-MS (5 to 95% AcCN/6 min @ 1.0 mL/Min @ 254 nm @ 50° C.): retention time 3.74 min, M+Na$^+$=4263 for formula $C_{19}H_{21}N_3O_7Na$. $^1$H NMR (400 MHz, CDCl$_3$): d 1.50 (s, 9H), 3.82 (s, 3H), 4.80 (s, 2H), 7.20 (d, J=2.4 Hz, 1H), 7.56 (t, J=8.0, 1H), 7.66 (s, 1H), 7.81 (d, J=8.0 Hz, 1H), 8.15 (d, J=8.0 Hz, 1H), 8.28 (d, J=2.4 Hz, 1H), 8.36 (s, 1H).

Starting with the intermediate EX-25A, the final inhibitor compound is synthesized in a similar fashion as described in other examples by procedures described above.

Preparation of sulfonyl analogs of pyridones of the present invention in which a sulfonyl replaces the carbonyl group of the N-1 acetamide side chain can be accomplished by use of the general procedure in Scheme 3. Example 26, a specific example of a sulfonamide of the present invention, is synthesized as according to the general procedure shown in Scheme 5.

Scheme 5: Preparation of Pyridonyl Alkyl Sulfonamides

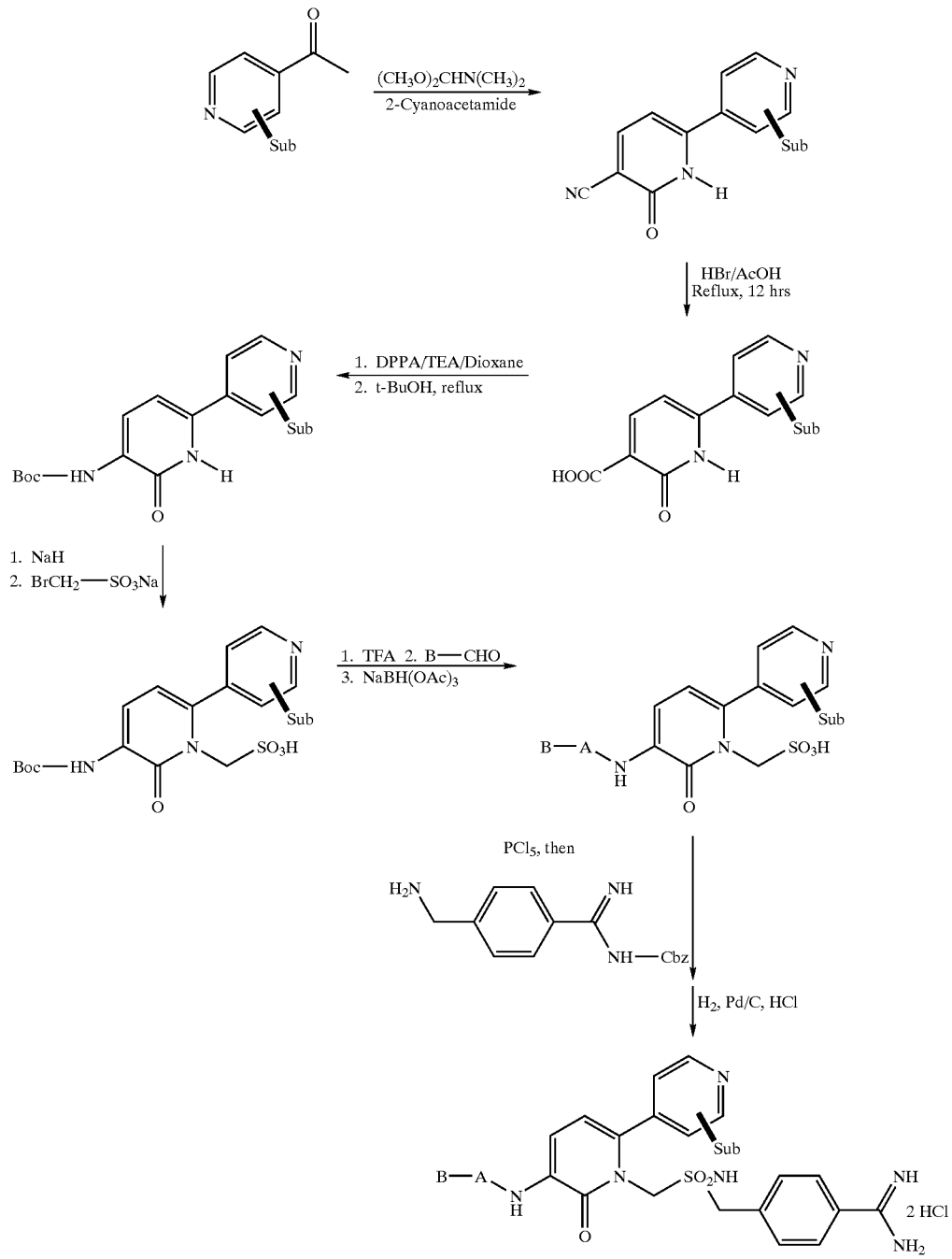

Example 26

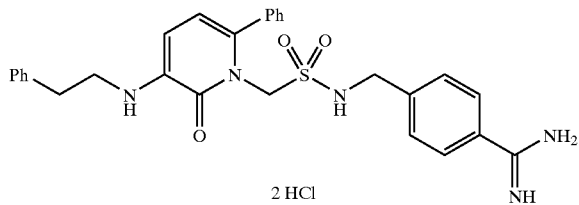

2 HCl

Compound EX-26C can be prepared using same methods as described in Example 23 for compounds EX-23A, EX-23B, and EX-23C.

EX-26D)

Compound EX-26C is treated with 1.1 equivalent NaH and 1.5 equivalents sodium bromomethanesulfonate in DMF overnight. The reaction is quenched by dilution with water and addition of 1N HCl to adjust the reaction solution to a pH of 3 to precipitate the product The crude product is obtained by filtration and washing with water and ether. The pure product EX-26D is further purified by recrystallization in ethanol.

EX-26E)

Compound EX-26D is treated with 50% TFA in dichloromethane for 1 hour. After removing the solvent and TFA, the residue is redissolved in THF/Methanol with one equivalent of triethylamine. To this solution is added one equivalent phenylacetaldehyde and two equivalents sodium triacetoxyborohydride. After stirring for 12 hours, the reaction is quenched with addition of aqueous ammonium chloride. Standard aqueous work-up and silica gel column chromatography yields the desired product EX-26E.

EX-26F)

Compound EX-26E is treated with one equivalent $PCl_5$ in toluene for an half hour. One equivalent of 4-aminomethylbenzamidine, which is protected with Cbz at the amidine, is then added into the reaction mixture followed with the addition of five equivalents pyridine. The mixture is allowed to be stirred for 12 hours. The reaction mixture is worked up by standard procedure and the product EX-26F is purified by silica gel column chromatography.

Compound 26 is prepared from EX-26F using the procedure for compound 23 in Example 23.

Preparation of methylene analogs of pyridones of the present invention in which a methylene replaces the carbonyl group of the N-1 acetamide side chain can be accomplished by using the essential features of the general procedure in Scheme 3. Example 27, a specific example of an ethyleneamine of the present invention, can be synthesized as shown specifically in Scheme 6.

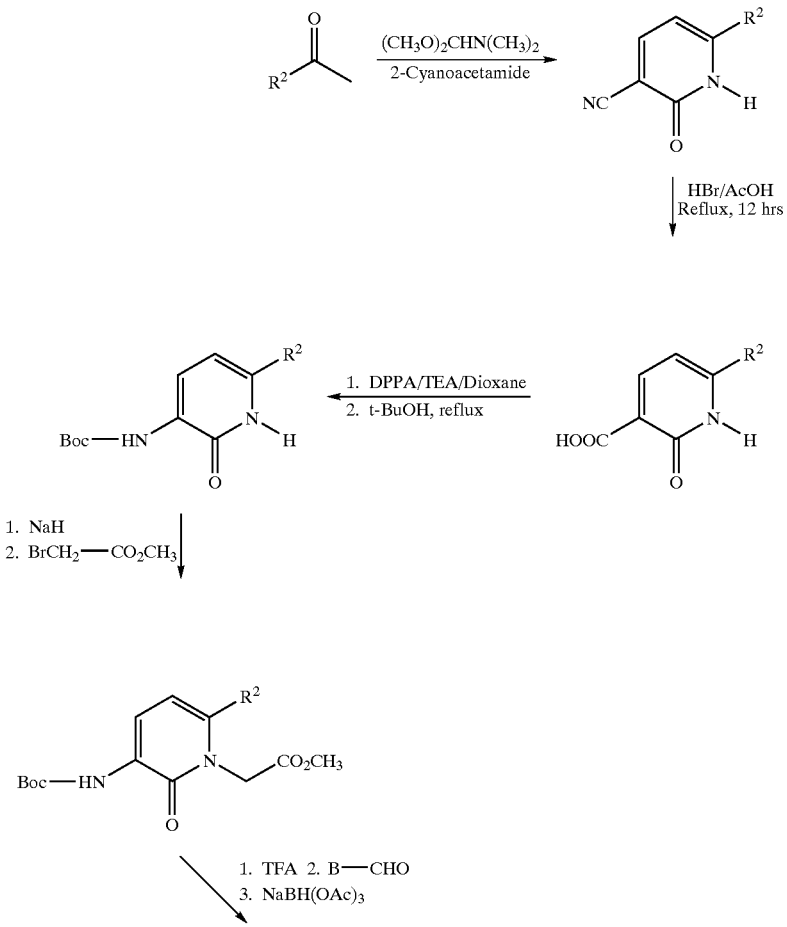

Scheme 6: Preparation of Ethylene Pyridone Analogs

-continued

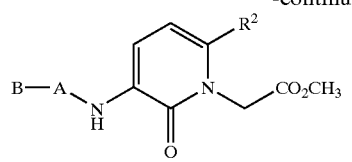

↙ DIBAL

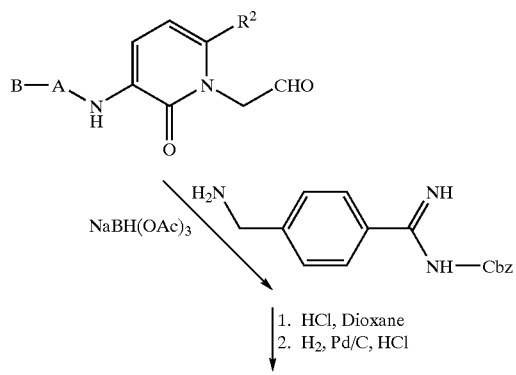

1. HCl, Dioxane
2. H₂, Pd/C, HCl

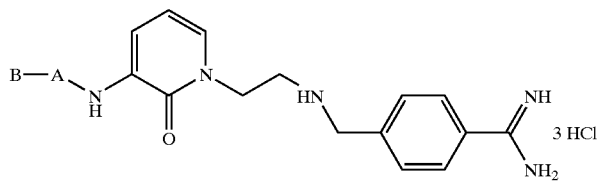

3 HCl

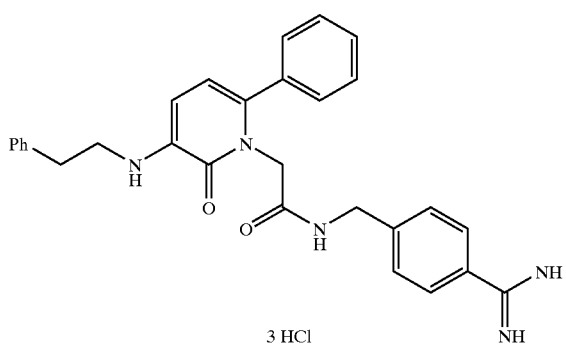

3 HCl

EX-27A)

To a ether solution of pyridinylacetate ester with the B-A group added, diisobutylaluminum hydride (5 eq.) is added at −78° C. After 30 minutes stirring, methanol is added to quench the reaction. The resulting mixture is poured into a saturated aqueous solution of Rochelle salt. The layers are separated, and the aqueous layer is extracted with ethyl ester. The combined extract is dried over MgSO₄, and the solvent is evaporated to dryness. The remaining residue is subjected to a silica gel column chromatography to yield the pure product aldehyde (EX-27A).

EX-27B)

Compound EX-27A is mixed with one equivalent of Cbz protected 4-amidinobenzylamine and two equivalents of sodium triacetoxyborohydride in THF. The reaction mixture is worked up according to the standard procedure. The product EX-27B is purified by silica gel column chromatography.

Compound EX-27B is first treated with 4H HCl in dioxane for 4 hours. After removing the dioxane, the residue is redissolved in methanol in the presence of 5 equivalents of HCl and 5% equivalent of 10% Pd/C. The mixture is stirred under an atmosphere of hydrogen (ambient pressure) for five hours. After filtration and removing the solvent, the compound is obtained as the pure product.

Another subclass of pyridone analogs have the general structure as shown in FIG. 3. Substituents are defined as disclosed herein. $Z^0$ can be heteroatoms such as S, O, N, and others. The synthesis of this subclass of pyridone analogs is exemplified as in the synthesis of Example 28 as summarized in Scheme 7.

FIG. 3

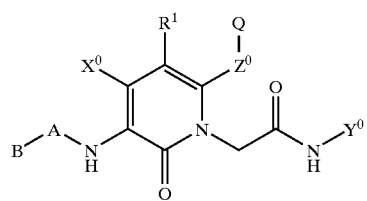

Scheme 7: Preparation of Z⁰-Q Analogs of Pyridones
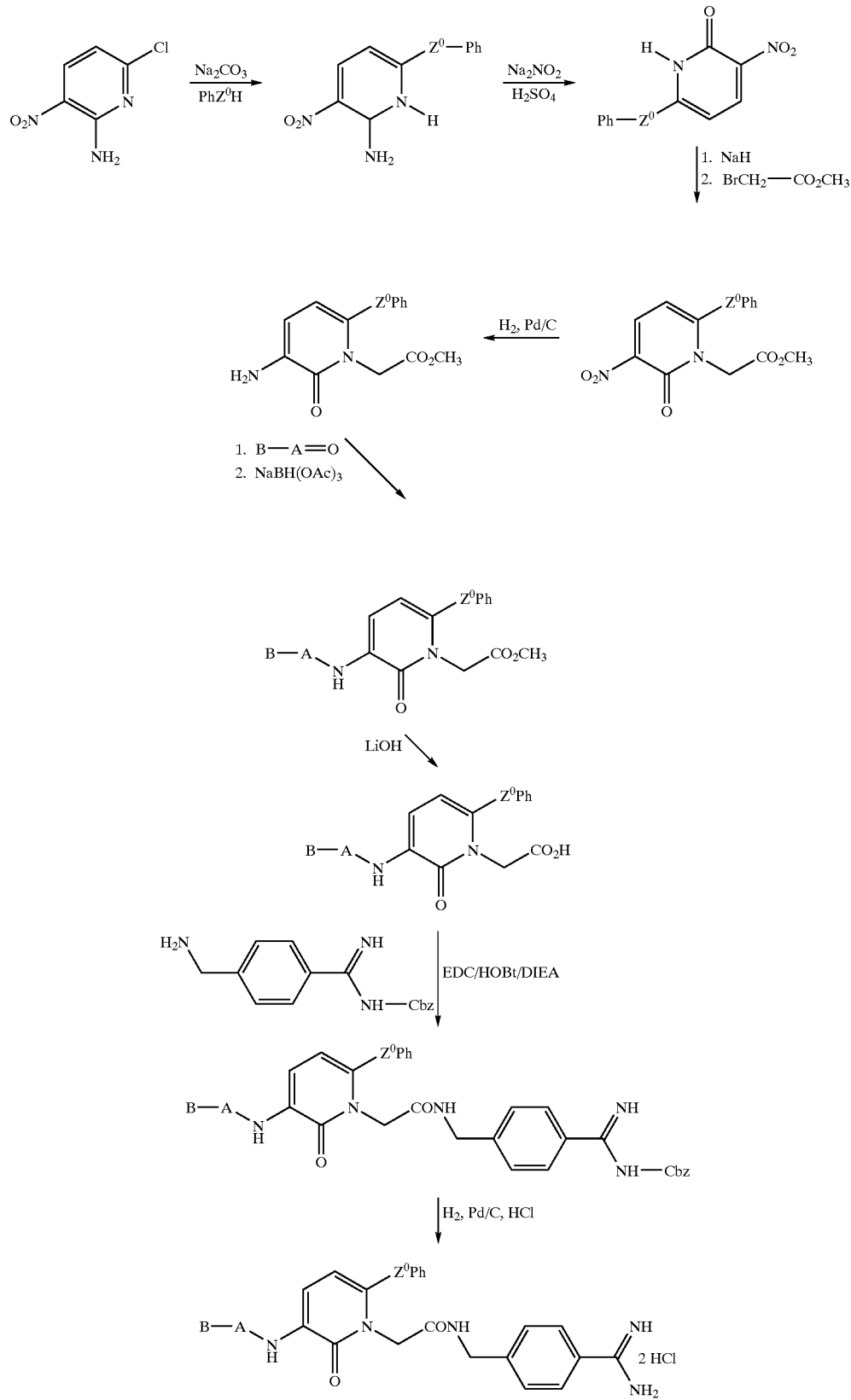

Example 28

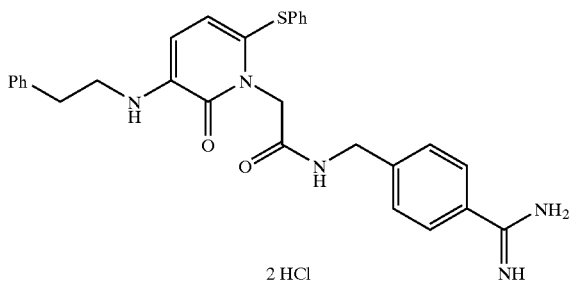

2 HCl

EX-28A)

Commercially available compound 2-amino-3-nitro-6-chloropyridine is reacted with one equivalent of phenylthiol in the presence of sodium carbonate in DMF at 80° C. After the completion of the reaction, the reaction mixture is mixed with water. Filtration yields the crude product EX-28A that can be purified by recrystallization in methanol.

EX-28B)

Compound EX-28A is dissolved in 12N $H_2SO_4$, and the solution is treated with aqueous solution of $NaNO_2$ (3 eq.) firstly at 0° C., then at 100° C. Dilution with water precipitates the product. Filtration and washing with water and ether yields the crude product EX-23B that can be further purified by recrystallization in ethanol.

EX-28C)

Compound EX-28B is mixed with one equivalent sodium hydride in DMF and one equivalent methyl bromoacetate subsequently. After stirring at ambient temperature for 12 hours, the reaction is worked up by standard procedure. The product EX-28C is purified by silica gel column chromatography.

EX-28D)

Compound EX-28C is dissolved in methanol in the presence of 5% equivalent of 10% Pd/C. The mixture is stirred under an atmosphere of hydrogen (ambient pressure) for an half hour. After filtration and removing the solvent, Compound EX-28D is obtained as the pure product.

Example compound 28 can be prepared from EX-28D in a similar fashion as described in the preparation of compounds EX-23E, EX-23F, EX-23G and 23.

Another subclass of pyridone analogs have the general structure as shown in FIG. 4. Pyridones, wherein a wide variety of $R^2$ substituents can be prepared by a metal catalyzed coupling reaction of a 6-bromo group in an appropriately substituted intermediate pyridone, can be prepared using the general procedures and processes shown in Scheme 8 and as illustrated below in specific Example 29. $R^2$ groups may be aryl and heteroaryl and substituents for these may include, for example, amino, substituted amino, carboxy, carboxamido, suflonylamido, and the likes.

FIG. 4

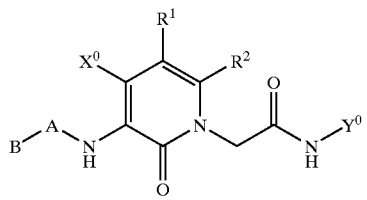

Scheme 8: Introduction of $R^2$ Groups into Pyridone Intermediates and the Resulting Products

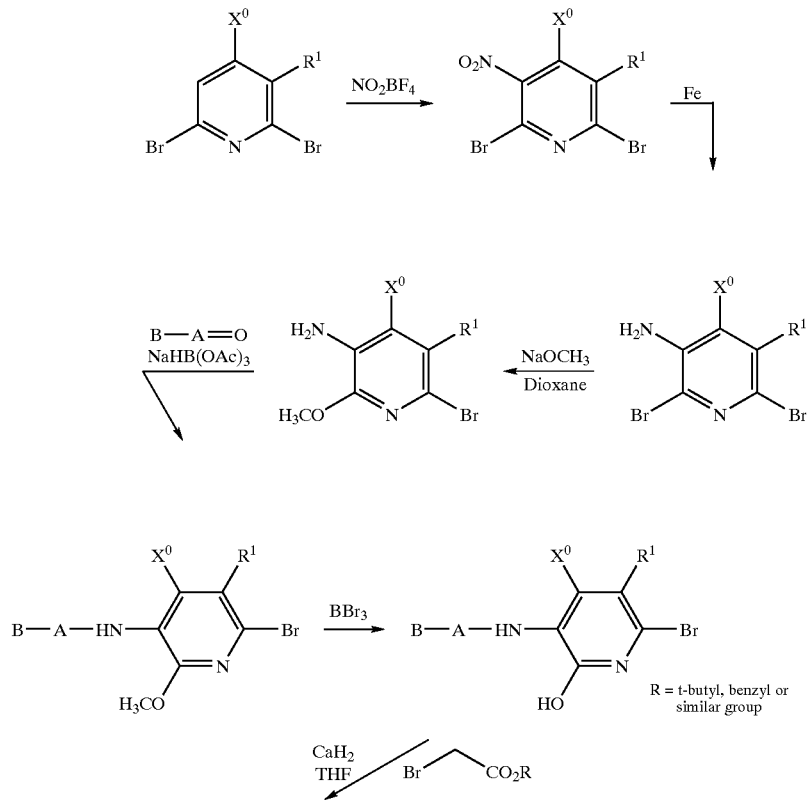

R = t-butyl, benzyl or similar group

-continued

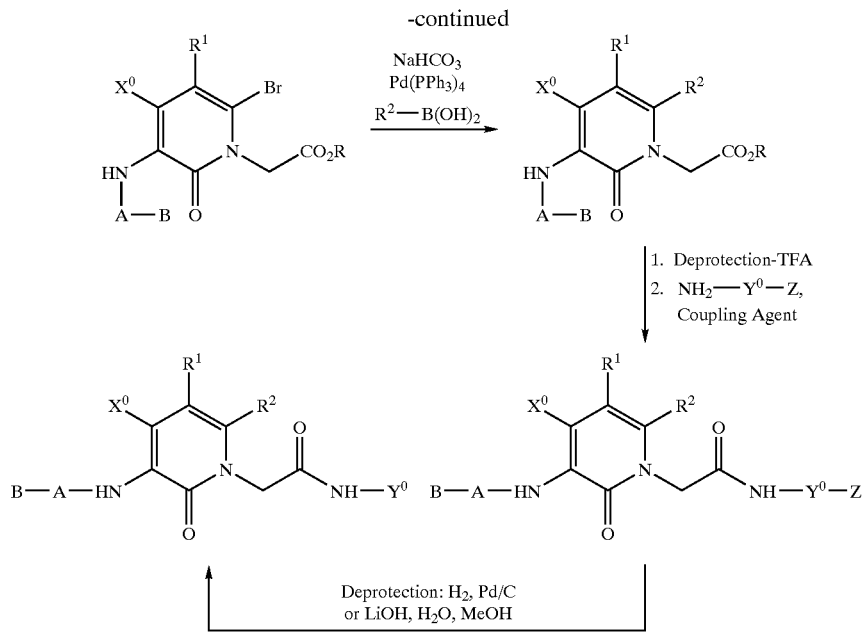

Example 29

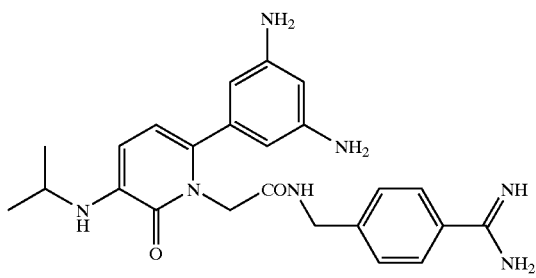

A solution of 2,6-dibromopyridine (10.0 g, 42 mmol) and nitronium tetrafluoroborate (11.2 g, 84 mmol) in acetonitrile was heated to reflux for 18 hours. The brown reaction was allowed to cool to room temperature and was diluted with 50 mL of a saturated sodium bicarbonate solution. The solution was washed with water, brine, dried over magnesium sulfate, and filtered. The solvent was removed A by evaporation to afford the crude product. The product was purified by column chromatography (10% ethyl acetate-hexane) to afford 4.76 g (40%) of a white solid of product EX-29A; MS (ES, m/z) 281 (M+H).

The nitro compound EX-29A (6.8 g, 24.3 mmol) was stirred in glacial acetic acid. Powdered iron (6.7 g, 119 mmol) was added and the solution was heated to 80° C. with vigorous stirring. The solution was stirred at 80° C. for 15 minutes at which point the iron had turned gray. The reaction mixture was filtered through celite and the solid was washed with ether and ethyl acetate. The resultant organic layer was washed with water, brine, dried over magnesium sulfate, and filtered. The solvent was removed to afford the crude product. The product was purified by column chromatography (20% ethyl acetate-hexane) to afford 5.26 g (87%) of a white solid of product EX-29B; MS (ES, m/z) 251 (M+H).

A solution of the 3-amino-2,6-dibromopyridine EX-29B (4.0 g, 16 mmol) and sodium methoxide (4.3 g, 80 mmol) in dioxane was heated to reflux for 12 hours. The brown reaction was allowed to cool to room temperature and diluted with water. The solution was extracted with ether and the organic layer was washed with water, brine, dried over magnesium sulfate, and filtered. The solvent was removed by evaporation to afford the crude product. The product was purified by column chromatography (20% ethyl acetate-hexane) to afford a white solid of product EX-29C; MS (ES, m/z) 204 (M+H).

Sodium triacetoxyborohydride (43.0 mmol) was added to a solution of the the 3-amino-2-methoxybromopyridine EX-29C (11.0 mmol), acetone (13.6 mmol) and a drop of acetic acid in a tetrahydrofuran-dichloromethane (1:1) solution. After stirring at room temperature for 14 hours additional acetone (1.0 mL, 13.6 mmol) and acetic acid (excess) was added and the solution stirred at room temperature for 18 hours. The solution was diluted with ether and water. The organic layer was washed with brine, dried over magnesium sulfate, and filtered. The solvent was removed by evaporation to afford the crude product. The product was purified by column chromatography (15% ethyl acetate-hexane) to afford a yellow oil of isopropylaminopyridine product EX-29D; MS (ES, m/z) 245 (M+H).

Boron tribromide 1M (2.7 mL, 2.7 mmol) was added to a solution of the isopropylaminopyridine product EX-29D (0.50 g, 0.88 mmol) in dichloromethane at −10° C. The reaction mixture was diluted with water and extracted with ether. The organic layer was washed with water, brine, dried over magnesium sulfate, and filtered. The solvent was removed by evaporation to afford the crude product. The product was purified by column chromatography (20% ethyl acetate-hexane) to afford a white solid of product EX-29E; MS (ES, m/z) 231 (M+H).

A suspension of $CaH_2$ (40.96 mmol) in tetrahydrofuran was added to the hydroxy pyridine EX-29E (20.68 mmol) in tetrahydrofuran dropwise via an addition funnel. The resulting suspension was heated to reflux for 30 minutes. The mixture was then added a solution of tert-butyl bromoacetate (3.40 mL, 23.03 mmol) in tetrahydrofuran (2.3 M). Refluxing of the mixture was continued for 18 hours. The reaction mixture was allowed to cool to room temperature, and the cautiously poured in to a stirred ice water mixture. The aqueous layer was extracted with ethyl acetate. The organic layer was washed with water, brine, dried over magnesium sulfate, and filtered. The solvent was removed by evaporation to afford the crude product. The product was purified by column chromatography (20% ethyl acetate-hexane) to afford a white solid of the tert-butyl ester product EX-29E; MS (ES, m/z) 345 (M+H).

A mixture of the tert-butyl ester pyridone EX-29E (14.05 mmol) and 3-amino-5-nitrophenylboronic acid (15.10 mmol) in THF was stirred for 10 minutes under an atmosphere of nitrogen. Sodium carbonate (16.8 mmol) was added followed by tertakis(triphenylphosphine)palladium (O) (10 mol %). The resulting mixture was allowed to stir for 5 minutes at room temperature, then heated to reflux for 18 hours. The reaction mixture was allowed to cool to room temperature and was diluted with ethyl acetate. The organic layer was washed with water, brine, dried over magnesium sulfate, and filtered. The solvent was removed by evaporation to afford the crude product. The product was purified by column, chromatography to afford a clear oil of product EX-29F; MS (ES, m/z) 503 (M+H).

A solution of the 6-phenylpyridone tert-butyl ester EX-29F (6.996 mmol) in dry chloroform was added trifluoroacetic acid (70.09 mmol) in one portion at room temperature. The resulting clear yellow solution was allowed to stir over night. The solvent was removed under reduced pressure and trituration from ethyl ether/hexanes afford pure product EX-29G as a tan solid; MS (ES, m/z) 447 (M+H)

R-2 PS-carbodiimide (1.00 mmol/g) (1.4 mmol) was added to a slurry of the acid EX-29G (0.71 mmol), 1-hydroxybenzotriazole (0.71 mmol), 4-(N-benzyloxycarbonylamidino)benzylamine hydrochloride (0.84 mmol), and N-methylmorpholine (5.6 mmol) in a dichloromethane-dimethylformamide (3:1) solution, and the suspension was agitated for 3 hours. Upon completion of the reaction, the R-1 polyamine resin (2.81 mmol/g) (5.6 mmol) and polymer-bound aldehyde R-3 (2.3 mmol/g) (2.30 mmol) were added, and the suspension was agitated for 1 hour. The solution was filtered, and the polymer was rinsed with dimethylformamide and dichloromethane until no more UV activity was seen in the dichloromethane washing. The solvent was removed under reduced pressure, and trituration from ethyl ether/hexanes afforded pure product EX-29H as a white solid; MS (ES, m/z) 712 (M+H).

A catalytic amount of palladium on carbon (5%) in dioxane was added to 3 mL of a methanol-4N hydrochloric acid/dioxane (3:1) solution of the protected pyridinone compound EX-29H (0.88 mmol), and the mixture was stirred under a balloon of hydrogen at room temperature for 12 hours. The mixture was filtered through celite, and the solvent was evaporated to afford the product. The product was purified by reverse-phase chromatography to afford a white solid of product; MS (ES, m/z) 448 (M+H).

Using the examples and methods described herein previously, the following examples having a amidinoaralkyl or amidinoheteroaralkyl type Y° group could be prepared:

N-[[4-aminoiminomethylphenyl]methyl]-2-[1-[6-[3-aminophenoxy]-4-chloro-3-[N,N-dimethylhydrazino]-2-oxo-1(2H)pyridinyl]]acetamide;
N-[[4aminoiminomethylphenyl]methyl]-2-[1-[6-[3-aminophenoxy]-3-[N-ethyl-N-methylhydrazino]-4-fluoro-2-oxo-1(4H)-pyridinyl]]acetamide;
N-[[4-aminoiminomethylphenyl]methyl]-2-[1-[6-[3-aminophenoxy]-3-[N,N-diethylhydrazino]-2-oxo-1(4H)-pyridinyl]]acetamide;
N-[[4-aminoiminomethylphenyl]methyl]-4-chloro-2-[1-[6-3,5-diaminophenoxy]-3-[N,N-dimethylhydrazino]-2-oxo-1(2H)-pyridinyl]]acetamide;
N-[[4-aminoiminomethylphenyl]methyl]-2-[1-[6-[3-aminophenylthio]-3-[N,N-dimethylhydrazino]-2-oxo-1(2H)-pyridinyl]]acetamide;
N-[[aminoiminomethylphenyl]methyl]-2-[1-[6-[3-aminophenylthio]-3-[N,N-dimethylhydrazino]-4fluoro-2-oxo-1(2H)-pyridinyl]]acetamide;
N-[[4-aminoiminomethylphenyl]methyl]-2-[1-[6-[3-amino-5-carboxyphenoxy]-4-chloro-3-[N,N-dimethylhydrazino]-2-oxo-1(2H)-pyridinyl]]acetamide;
N-[[4-aminoiminomethylphenyl]methyl]-2-[1-[6-[3,5-diaminophenoxy]-3-[N-ethyl-N-methylhydrazino]4-fluoro-2-oxo-1(4H)-pyridinyl]]acetamide:
N-[[4-aminoiminomethylphenyl]methyl]-2-[1-[6-[3,5-diaminophenoxyl]-3-[N,N-diethylhydrazino]-2-oxo-1(4H)-pyridinyl]]acetamide;
N-[[4-aminoiminomethylphenyl]methyl]-4-chloro-2-[1-[6-[3,5-diaminophenylthio]-3-[N,N-dimethylhydrazino]-2-oxo-1(2H)-pyridinyl]]acetamide;
N-[[4-aminoiminomethylphenyl]methyl]-2-[1-[6-[3-amino-5-carboxyphenylthio]-3-[N,N-dimethylhydrazino]-2-oxo-1(2H)-pyridinyl]]acetamide;
N-[[4-aminoiminomethylphenyl]methyl]-2-[1-[6-[3-amino-5-carboxyphenylthio]-3-[N,N-dimethylhydrazino]-4-fluoro-2-oxo-1(2H)pyridinyl]]acetamide;
N-[[4-aminoiminomethylphenyl]methyl]-2-[1-[6-[3-aminophenyl]-4-chloro-3-[N,N-dimethylhydrazino]-2-oxo-1(2H)-pyridinyl]]acetamide;
N-[[4-aminoiminomethylphenyl]methyl]-2-[1-[6-[3-aminophenyl]-3-[N-ethyl-N-methythydrazino]fluoro-2-oxo-1(4H)-pyridinyl]]acetamide;
N-[[4-aminoiminomethylphenyl]methyl]-2-[1-[6-[3-aminophenyl]-3-[N,N-diethylhydrazino]-2-oxo-1(4H)-pyridinyl]]acetamide;
N-[[4-aminoiminomethylphenyl]methyl]-4-chloro-2-[1-[6-[3,5-diaminophenyl]-3-[N,N-dimethylhydrazino]-2-oxo-1(2H)-pyridinyl]]acetamide;
N-[[4-aminoiminomethylphenyl]methyl]-2-[1-[6-[3-aminophenyl]-3-[N,N-dimethylhydrazino]-2-oxo-1(2H)-pyridinyl]]acetamide;
N-[[4-aminoiminomethylphenyl]methyl]-2-[1-[6-[3-aminophenyl]-3-[N,N-dimethylhydrazino]-1-fluoro-2-oxo-1(2H)pyridinyl]]acetamide;
N-[[4-aminoiminomethylphenyl]methyl]-2-[1-[6-[3-amino-5-carboxyphenyl]-4-chloro-3-[N,N-dimethylhydrazino]-2-oxo-1(2H)-pyridinyl]]acetamide;
N-[[4-aminoiminomethylphenyl]methyl]-2-[1-[6-[3,5 diaminophenyl]-3-[N-ethyl-N-methylhydrazino]-1-fluoro-2-oxo-1(4H)-pyridinyl]]acetamide;
N-[[4-aminoiminomethylphenyl]methyl]-2-[1-[6-[3,5-diaminophenyl]-33-[N,N-diethylhydrazino]-2-oxo-1(4H) pyridinyl]]acetamide;
N-[[4aminoiminomethylphenyl]methyl]-4-chloro-2-[1-[6-[3,5-diaminophenyl]-3-[N,N-dimethylhydrazino]-2-oxo-1(2H)-pyridinyl]]acetamide;
N-[[4-aminoiminomethylphenyl]methyl]-2-[1-[6-[3-amino-5-carboxyphenyl]-3-[N,N-dimethylhydrazino]-2-oxo-1(2H)-pyridinyl]]acetamide;
N-[[4-aminoiminomethylphenyl]methyl]-2-[1-[6-[3-amino-5-carboxyphenylthio]-3-[N,N-dimethylhydrazino]-4-fluoro-2-oxo-1(2H)-pyridinyl]]acetamide.

Using the examples and methods described herein previously, the following further examples having a amidinoaralkyl or amidinoheteroaralkyl type Y° group could be prepared of the formula:

wherein;

$R^2$ is 3-aminophenoxy, B is 3-chlorophenyl, A is $CH_2CH_2$, $Y^O$ is 4-amidinobenzyl, $R^1$ is hydrido, and $X^O$ is hydrido;

$R^2$ is 3-aminophenoxy, B is phenyl, A is $CH_2$, $Y^O$ is 4-amidinobenzyl, $R^1$ is hydrido, and $X^O$ is hydrido;

$R^2$ is phenylthio, B is 3-chlorophenyl, A is $CH_2CH_2$, $Y^O$ is 4-amidinobenzyl, $R^1$ is hydrido, and $X^O$ is hydrido;

$R^2$ is 3-amino-4-carboxy-2-thienyl, B is phenyl, A is $CH_2CH_2$, $Y^O$ is 4-amidinobenzyl, $R^1$ is hydrido, and $X^O$ is hydrido;

$R^2$ is 3,4-diamino-2-thienyl, B is phenyl, A is $CH_2CH_2$, $Y^O$ is 4-amidinobenzyl, $R^1$ is hydrido, and $X^O$ is hydrido;

$R^2$ is phenoxy, B is 3-aminophenyl, A is C(O)NH, $Y^O$ is 4-amidinobenzyl, $R^1$ is hydrido, and $X^O$ is hydrido;

$R^2$ is phenoxy, B is 3-amidinophenyl, A is $CH_2$, $Y^O$ is 4-amidinobenzyl, $R^1$ is hydrido, and $X^O$ is hydrido;

$R^2$ is 3-(N-methylamino)-2-thienyl, B is phenyl, A is $CH_2CH_2$, $Y^O$ is 4-amidinobenzyl, $R^1$ is hydrido, and $X^O$ is hydrido;

$R^2$ is 3-methylsulfonamido-2-thienyl, B is phenyl, A is $CH_2CH_2$, $Y^O$ is 4-amidinobenzyl, $R^1$ is hydrido, and $X^O$ is hydrido;

$R^2$ is phenylthio, B is 4-amidinophenyl, A is $CH_2$, $Y^O$ is 4-amidinobenzyl, $R^1$ is hydrido, and $X^O$ is hydrido;

$R^2$ is 3-methylaminophenoxy, B is phenyl, A is $CH_2CH_2$, $Y^O$ is 4-amidinobenzyl, $R^1$ is hydrido, and $X^O$ is hydrido;

$R^2$ is 3-aminophenylthio, B is 3-chlorophenyl, A is $CH_2CH_2$, $Y^O$ is 4-amidinobenzyl, $R^1$ is hydrido, and $X^O$ is hydrido;

$R^2$ is 3-aminophenylamino, B is phenyl, A is $CH_2$, $Y^O$ is 4-amidinobenzyl, $R^1$ is hydrido, and $X^O$ is hydrido;

$R^2$ is 3-aminophenoxy, B is 3-chlorophenyl, A is $CH_2CH_2$, $Y^O$ is 4-amidinobenzyl, $R^1$ is amino, and $X^O$ is hydrido;

$R^2$ is 3-amino-2-thienyl, B is phenyl, A is $CH_2$, $Y^O$ is 4-amidinobenzyl, $R^1$ is amino, and $X^O$ is hydrido;

$R^2$ is phenylthio, B is 3-chlorophenyl, A is $CH_2CH_2$, $Y^O$ is 4-amidinobenzyl, $R^1$ is amino, and $X^O$ is hydrido;

$R^2$ is 3-aminophenoxy, B is 3-chlorophenyl, A is $CH_2CH_2$, $Y^O$ is 4-amidinobenzyl, $R^1$ is aminomethyl, and $X^O$ is hydrido;

$R^2$ is 3-amino-2-thienyl, B is phenyl, A is $CH_2$, $Y^O$ is 4-amidinobenzyl, $R^1$ is aminomethyl, and $X^O$ is hydrido;

$R^2$ is 3-amidocarbonyl-5-aminophenoxy, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-benzylamidocarbonyl)phenoxy, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-(2-chlorobenzyl)amidocarbonyl)phenoxy, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-(2-chlorobenzyl)amidosulfonyl)phenoxy, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-(2-trifluoromethylbenzyl)amidocarbonyl)phenoxy, B is 3-chlorophenyl, A is $CH_2CH_2$, $Y^O$ is 4-amidinobenzyl, $R^1$ is chloro, and $X^O$ is hydrido;

$R^2$ is 3,5-diaminophenoxy, B is 3-chlorophenyl, A is $CH_2CH_2$, $Y^O$ is 4-amidinobenzyl, $R^1$ is chloro, and $X^O$ is hydrido;

$R^2$ is 3-amino-5-carboxy-2-thienyl, B is 3-chlorophenyl, A is $CH_2CH_2$, $Y^O$ is 4-amidinobenzyl, $R^1$ is chloro, and $X^O$ is hydrido;

$R^2$ is 3-amidocarbonyl-5-aminophenylthio, B is 3-chlorophenyl, A is $CH_2CH_2$, $Y^O$ is 4-amidinobenzyl, $R^1$ is hydrido, and $X^O$ is hydrido;

$R^2$ is 3-amino-5-(N-benzylamidocarbonyl)-2-thienyl, B is 3-chlorophenyl, A is $CH_2CH_2$, $Y^O$ is 4-amidinobenzyl, $R^1$ is hydrido, and $X^O$ is hydrido;

$R^2$ is 3-amino-5-(N-(2-chlorobenzyl)amidocarbonyl)-2-thienyl, B is 3-chlorophenyl, A is $CH_2CH_2$, $Y^O$ is 4-amidinobenzyl, $R^1$ is hydrido, and $X^O$ is hydrido;

$R^2$ is 3-amino-5-(N-(2-chlorobenzyl)amidosulfonyl)-2-thienyl, B is 3-chlorophenyl, A is $CH_2CH_2$, $Y^O$ is 4-amidinobenzyl $R^1$ is hydrido, and $X^O$ is hydrido;

$R^2$ is 3-amino-5-(N-(2-trifluoromethylbenzyl)amidocarbonyl)-2-thienyl, B is 3-chlorophenyl, A is $CH_2CH_2$, $Y^O$ is 4-amidinobenzyl, $R^1$ is hydrido, and $X^O$ is hydrido;

$R^2$ is 3,5-diaminophenylamino, B is 3-chlorophenyl, A is $CH_2CH_2$, $Y^O$ is 4-amidinobenzyl, $R^1$ is hydrido, and $X^O$ is hydrido;

$R^2$ is 3-amino-5-carboxyphenylamino, B is 3-chlorophenyl, A is $CH_2CH_2$, $Y^O$ is 4-amidinobenzyl, $R^1$ is hydrido, and $X^O$ is hydrido;

$R^2$ is 3-aminophenoxy, B is 2,2,2-trifluoroethyl, A is single bond, $Y^O$ is 4-amidinobenzyl, $R^1$ is hydrido, and $X^O$ is hydrido;

$R^2$ is 3-aminophenoxy, B is (S)-2-butyl, A is single bond, $Y^O$ is 4-amidinobenzyl, $R^1$ is hydrido, and $X^O$ is hydrido;

$R^2$ is 5-amino-2-fluorophenoxy, B is isopropyl, A is single bond, $Y^O$ is 4-amidinobenzyl, $R^1$ is hydrido, and $X^O$ is hydrido;

$R^2$ is 2-methyl-3-aminophenoxy, B is isopropyl, A is single bond, $Y^O$ is 4-amidinobenzyl, $R^1$ is hydrido, and $X^O$ is hydrido;

$R^2$ is 3-aminophenoxy, B is ethyl, A is single bond, $Y^O$ is 4-amidinobenzyl, $R^1$ is hydrido, and $X^O$ is hydrido;

$R^2$ is 3-aminophenoxy, B is ethyl, A is single bond, $Y^O$ is 4-amidino-2-fluorobenzyl, $R^1$ is hydrido, and $X^O$ is hydrido;

$R^2$ is 3-aminophenoxy, B is 2-propenyl, A is single bond, $Y^O$ is 4-amidinobenzyl, $R^1$ is hydrido, and $X^O$ is hydrido;

$R^2$ is 3-aminophenoxy, B is isopropyl, A is single bond, $Y^O$ is 4-amidino-2-fluorobenzyl, $R^1$ is hydrido, and $X^O$ is hydrido;

$R^2$ is 3-aminophenoxy, B is isopropyl, A is single bond, $Y^O$ is 4-amidinobenzyl, $R^1$ is hydrido, and $X^O$ is hydrido;

$R^2$ is 3-aminophenoxy, B is 2-butyl, A is single bond, $Y^O$ is 4-amidinobenzyl, $R^1$ is hydrido, and $X^O$ is hydrido;

$R^2$ is 3-aminophenoxy, B is (R)-2-butyl, A is single bond, $Y^O$ is 4-amidinobenzyl, $R^1$ is hydrido, and $X^O$ is hydrido;

$R^2$ is 3-aminophenoxy, B is 2-propynyl, A is single bond, $Y^O$ is 4-amidinobenzyl, $R^1$ is hydrido, and $X^O$ is hydrido;

$R^2$ is 3-aminophenoxy, B is 3-pentyl, A is single bond, $Y^O$ is 4-amidinobenzyl, $R^1$ is hydrido, and $X^O$ is hydrido;

$R^2$ is 3-aminophenoxy, B is hydrido, A is $CH_2$, $Y^O$ is 4-amidinobenzyl, $R^1$ is hydrido, and $X^O$ is hydrido;

$R^2$ is 3-aminophenoxy, B is ethyl, A is $CH_2$, $Y^O$ is 4-amidinobenzyl, $R^1$ is hydrido, and $X^O$ is hydrido;

$R^2$ is 3-aminophenoxy, B is 2-methylpropyl, A is single bond, $Y^O$ is 4-amidinobenzyl, $R^1$ is hydrido, and $X^O$ is hydrido;

$R^2$ is 3-aminophenoxy, B is 2-propyl, A is $CH_3CH$, $Y^O$ is 4-amidinobenzyl, $R^1$ is hydrido, and $X^O$ is hydrido;

$R^2$ is 3-aminophenoxy, B is propyl, A is single bond, $Y^0$ is 4-amidino-2-fluorobenzyl, $R^1$ is hydrido, and $X^O$ is hydrido;

$R^2$ is 3-aminophenoxy, B is 6-amidocarbonylhexyl, A is single bond, $Y^0$ is 4-amidinobenzyl, $R^1$ is hydrido, and $X^O$ is hydrido;

$R^2$ is 3-aminophenoxy, B is tert-butyl, A is single bond, $Y^0$ is 4-amidinobenzyl, $R^1$ is hydrido, and $X^O$ is hydrido;

$R^2$ is 3-aminophenoxy, B is tert-butyl, A is single bond, $Y^0$ is 4-amidinobenzyl, $R^1$ is hydrido, and $X^O$ is hydrido;

$R^2$ is 3-aminophenoxy, B is 3-hydroxypropyl, A is single bond, $Y^0$ is 4-amidinobenzyl, $R^1$ is hydrido, and $X^O$ is hydrido;

$R^2$ is 3-aminophenoxy, B is 2-methylpropyl, A is single bond, $Y^0$ is 4amidino-2-fluorobenzyl, $R^1$ is hydrido, and $X^O$ is hydrido;

$R^2$ is 3-aminophenoxy, B is butyl, A is single bond, $Y^0$ is 4-amidinobenzyl, $R^1$ is hydrido, and $X^O$ is hydrido;

$R^2$ is 3-aminophenoxy, B is 1-methoxy-2-propyl, A is single bond, $Y^0$ is 4-amidinobenzyl, $R^1$ is hydrido, and $X^O$ is hydrido;

$R^2$ is 3-aminophenoxy, B is 2-methoxyethyl, A is single bond, $Y^0$ is 4-amidinobenzyl, $R^1$ is hydrido, and $X^O$ is hydrido;

$R^2$ is 3-aminophenoxy, B is 2-propyl, A is single bond, $Y^0$ is 5-amidino-2-thienylmethyl, $R^1$ is hydrido, and $X^O$ is hydrido;

$R^2$ is 3-aminophenoxy, B is 2-propyl, A is single bond, $Y^0$ is 4-amidino-3-fluorobenzyl, $R^1$ is hydrido, and $X^O$ is hydrido;

$R^2$ is 3-carboxyphenoxy, B is 2-propyl, A is single bond, $Y^0$ is 4-amidinobenzyl, $R^1$ is hydrido, and $X^O$ is hydrido;

$R^2$ is 3-aminophenoxy, B is 2-propyl, A is single bond, $Y^0$ is 4-amidino-3-fluorobenzyl, $R^1$ is hydrido, and $X^O$ is hydrido;

$R^2$ is 3-amino-carboxy-2-thienyl, B is 2,2,2-trifluoroethyl, A is single bond, $Y^0$ is 4-amidinobenzyl, $R^1$ is hydrido, and $X^O$ is hydrido;

$R^2$ is 3-amino-5-carboxy-2-thienyl, B is (S)-2-butyl, A is single bond, $Y^0$ is 4-amidinobenzyl, $R^1$ is hydrido, and $X^O$ is hydrido;

$R^2$ is 5-amino-4-fluoro-3-carboxy-2-thienyl, B is isopropyl, A is single bond, $Y^0$ is 4-amidinobenzyl, $R^1$ is hydrido, and $X^O$ is hydrido;

$R^2$ is 4-methyl-3-amino-5-carboxy-2-thienyl, B is isopropyl, A is single bond, $Y^0$ is 4-amidinobenzyl, $R^1$ is hydrido, and $X^O$ is hydrido;

$R^2$ is 3-amino-5-carboxy-2-thienyl, B is ethyl, A is single bond, $Y^0$ is 4-amidinobenzyl, $R^1$ is hydrido, and $X^O$ is hydrido;

$R^2$ is 3-amino-5-carboxy-2-thienyl, B is ethyl, A is single bond, $Y^0$ is 4-amidino-2-fluorobenzyl, $R^1$ is hydrido, and $X^O$ is hydrido;

$R^2$ is 3-amino-5-carboxy-2-thienyl, B is 2-propenyl, A is single bond, $Y^0$ is 4-amidinobenzyl, $R^1$ is hydrido, and $X^O$ is hydrido;

$R^2$ is 3-amino-5-carboxy-2-thienyl, B is isopropyl, A is single bond, $Y^0$ is 4-amidino-2-fluorobenzyl, $R^1$ is hydrido, and $X^O$ is hydrido;

$R^2$ is 3-amino-5-carboxy-2-thienyl, B is isopropyl, A is single bond, $Y^0$ is 4-amidinobenzyl, $R^1$ is hydrido, and $X^O$ is hydrido;

$R^2$ is 3-amino-5-carboxy-2-thienyl, B is 2-butyl, A is single bond, $Y^0$ is 4-amidinobenzyl, $R^1$ is hydrido, and $X^O$ is hydrido;

$R^2$ is 3-amino-5-carboxy-2-thienyl, B is (R)-2-butyl, A is single bond, $Y^0$ is 4-amidinobenzyl, $R^1$ is hydrido, and $X^O$ is hydrido;

$R^2$ is 3-amino-5-carboxy-2-thienyl, B is 2-propynyl, A is single bond, $Y^0$ is 4-amidinobenzyl, $R^1$ is hydrido, and $X^O$ is hydrido;

$R^2$ is 3-amino-5-carboxy-2-thienyl, B is 3-pentyl, A is single bond, $Y^0$ is 4-amidinobenzyl, $R^1$ is hydrido, and $X^O$ is hydrido;

$R^2$ is 3-amino-5-carboxy-2-thienyl, B is hydrido, A is $CH_2$, $Y^0$ is 4-amidinobenzyl, $R^1$ is hydrido, and $X^O$ is hydrido;

$R^2$ is 3-amino-5-carboxy-2-thienyl, B is ethyl, A is $CH_2$, $Y^0$ is 4-amidinobenzyl, $R^1$ is hydrido, and $X^O$ is hydrido;

$R^2$ is 3-amino-5-carboxy-2-thienyl, B is 2-methylpropyl, A is single bond, $Y^0$ is 4-amidinobenzyl, $R^1$ is hydrido, and $X^O$ is hydrido;

$R^2$ is 3-amino-5-carboxy-2-thienyl, B is 2-propyl, A is $CH_3CH$, $Y^9$ is 4-amidinobenzyl, $R^1$ is hydrido, and $X^O$ is hydrido;

$R^2$ is 3-amino-5-carboxy-2-thienyl, B is propyl, A is single bond, $Y^0$ is 4-amidino-2-fluorobenzyl, $R^1$ is hydrido, and $X^O$ is hydrido;

$R^2$ is 3-amino-5-carboxy-2-thienyl, B is 6-amidocarbonylhexyl, A is single bond, $Y^0$ is 4-amidinobenzyl, $R^1$ is hydrido, and $X^O$ is hydrido;

$R^2$ is 3-amino-5-carboxy-2-thienyl, B is tert-butyl, A is single bond, $Y^0$ is 4-amidinobenzyl, $R^1$ is hydrido, and $X^O$ is hydrido;

$R^2$ is 3-amino-5-carboxy-2-thienyl, B is tert-butyl, A is single bond, $Y^0$ is 4-amidinobenzyl, $R^1$ is hydrido, and $X^O$ is hydrido;

$R^2$ is 3-amino-5-carboxy-2-thienyl, B is 3-hydroxypropyl, A is single bond, $Y^0$ is 4-amidinobenzyl, $R^1$ is hydrido, and $X^O$ is hydrido;

$R^2$ is 3-amino-5-carboxy-2-thienyl, B is 2-methylpropyl, A is single bond, $Y^0$ is 4-amidino-2-fluorobenzyl, $R^1$ is hydrido, and $X^O$ is hydrido;

$R^2$ is 3-amino-5-carboxy-2-thienyl, B is butyl, A is single bond, $Y^0$ is 4-amidinobenzyl, $R^1$ is hydrido, and $X^O$ is hydrido;

$R^2$ is 3-amino-5-carboxy-2-thienyl, B is 1-methoxy-2-propyl, A is single bond, $Y^0$ is 4-amidinobenzyl, $R^1$ is hydrido, and $X^O$ is hydrido;

$R^2$ is 3-amino-5-carboxy-2-thienyl, B is 2-methoxyethyl, A is single bond, $Y^0$ is 4-amidinobenzyl, $R^1$ is hydrido, and $X^O$ is hydrido;

$R^2$ is 3-amino-5-carboxy-2-thienyl, B is 2-propyl, A is single bond, $Y^0$ is 4-amidino-2-thienylmethyl, $R^1$ is hydrido, and $X^O$ is hydrido;

$R^2$ is 3-amino-5-carboxy-2-thienyl, B is 2-propyl, A is single bond, $Y^0$ is 4-amidino-3-fluorobenzyl, $R^1$ is hydrido, and $X^O$ is hydrido;

$R^2$ is 3-amino-5carboxy-2-thienyl, B is 2-propyl, A is single bond, $Y^0$ is 4-amidinobenzyl, $R^1$ is hydrido, and $X^O$ is hydrido;

$R^{is}$ 3-amino-5-carboxy-2-thienyl, B is 2-propyl, A is single bond, $Y^0$ is 4-amidino-3-fluorobenzyl, $R^1$ is hydrido, and $X^O$ is hydrido;

$R^2$ is 3-amino-5-carboxyphenylthio, B is 2,2,2-trifluoroethyl, A is single bond, $Y^0$ is 4-amidinobenzyl, $R^1$ is hydrido, and $X^O$ is hydrido;

$R^2$ is 3-amino-5-carboxyphenylthio, B is (S)-2-butyl, A is single bond, $Y^0$ is 4amidinobenzyl, $R^1$ is hydrido, and $X^O$ is hydrido;

$R^2$ is 5-amino-2-fluoro-5-carboxyphenylthio, B is isopropyl, A is single bond, $Y^0$ is 4-amidinobenzyl, $R^1$ is hydrido, and $X^O$ is hydrido;

$R^2$ is 2-methyl-3-amino-5-carboxyphenylthio, B is isopropyl, A is single bond, $Y^0$ is 4-amidinobenzyl, $R^1$ is hydrido, and $X^O$ is hydrido;

$R^2$ is 3-amino-5-carboxyphenylthio, B is ethyl, A is single bond, $Y^0$ is 4-amidinobenzyl, $R^1$ is hydrido, and $X^O$ is hydrido;

$R^2$ is 3-amino-5-carboxyphenylthio, B is ethyl, A is single bond, $Y^0$ is 4-amidino-2-fluorobenzyl, $R^1$ is hydrido, and $X^O$ is hydrido;

$R^2$ is 3-amino-5-carboxyphenylthio, B is 2-propenyl, A is single bond, $Y^0$ is 4-amidinobenzyl, $R^1$ is hydrido, and $X^O$ is hydrido;

$R^2$ is 3-amino-5-carboxyphenylthio, B is isopropyl, A is single bond, $Y^0$ is 4-amidino-2-fluorobenzyl, $R^1$ is hydrido, and $X^O$ is hydrido;

$R^2$ is 3-amino-5-carboxyphenylthio, B is isopropyl, A is single bond, $Y^0$ is 4-amidinobenzyl, $R^1$ is hydrido, and $X^O$ is hydrido;

$R^2$ is 3-amino-5-carboxyphenylthio, B is 2-butyl, A is single bond, $Y^0$ is 4-amidinobenzyl, $R^1$ is hydrido, and $X^O$ is hydrido;

$R^2$ is 3-amino-5-carboxyphenylthio, B is (R)-2-butyl, A is single bond, $Y^0$ is 4-amidinobenzyl, $R^1$ is hydrido, and $X^O$ is hydrido;

$R^2$ is 3-amino-5-carboxyphenylthio, B is 2-propynyl, A is single bond, $Y^0$ is 4-amidinobenzyl, $R^1$ is hydrido, and $X^O$ is hydrido;

$R^2$ is 3-amino-5-carboxyphenylthio, B is 3-pentyl, A is single bond, $Y^0$ is 4-amidinobenzyl, $R^1$ is hydrido, and $X^O$ is hydrido;

$R^2$ is 3-amino-5-carboxyphenylthio, B is hydrido, A is $CH_2$, $Y^0$ is 4-amidinobenzyl, $R^1$ is hydrido, and $X^O$ is hydrido;

$R^2$ is 3-amino-5-carboxyphenylthio, B is ethyl, A is $CH_2$, $Y^0$ is 4-amidinobenzyl, $R^1$ is hydrido, and $X^O$ is hydrido;

$R^2$ is 3-amino-5-carboxyphenylthio, B is 2-methylpropyl, A is single bond, $Y^0$ is 4-amidinobenzyl, $R^1$ is hydrido, and $X^O$ is hydrido;

$R^2$ is 3-amino-5-carboxyphenylthio, B is 2-propyl, A is $CH_3CH$, $Y^0$ is 4-amidinobenzyl, $R^1$ is hydrido, and $X^O$ is hydrido;

$R^2$ is 3-amino-5-carboxyphenylthio, B is propyl, A is single bond, $Y^0$ is 4-amidino-2-fluorobenzyl, $R^1$ is hydrido, and $X^O$ is hydrido;

$R^2$ is 3-amino-5-carboxyphenylthio, B is 6-amidocarbonylhexyl, A is single bond, $Y^0$ is 4-amidinobenzyl, $R^1$ is hydrido, and $X^O$ is hydrido;

$R^2$ is 3-amino-5-carboxyphenylthio, B is tert-butyl, A is single bond, $Y^0$ is 4-amidinobenzyl, $R^1$ is hydrido, and $X^O$ is hydrido;

$R^2$ is 3-amino-5-carboxyphenylthio, B is tert-butyl, A is single bond, $Y^0$ is 4-amidinobenzyl, $R^1$ is hydrido, and $X^O$ is hydrido;

$R^2$ is 3-amino-5-carboxyphenylthio, B is 3-hydroxypropyl, A is single bond, $Y^0$ is 4-amidinobenzyl, $R^1$ is hydrido, and $X^O$ is hydrido;

$R^2$ is 3-amino-5-carboxyphenylthio, B is 2-methylpropyl, A is single bond, $Y^0$ is 4-amidino-2-fluorobenzyl, $R^1$ is hydrido, and $X^O$ is hydrido;

$R^2$ is 3-amino-5-carboxyphenylthio, B is butyl, A is single bond, $Y^0$ is 4-amidinobenzyl, $R^1$ is hydrido, and $X^O$ is hydrido;

$R^2$ is 3-amino-5-carboxyphenylthio, B is 1-methoxy-2-propyl, A is single bond, $Y^0$ is 4-amidinobenzyl, $R^1$ is hydrido, and $X^O$ is hydrido;

$R^2$ is 3-amino-5-carboxyphenylthio, B is 2-methoxyethyl, A is single bond, $Y^0$ is 4-amidinobenzyl, $R^1$ is hydrido, and $X^O$ is hydrido;

$R^2$ is 3-amino-5-carboxyphenylthio, B is 2-propyl, A is single bond, $Y^0$ is 5-amidino-2-thienylmethyl, $R^1$ is hydrido, and $X^O$ is hydrido;

$R^2$ is 3-amino-5-carboxyphenylthio, B is 2-propyl, A is single bond, $Y^0$ is 4-amidino-3-fluorobenzyl, $R^1$ is hydrido, and $X^O$ is hydrido;

$R^2$ is 3-carboxy-5-carboxyphenylthio, B is 2-propyl, A is single bond, $Y^0$ is 4-amidinobenzyl, $R^1$ is hydrido, and $X^O$ is hydrido;

$R^2$ is 3-amino-5-carboxyphenylthio, B is 2-propyl, A is single bond, $Y^0$ is 4-amidino-3-fluorobenzyl, $R^1$ is hydrido, and $X^O$ is hydrido;

$R^2$ is 3-amidocarbonyl-5-aminophenoxy, B is 2-propyl, A is single bond, $Y^0$ is 4-amidinobenzyl, $R^1$ is chloro, and $X^O$ is hydrido;

$R^2$ is 3-amino-5-(N-benzylamidocarbonyl)phenoxy, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl)phenoxy, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)phenoxy, B is 2-propyl, A is single bond, $Y^0$ is 4-amidinobenzyl, $R^1$ is chloro, and $X^O$ is hydrido;

$R^2$ is 3-amino5-(N-(2-trifluoromethylbenzyl)amidocarbonyl)-phenoxy, B is 2-propyl, A is single bond, $Y^0$ is 4-amidinobenzyl, $R^1$ is chloro, and $X^O$ is hydrido;

$R^2$ is 3,5-diaminophenoxy, B is 2-propyl, A is single bond, $Y^0$ is 4-amidinobenzyl, $R^1$ is chloro, and $X^O$ is hydrido;

$R^{is}$ 3-amino-5-carboxyphenoxy, B is 2-propyl, A is single bond, $Y^0$ is 4-amidinobenzyl, $R^1$ is chloro, and $X^O$ is hydrido;

$R^2$ is 3-amidocarbonyl-5-aminophenoxy, B is 2-propyl, A is single bond, $Y^0$ is 4-amidinobenzyl, $R^1$ is hydrido, and $X^O$ is hydrido;

$R^2$ is 3-amino-5-(N-benzylamidocarbonyl)phenoxy, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)phenoxy, B is 2-propyl, A is single bond, $Y^0$ is 4-amidinobenzyl, $R^1$ is hydrido, and $X^O$ is hydrido:

$R^2$ is 3-amino-5-(N-(2-chlorobenzyl)amidosulfonyl)phenoxy B is 2-propyl, A is single bond, $Y^0$ is 4-amidinobenzyl $R^1$ is hydrido, and $X^O$ is hydrido;

$R^2$ is 3-amino-5-(N-(2-trifluoromethylbenzyl)amidocarbonyl)phenoxy, B is 2-propyl, A is single bond, $Y^0$ is 4-amidinobenzyl, $R^1$ is hydrido, and $X^O$ is hydrido;

$R^2$ is 3,5-diaminophenoxy, B is 2-propyl, A is single bond, $Y^0$ is 4-amidinobenzyl, $R^1$ is hydrido, and $X^O$ is hydrido;

$R^2$ is 3-amino-5-carboxyphenoxy, B is 2-propyl, A is single bond, $Y^0$ is 4-amidinobenzyl, $R^1$ is hydrido, and $X^O$ is hydrido;

$R^2$ is 3-amidocarbonyl-5-amino-2-thienyl, B is 2-propyl, A is single bond, $Y^0$ is 4-amidinobenzyl, $R^1$ is chloro, and $X^O$ is hydrido;

$R^2$ is 3-amino-5-(N-benzylamidocarbonyl)-2-thienyl, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl)-2-thienyl, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)-2-thienyl, B is 2-propyl, A is single bond, $Y^0$ is 4-amidinobenzyl, $R^1$ is chloro, and $X^O$ is hydrido;

$R^2$ is 3-amino-5-(N-(2-trifluoromethylbenzyl)amidocarbonyl)-2-thienyl, B is 2-propyl, A is single bond, $Y^0$ is 4-amidinobenzyl, $R^1$ is chloro, and $X^O$ is hydrido;

$R^2$ is 3,5-diamino-2-thienyl, B is 2-propyl, A is single bond, $Y^0$ is 4-amidinobenzyl, $R^1$ is chloro, and $X^O$ is hydrido;

$R^2$ is 3-amino-5-carboxy-2-thienyl, B is 2-propyl, A is single bond, $Y^0$ is 4-amidinobenzyl, $R^1$ is chloro, and $X^O$ is hydrido;

$R^2$ is 3-amidocarbonyl-5-amino-2-thienyl, B is 2-propyl, A is single bond, $Y^0$ is 4-amidinobenzyl, $R^1$ is hydrido, and $X^O$ is hydrido;

$R^2$ is 3-amino-5-(N-benzylamidocarbonyl)-2-thienyl, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)-2-thienyl, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl)-2-thienyl B is 2-propyl, A is single bond, $Y^0$ is 4-amidinobenzyl $R^1$ is hydrido, and $X^O$ is hydrido;

$R^2$ is 3-amino-5-(N-(2-trifluoromethylbenzyl)amidocarbonyl)-2-thienyl, B is 2-propyl, A is single bond, $Y^0$ is 4-amidinobenzyl, $R^1$ is hydrido, and $X^O$ is hydrido;

$R^2$ is 3,5-diamino-2-thienyl, B is 2-propyl, A is single bond, $Y^0$ is 4-amidinobenzyl, $R^1$ is hydrido, and $X^O$ is hydrido;

$R^2$ is 3-amino-5-carboxy-2-thienyl, B is 2-propyl, A is single bond, $Y^0$ is 4-amidinobenzyl, $R^1$ is hydrido, and $X^O$ is hydrido;

$R^2$ is 3-amidocarbonyl-5-aminophenylthio, B is 2-propyl, A is single bond, $Y^0$ is 4-amidinobenzyl, $R^1$ is chloro, and $X^O$ is hydrido;

$R^2$ is 3-amino-5-(N-benzylamidocarbonyl)phenylthio, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl)phenylthio, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)phenylthio, B is 2-propyl, A is single bond, $Y^0$ is 4-amidinobenzyl, $R^1$ is chloro, and $X^O$ is hydrido;

$R^2$ is 3-amino-5-(N-(2-trifluoromethylbenzyl)amidocarbonyl)phenylthio, B is 2-propyl, A is single bond, $Y^0$ is 4-amidinobenzyl, $R^1$ is chloro, and $X^O$ is hydrido;

$R^2$ is 3,5-diaminophenylthio, B is 2-propyl, A is single bond, $Y^0$ is 4-amidinobenzyl, $R^1$ is chloro, and $X^O$ is hydrido;

$R^2$ is 3-amino-5-carboxyphenylthio, B is 2-propyl, A is single bond, $Y^0$ is 4-amidinobenzyl, $R^1$ is chloro, and $X^O$ is hydrido;

$R^2$ is 3-amidocarbonyl-5-aminophenylthio, B is 2-propyl, A is single bond, $Y^0$ is 4-amidinobenzyl, $R^1$ is hydrido, and $X^O$ is hydrido;

$R^2$ is 3-amino-5-(N-benzylamidocarbonyl)phenylthio, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)phenylthio, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl)phenylthio B is 2-propyl, A is single bond, $Y^0$ is 4-amidinobenzyl, $R^1$ is hydrido, and $X^O$ is hydrido;

$R^2$ is 3-amino-5-(N-(2-trifluoromethylbenzyl)amidocarbonyl)phenylthio, B is 2-propyl, A is single bond, $Y^0$ is 4-amidinobenzyl, $R^1$ is hydrido, and $X^O$ is hydrido;

$R^2$ is 3,5-diaminophenylthio, B is 2-propyl, A is single bond, $Y^0$ is 4-amidinobenzyl, $R^1$ is hydrido, and $X^O$ is hydrido;

$R^2$ is 3-amino-5-carboxyphenylthio, B is 2-propyl, A is single bond, $Y^0$ is 4-amidinobenzyl, $R^1$ is hydrido, and $X^O$ is hydrido;

$R^2$ is 3-aminophenoxy, B is cyclopropyl, A is single bond, $Y^0$ is 4-amidinobenzyl, $R^1$ is aminomethyl, and $X^O$ is hydrido;

$R^2$ is 3-aminophenoxy, B is cyclobutyl, A is single bond, $Y^0$ is 4-amidino-2-fluorobenzyl, $R^1$ is aminomethyl, and $X^O$ is hydrido;

$R^2$ is 3-aminophenoxy, B is cyclobutyl, A is single bond, $Y^0$ is 4-amidinobenzyl, $R^1$ is aminomethyl, and $X^O$ is hydrido;

$R^2$ is 3-aminophenoxy, B is cyclopropyl, A is single bond, $Y^0$ is 4-amidino2-fluorobenzyl, $R^1$ is aminomethyl, and $X^O$ is hydrido;

$R^2$ is 3-aminophenoxy, B is cyclobutyl, A is single bond, $Y^0$ is 4-amidinobenzyl, $R^1$ is aminomethyl, and $X^O$ is hydrido;

$R^2$ is 3-aminophenoxy, B is cyclobutyl, A is single bond, $Y^0$ is 4-amidino3-fluorobenzyl, $R^1$ is aminomethyl, and $X^O$ is hydrido;

$R^2$ is 3-aminophenoxy, B is cyclopentyl, A is single bond, $Y^0$ is 4-amidinobenzyl, $R^1$ is aminomethyl, and $X^O$ is hydrido;

$R^2$ is 3-aminophenoxy, B is cyclopropyl, A is $CH_2$, $Y^0$ is 4-amidinobenzyl, $R^1$ is aminomethyl, and $X^O$ is hydrido;

$R^2$ is 3-aminophenoxy, B is 2-(2R)-bicyclo[2.2.1]-heptyl, A is single bond, $Y^0$ is 4-amidinobenzyl, $R^1$ is aminomethyl, and $X^O$ is hydrido;

$R^2$ is 3-aminophenoxy, B is cyclopentyl, A is single bond, $Y^0$ is 4-amidino-2-fluorobenzyl, $R^1$ is aminomethyl, and $X^O$ is hydrido;

$R^2$ is 3-aminophenoxy, B is cyclohexyl, A is $CH_2CH_2$, $Y^0$ is 4-amidinobenzyl, $R^1$ is aminomethyl, and $X^O$ is hydrido;

$R^2$ is 2-hydroxyphenoxy, B is cyclobutyl, A is single bond, $Y^0$ is 4-amidinobenzyl, $R^1$ is aminomethyl, and $X^O$ is hydrido;

$R^2$ is phenoxy, B is cyclobutyl, A is single bond, $Y^0$ is 4-amidinobenzyl, $R^1$ is aminomethyl, and $X^O$ is hydrido;

$R^2$ is 2,6-dichlorophenoxy, B is cyclobutyl, A is single bond, $Y^0$ is 4-amidinobenzyl, $R^1$ is aminomethyl, and $X^O$ is hydrido;

$R^2$ is 3-aminophenoxy, B is cyclopropyl, A is single bond, $Y^0$ is 4-amidinobenzyl, $R^1$ is chloro, and $X^O$ is hydrido;

$R^2$ is 3-aminophenoxy, B is cyclobutyl, A is single bond, $Y^0$ is 4-amidino-2-fluorobenzyl, $R^1$ is chloro, and $X^O$ is hydrido;

$R^2$ is 3-aminophenoxy, B is cyclobutyl, A is single bond, $Y^0$ is 4-amidinobenzyl, $R^1$ is chloro, and $X^O$ is hydrido;

$R^2$ is 3-aminophenoxy, B is cyclopropyl, A is single bond, $Y^0$ is 4-amidino2-fluorobenzyl, $R^1$ is chloro, and $X^O$ is hydrido;

$R^2$ is 3-aminophenoxy, B is cyclobutyl, A is single bond, $Y^0$ is 4-amidinobenzyl, $R^1$ is chloro, and $X^O$ is hydrido;

$R^2$ is 3-aminophenoxy, B is cyclobutyl, A is single bond, $Y^0$ is 4amidino-3-fluorobenzyl, $R^1$ is chloro, and $X^O$ is hydrido;

$R^2$ is 3-aminophenoxy, B is cyclopentyl, A is single bond, $Y^0$ is 4-amidinobenzyl, $R^1$ is chloro, and $X^O$ is hydrido;

$R^{is}$ 3-aminophenoxy, B is cyclopropyl, A is $CH_2$, $Y^0$ is 4-amidinobenzyl, $R^1$ is chloro, and $X^O$ is hydrido;

$R^2$ is 3-aminophenoxy, B is 2-(2R)-bicyclo[2.2.1]-heptyl, A is single bond, $Y^0$ is 4-amidinobenzyl, $R^1$ is chloro, and $X^O$ is hydrido;

$R^2$ is 3-aminophenoxy, B is cyclopentyl, A is single bond, $Y^0$ is 4-amidino-2-fluorobenzyl, $R^1$ is chloro, and $X^O$ is hydrido;

$R^2$ is 3-aminophenoxy, B is cyclohexyl, A is $CH_2CH_2$, $Y^0$ is 4-amidinobenzyl, $R^1$ is chloro, and $X^O$ is hydrido;

$R^2$ is 2-hydroxyphenoxy, B is cyclobutyl, A is single bond, $Y^0$ is 4-amidinobenzyl, $R^1$ is chloro, and $X^O$ is hydrido;

$R^2$ is phenoxy, B is cyclobutyl, A is single bond, $Y^0$ is 4-amidinobenzyl, $R^1$ is chloro, and $X^O$ is hydrido;

$R^2$ is 2,6-dichlorophenoxy, B is cyclobutyl, A is single bond, $Y^0$ is 4-amidinobenzyl, $R^1$ is chloro, and $X^O$ is hydrido;

$R^2$ is 3-amidocarbonyl-5-aminophenoxy, B is cyclobutyl, A is single bond, $Y^0$ is 4-amidinobenzyl, $R^1$ is chloro, and $X^O$ is hydrido;

$R^2$ is 3-amino-5-(N-benzylamidocarbonyl)phenoxy, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl)phenoxy, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)phenoxy, B is cyclobutyl, A is single bond, $Y^0$ is 4-amidinobenzyl, $R^1$ is chloro, and $X^O$ is hydrido;

$R^2$ is 3-amino-5N-(2-trifluoromethylbenzyl)amidocarbonyl)-phenoxy, B is cyclobutyl, A is single bond, $Y^0$ is 4-amidinobenzyl, $R^1$ is chloro, and $X^O$ is hydrido;

$R^2$ is 3,5-diaminophenoxy, B is cyclobutyl, A is single bond, $Y^0$ is 4-amidinobenzyl, $R^1$ is chloro, and $X^O$ is hydrido;

$R^2$ is 3-amino-5-carboxyphenoxy, B is cyclobutyl, A is single bond, $Y^0$ is 4-amidinobenzyl, $R^1$ is chloro, and $X^O$ is hydrido;

$R^2$ is 3-amidocarbonyl-5-aminophenoxy, B is cyclobutyl, A is single bond, $Y^0$ is 4-amidinobenzyl, $R^1$ is hydrido, and $X^O$ is hydrido;

$R^2$ is 3-amino-5-(N-benzylamidocarbonyl)phenoxy, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)phenoxy, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl)phenoxy, B is cyclobutyl, A is single bond, $Y^0$ is 4-amidinobenzyl $R^1$ is hydrido, and $X^O$ is hydrido;

$R^2$ is 3-amino-5-(N-(2-trifluoromethylbenzyl)amidocarbonyl)phenoxy, B is cyclobutyl, A is single bond, $Y^0$ is 4-amidinobenzyl, $R^1$ is hydrido, and $X^O$ is hydrido;

$R^2$ is 3,5-diaminophenoxy, B is cyclobutyl, A is single bond, $Y^0$ is 4-amidinobenzyl, $R^1$ is hydrido, and $X^O$ is hydrido;

$R^2$ is 3-amino-5-carboxyphenoxy, B is cyclobutyl, A is single bond, $Y^0$ is 4-amidinobenzyl, $R^1$ is hydrido, and $X^O$ is hydrido;

$R^2$ is 3-amidocarbonyl-5-aminophenylthio, B is cyclobutyl, A is single bond, $Y^0$ is 4-amidinobenzyl, $R^1$ is chloro, and $X^O$ is hydrido;

$R^2$ is 3-amino-5-(N-benzylamidocarbonyl)phenylthio, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl)phenylthio, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)phenylthio, B is cyclobutyl, A is single bond, $Y^0$ is 4-amidinobenzyl, $R^1$ is chloro, and $X^O$ is hydrido;

$R^2$ is 3-amino-5-(N-2-trifluoromethylbenzyl)amidocarbonyl)phenylthio, B is cyclobutyl, A is single bond, $Y^0$ is 4-amidinobenzyl, $R^1$ is chloro, and $X^O$ is hydrido;

$R^2$ is 3,5-diaminophenylthio, B is cyclobutyl, A is single bond, $Y^0$ is 4-amidinobenzyl, $R^1$ is chloro, and $X^O$ is hydrido;

$R^2$ is 3-amino-5-carboxyphenylthio, B is cyclobutyl, A is single bond, $Y^0$ is 4-amidinobenzyl, $R^1$ is chloro, and $X^O$ is hydrido;

$R^2$ is 3-amidocarbonyl-5-aminophenylthio, B is cyclobutyl, A is single bond, $Y^0$ is 4-amidinobenzyl, $R^1$ is hydrido, and $X^O$ is hydrido;

$R^2$ is 3-amino-5-(N-benzylamidocarbonyl)phenylthio, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)phenylthio, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl)phenylthio, B is cyclobutyl, A is single bond, $Y^0$ is 4-amidinobenzyl $R^1$ is hydrido, and $X^O$ is hydrido;

$R^2$ is 3-amino-5-(N-(2-trifluoromethylbenzyl)amidocarbonyl)phenylthio, B is cyclobutyl, A is single bond, $Y^0$ is 4-amidinobenzyl, $R^1$ is hydrido, and $X^O$ is hydrido;

$R^2$ is 3,5-diaminophenylthio, B is cyclobutyl, A is single bond, $Y^0$ is 4-amidinobenzyl, $R^1$ is hydrido, and $X^O$ is hydrido;

$R^2$ is 3-amino-5-carboxyphenylthio, B is cyclobutyl, A is single bond, $Y^0$ is 4-amidinobenzyl, $R^1$ is hydrido, and $X^O$ is hydrido;

$R^2$ is 3-amidocarbonyl-5-amino-2-thienyl, B is cyclobutyl, A is single bond, $Y^0$ is 4-amidinobenzyl, $R^1$ is chloro, and $X^O$ is hydrido;

$R^2$ is 3-amino-5-(N-benzylamidocarbonyl)-2-thienyl, B is cyclobutyl, A is single bond, $Y^0$ is 4-aminobenzyl, $R^1$ is chloro, and $X^O$ is hydrido;

$R^2$ is 3-amino-5-(N-(2-chlorobenzyl)amidocarbonyl)-2-thienyl, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)-2-thienyl, B is cyclobutyl, A is single bond, $Y^0$ is 4-amidinobenzyl, $R^1$ is chloro, and $X^O$ is hydrido;

$R^2$ is 3-amino-5-(N-(2-trifluoromethylbenzyl)amidocarbonyl)-2-thienyl, B is cyclobutyl, A is single bond, $Y^0$ is 4-amidinobenzyl, $R^1$ is chloro, and $X^O$ is hydrido;

$R^2$ is 3,5-diamino-2-thienyl, B is cyclobutyl, A is single bond, $Y^0$ is 4-amidinobenzyl, $R^1$ is chloro, and $X^O$ is hydrido;

$R^2$ is 3-amino-5-carboxy-2-thienyl, B is cyclobutyl, A is single bond, $Y^0$ is 4-amidinobenzyl, $R^1$ is chloro, and $X^O$ is hydrido;

$R^2$ is 3-amidocarbonyl-5-amino-2-thienyl, B is cyclobutyl, A is single bond, $Y^0$ is 4-amidinobenzyl, $R^1$ is hydrido, and $X^O$ is hydrido;

$R^2$ is 3-amino-5-(N-benzylamidocarbonyl)-2-thienyl, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)-2-thienyl, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl)-2-thienyl, B is cyclobutyl, A is single bond, $Y^0$ is 4-amidinobenzyl $R^1$ is hydrido, and $X^O$ is hydrido;

$R^2$ is 3-amino-5-(N-(2-trifluoromethylbenzyl)amidocarbonyl)-2-thienyl, B is cyclobutyl, A is single bond, $Y^0$ is 4-amidinobenzyl, $R^1$ is hydrido, and $X^O$ is hydrido;

$R^2$ is 3,5-diamino-2-thienyl, B is cyclobutyl, A is single bond, $Y^0$ is 4-amidinobenzyl, $R^1$ is hydrido, and $X^O$ is hydrido;

$R^2$ is 3-amino-5-carboxy-2-thienyl, B is cyclobutyl, A is single bond, is 4-amidinobenzyl, $R^1$ is hydrido, and $X^O$ is hydrido;

$R^2$ is 3-aminophenyl, B is 3-chlorophenyl, A is $CH_2CH_2$, $Y^0$ is 4-amidinobenzyl, $R^1$ is hydrido, and $X^O$ is hydrido;

$R^2$ is 3-aminophenyl, B is phenyl, A is $CH_2$, $Y^0$ is 4-amidinobenzyl, $R^1$ is hydrido, and $X^O$ is hydrido;

$R^2$ is phenyl, B is 3-chlorophenyl, A is $CH_2CH_2$, $Y^0$ is 4-amidinobenzyl, $R^1$ is hydrido, and $X^O$ is hydrido;

$R^2$ is 3-dimethylaminophenyl, B is phenyl, A is $CH_2CH_2$, $Y^0$ is 4-amidinobenzyl, $R^1$ is hydrido, and $X^O$ is hydrido;

$R^2$ is 2-methylphenyl, B is phenyl, A is $CH_2CH_2$, $Y^O$ is 4-amidinobenzyl, $R^1$ is hydrido, and $X^O$ is hydrido;

$R^2$ is phenyl, B is 3-aminophenyl, A is C(O)NH, $Y^O$ is 4-amidinobenzyl, $R^1$ is hydrido, and $X^O$ is hydrido;

$R^2$ is 3-amidocarbonyl-5-aminophenyl, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-benzylamidocarbonyl)phenyl, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-(2-chlorobenzyl)amidocarbonyl)phenyl, B is 3-chlorophenyl, A is $CH_2CH_2$, $Y^O$ is 4-amidinobenzyl, $R^1$ is chloro, and $X^O$ is hydrido;

$R^2$ is 3-amino-5-(N-(2-chlorobenzyl)amidosulfonyl)phenyl, B is 3-chlorophenyl, A is $CH_2CH_2$, $Y^O$ is 4-amidinobenzyl, $R^1$ is chloro,;and $X^O$ is hydrido;

$R^2$ is 3-amino-5-(N-(2-trifluoromethylbenzyl)amidocarbonyl)-phenyl, B is 3-chlorophenyl, A is $CH_2CH_2$, $Y^O$ is 4-amidinobenzyl, $R^1$ is chloro, and $X^O$ is hydrido;

$R^2$ is 3,5-diaminophenyl, B is 3-chlorophenyl, A is $CH_2CH_2$, $Y^O$ is 4-amidinobenzyl, $R^1$ is chloro, and $X^O$ is hydrido;

$R^2$ is 3-amino-5-carboxyphenyl, B is 3-chlorophenyl, A is $CH_2CH_2$, $Y^O$ is 4-amidinobenzyl, $R^1$ is chloro, and $X^O$ is hydrido;

$R^2$ is 3-amidocarbonyl-5-aminophenyl, B is 3-chlorophenyl, A is $CH_2CH_2$, is 4-amidinobenzyl, $R^1$ is hydrido, and $X^O$ is hydrido;

$R^2$ is 3-amino-5-(N-benzylamidocarbonyl)phenyl, B is 3-chlorophenyl, A is $CH_2CH_2$, $Y^O$ is 4-amidinobenzyl, $R^1$ is hydrido, and $X^O$ is hydrido;

$R^2$ is 3-amino-5-(N-(2-chlorobenzyl)amidocarbonyl)phenyl, B is 3-chlorophenyl, A is $CH_2CH_2$, $Y^O$ is 4-amidinobenzyl, $R^1$ is hydrido, and $X^O$ is hydrido;

$R^2$ is 3-amino-5-(N-(2-chlorobenzyl)amidosulfonyl)phenyl, B is 3-chlorophenyl, A is $CH_2CH_2$, $Y^O$ is 4-amidinobenzyl $R^1$ is hydrido, and $X^O$ is hydrido;

$R^2$ is 3-amino-5-(N-(2-trifluoromethylbenzyl)amidocarbonyl)phenyl, B is 3-chlorophenyl, A is $CH_2CH_2$, $Y^O$ is 4-amidinobenzyl, $R^1$ is hydrido, and $X^O$ is hydrido;

$R^2$ is 3,5-diaminophenyl, B is 3-chlorophenyl, A is $CH_2CH_2$, $Y^O$ is 4-amidinobenzyl, $R^1$ is hydrido, and $X^O$ is hydrido;

$R^2$ is 3-amino-5-carboxyphenyl, B is 3-chlorophenyl, A is $CH_2CH_2$, $Y^O$ is 4-amidinobenzyl, $R^1$ is hydrido, and $X^O$ is hydrido;

$R^2$ is 3-aminophenyl, B is 2,2,2-trifluoroethyl, A is single bond, $Y^O$ is 4-amidinobenzyl, $R^1$ is hydrido, and $X^O$ is hydrido;

$R^2$ is 3-aminophenyl, B is (S)-2-butyl, A is single bond, $Y^O$ is 4-amidinobenzyl, $R^1$ is hydrido, and $X^O$ is hydrido;

$R^2$ is 5-amino-2-fluorophenyl, B is isopropyl, A is single bond, $Y^O$ is 4-amidinobenzyl, $R^1$ is hydrido, and $X^O$ is hydrido;

$R^2$ is 2-methyl-3-aminophenyl, B is isopropyl, A is single bond, $Y^O$ is 4-amidinobenzyl, $R^1$ is hydrido, and $X^O$ is hydrido;

$R^2$ is 3-aminophenyl, B is ethyl, A is single bond, $Y^O$ is 4-amidinobenzyl, $R^1$ is hydrido, and $X^O$ is hydrido;

$R^2$ is 3-aminophenyl, B is ethyl, A is single bond, $Y^O$ is 4-amidino-2-fluorobenzyl, $R^1$ is hydrido, and $X^O$ is hydrido;

$R^2$ is 3-aminophenyl, B is 2-propenyl, A is single bond, $Y^O$ is 4-amidinobenzyl, $R^1$ is hydrido, and $X^O$ is hydrido;

$R^2$ is 3-aminophenyl, B is isopropyl, A is single bond, $Y^O$ is 4-amidino-2-fluorobenzyl, $R^1$ is hydrido, and $X^O$ is hydrido;

$R^2$ is 3-aminophenyl, B is isopropyl, A is single bond, $Y^O$ is 4-amidinobenzyl, $R^1$ is hydrido, and $X^O$ is hydrido;

$R^2$ is 3-aminophenyl, B is 2-butyl, A is single bond, $Y^O$ is 4-amidinobenzyl, $R^1$ is hydrido, and $X^O$ is hydrido;

$R^2$ is 3-aminophenyl, B is (R)-2-butyl, A is single bond, $Y^O$ is 4-amidinobenzyl, $R^1$ is hydrido, and $X^O$ is hydrido;

$R^2$ is 3-aminophenyl, B is 2-propynyl, A is single bond, $Y^O$ is 4-amidinobenzyl, $R^1$ is hydrido, and $X^O$ is hydrido;

$R^2$ is 3-aminophenyl, B is 3-pentyl, A is single bond, $Y^O$ is 4-amidinobenzyl, $R^1$ is hydrido, and $X^O$ is hydrido;

$R^2$ is 3-aminophenyl, B is hydrido, A is $CH_2$, $Y^O$ is 4-amidinobenzyl, $R^1$ is hydrido, and $X^O$ is hydrido;

$R^2$ is 3-aminophenyl, B is ethyl, A is $CH_2$, is 4-amidinobenzyl, $R^1$ is hydrido, and $X^O$ is hydrido;

$R^2$ is 3-aminophenyl, B is 2-methylpropyl, A is single bond, $Y^O$ is 4-amidinobenzyl, $R^1$ is hydrido, and $X^O$ is hydrido;

$R^2$ is 3-aminophenyl, B is 2-propyl, A is $CH_3CH$, $Y^O$ is 4-amidinobenzyl, $R^1$ is hydrido, and $X^O$ is hydrido;

$R^2$ is 3-aminophenyl, B is propyl, A is single bond, $Y^O$ is 4-amidino-2-fluorobenzyl, $R^1$ is hydrido, and $X^O$ is hydrido;

$R^2$ is 3-aminophenyl, B is 6-amidocarbonylhexyl, A is single bond, $Y^O$ is 4-amidinobenzyl, $R^1$ is hydrido, and $X^O$ is hydrido;

$R^2$ is 3-aminophenyl, B is tert-butyl, A is single bond, $Y^O$ is 4-amidinobenzyl, $R^1$ is hydrido, and $X^O$ is hydrido;

$R^2$ is 3-aminophenyl, B is tert-butyl, A is single bond, $Y^O$ is 4-amidinobenzyl, $R^1$ is hydrido, and $X^O$ is hydrido;

$R^2$ is 3-aminophenyl, B is 3-hydroxypropyl, A is single bond, $Y^O$ is 4-amidinobenzyl, $R^1$ is hydrido, and $X^O$ is hydrido;

$R^2$ is 3-aminophenyl, B is 2-methylpropyl, A is single bond, $Y^O$ is 4-amidino-2-fluorobenzyl, $R^1$ is hydrido, and $X^O$ is hydrido;

$R^2$ is 3-aminophenyl, B is butyl, A is single bond, $Y^O$ is 4-amidinobenzyl, $R^1$ is hydrido, and $X^O$ is hydrido;

$R^2$ is 3-aminophenyl, B is 1-methoxy-2-propyl, A is single bond, $Y^O$ is 4-amidinobenzyl, $R^1$ is hydrido, and $X^O$ is hydrido;

$R^2$ is 3-aminophenyl, B is 1-methoxy-2-propyl, A is single bond, $Y^O$ is 4-amidinobenzyl, $R^1$ is hydrido, and $X^O$ is hydrido;

$R^2$ is 3-aminophenyl, B is 2-methoxyethyl, A is single bond, $Y^O$ is 4-amidinobenzyl, $R^1$ is hydrido, and $X^O$ is hydrido;

$R^2$ is 3-aminophenyl, B is 2-propyl, A is single bond, $Y^O$ is 5-amidino-2-thienylmethyl, $R^1$ is hydrido, and $X^O$ is hydrido;

$R^2$ is 3-aminophenyl, B is 2-propyl, A is single bond, $Y^O$ is 4-amidino-3-fluorobenzyl, $R^1$ is hydrido, and $X^O$ is hydrido;

$R^2$ is 3-carboxyphenyl, B is 2-propyl, A is single bond, $Y^O$ is 4-amidinobenzyl, $R^1$ is hydrido, and $X^O$ is hydrido;

$R^2$ is 3-aminophenyl, B is 2-propyl, A is single bond, $Y^O$ is 4-amidino-3-fluorobenzyl, $R^1$ is hydrido, and $X^O$ is hydrido;

$R^2$ is 3-amninophenyl, B is 2,2,2-trifluoroethyl, A is single bond, $Y^O$ is 4-amidinobenzyl, $R^1$ is aminomethyl, and $X^O$ is hydrido;

$R^2$ is 3-aminophenyl, B is (S)-2-butyl, A is single bond, $Y^O$ is 4-amidinobenzyl, $R^1$ is aminomethyl, and $X^O$ is hydrido;

$R^2$ is 5-amino-2-fluorophenyl, B is isopropyl, A is single bond, $Y^O$ is 4-amidinobenzyl, $R^1$ is aminomethyl, and $X^O$ is hydrido;

$R^2$ is 2-methyl-3-aminophenyl, B is isopropyl, A is single bond, $Y^O$ is 4-amidinobenzyl, $R^1$ is aminomethyl, and $X^O$ is hydrido;

$R^2$ is 3-aminophenyl, B is ethyl, A is single bond, $Y^O$ is 4-amidinobenzyl, $R^1$ is aminomethyl, and $X^O$ is hydrido;

$R^2$ is 3-aminophenyl, B is ethyl, A is single bond, $Y^0$ is 4-amidino-2-fluorobenzyl, $R^1$ is aminomethyl, and $X^O$ is hydrido;

$R^2$ is 3-aminophenyl, B is 2-propenyl, A is single bond, $Y^0$ is 4-amidinobenzyl, $R^1$ is aminomethyl, and $X^O$ is hydrido;

$R^2$ is 3-aminophenyl, B is isopropyl, A is single bond, $Y^0$ is 4-amidino-2-fluorobenzyl, $R^1$ is aminomethyl, and $X^O$ is hydrido;

$R^2$ is 3-aminophenyl, B is isopropyl, A is single bond, $Y^0$ is 4-amidinobenzyl, $R^1$ is aminomethyl, and $X^O$ is hydrido;

$R^2$ is 3-aminophenyl, B is 2-butyl, A is single bond, $Y^0$ is 4-amidinobenzyl, $R^1$ is aminomethyl, and $X^O$ is hydrido;

$R^2$ is 3-aminophenyl, B is (R)-2-butyl, A is single bond, $Y^0$ is 4-amidinobenzyl, $R^1$ is aminomethyl, and $X^O$ is hydrido;

$R^2$ is 3-aminophenyl, B is 2-propynyl, A is single bond, $Y^0$ is 4-amidinobenzyl, $R^1$ is aminomethyl, and $X^O$ is hydrido:

$R^2$ is 3-aminophenyl, B is 3-pentyl, A is single bond, $Y^0$ is 4-amidinobenzyl, $R^1$ is aminomethyl, and $X^O$ is hydrido;

$R^2$ is 3-aminophenyl, B is hydrido, A is $CH_2$, $Y^0$ is 4-amidinobenzyl, $R^1$ is aminomethyl, and $X^O$ is hydrido;

$R^2$ is 3-aminophenyl, B is ethyl, A is $CH_2$, $Y^0$ is 4-amidinobenzyl, $R^1$ is aminomethyl, and $X^O$ is hydrido;

$R^2$ is 3-aminophenyl, B is 2-methylpropyl, A is single bond, $Y^0$ is 4-amidinobenzyl, $R^1$ is aminomethyl, and $X^O$ is hydrido;

$R^2$ is 3-aminophenyl, B is 2-propyl, A is $CH_3C$, $Y^0$ is 4-amidinobenzyl, $R^1$ is aminomethyl, and $X^O$ is hydrido;

$R^2$ is 3-aminophenyl, B is propyl, A is single bond, $Y^0$ is 4-amidino-2-fluorobenzyl, $R^1$ is aminomethyl, and $X^O$ is hydrido;

$R^2$ is 3-aminophenyl, B is amidocarbonylhexyl, A is single bond, $Y^0$ is 4-amidinobenzyl, $R^1$ is aminomethyl, and $X^O$ is hydrido;

$R^2$ is 3-aminophenyl, B is tert-butyl, A is single bond, $Y^0$ is 4-amidinobenzyl, $R^1$ is aminomethyl, and $X^O$ is hydrido;

$R^2$ is 3-aminophenyl, B is tert-butyl, A is single bond, $Y^0$ is 4-amidinobenzyl, $R^1$ is aminomethyl, and $X^O$ is hydrido;

$R^2$ is 3-aminophenyl, B is 3-hydroxypropyl, A is single bond, $Y^0$ is 4-amidinobenzyl, $R^1$ is aminomethyl, and $X^O$ is hydrido;

$R^2$ is 3-aminophenyl, B is 2-methylpropyl, A is single bond, $Y^0$ is 4-amidino-2-fluorobenzyl, $R^1$ is aminomethyl, and $X^O$ is hydrido;

$R^2$ is 3-aminophenyl, B is butyl, A is single bond, $Y^0$ is 4-amidinobenzyl, $R^1$ is aminomethyl, and $X^O$ is hydrido;

$R^2$ is 3-aminophenyl, B is 1-methoxy-2-propyl, A is single bond, $Y^0$ is 4-amidinobenzyl, $R^1$ is aminomethyl, and $X^O$ is hydrido;

$R^2$ is 3-aminophenyl, B is 1-methoxy-2-propyl, A is single bond, $Y^0$ is 4amidinobenzyl, $R^1$ is aminomethyl, and $X^O$ is hydrido;

$R^2$ is 3-aminophenyl, B is 2-methoxyethyl, A is single bond, $Y^0$ is 4-amidinobenzyl, $R^1$ is aminomethyl, and $X^O$ is hydrido;

$R^2$ is 3-aminophenyl, B is 2-propyl, A is single bond, $Y^0$ is 5-amidino-2-thienylmethyl, $R^1$ is aminomethyl, and $X^O$ is hydrido;

$R^2$ is 3-aminophenyl, B is 2-propyl, A is single bond, $Y^0$ is 4-amidino-3-fluorobenzyl, $R^1$ is aminomethyl, and $X^O$ is hydrido;

$R^2$ is 3-carboxyphenyl, B is 2-propyl, A is single bond, $Y^0$ is 4-amidinobenzyl, $R^1$ is aminomethyl, and $X^O$ is hydrido;

$R^2$ is 3-aminophenyl, B is 2-propyl, A is single bond, $Y^0$ is 4-amidino-3-fluorobenzyl, $R^1$ is aminomethyl, and $X^O$ is hydrido;

$R^2$ is 3-amidocarbonyl-5-aminophenyl, B is 2-propyl, A is single bond, $Y^0$ is 4-amidinobenzyl, $R^1$ is chloro, and $X^O$ is hydrido;

$R^2$ is 3-amino-5-(N-benzylamidocarbonyl)phenyl, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl)phenyl, B is 2-propyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl)phenyl, B is 2-propyl, A is single bond, $Y^0$ is 4-amidinobenzyl, $R^1$ is chloro, and $X^O$ is hydrido;

$R^2$ is 3-amino-5-(N-(2-trifluoromethylbenzyl)amidocarbonyl)-phenyl, B is 2-propyl, A is single bond, $Y^0$ is 4-amidinobenzyl, $R^1$ is chloro, and $X^O$ is hydrido;

$R^2$ is 3,5-diaminophenyl, B is 2-propyl, A is single bond, $Y^0$ is 4-amidinobenzyl, $R^1$ is chloro, and $X^O$ is hydrido;

$R^2$ is 3-amino-5-carboxyphenyl, B is 2-propyl, A is single bond, $Y^0$ is 4-amidinobenzyl, $R^1$ is chloro, and $X^O$ is hydrido;

$R^2$ is 3-amidocarbonyl-5-aminophenyl, B is 2-propyl, A is single bond, $Y^0$ is 4-amidinobenzyl, $R^1$ is hydrido, and $X^O$ is hydrido;

$R^2$ is 3-amino-5-(N-benzylamidocarbonyl)phenyl, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl)phenyl, B is 2-propyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl)phenyl B is 2-propyl, A is single bond, $Y^0$ is 4-amidinobenzyl $R^1$ is hydrido, and $X^O$ is hydrido;

$R^2$ is 3-amino-5-(N-(2-trifluoromethylbenzyl)amidocarbonyl)-phenyl, B is 2-propyl, A is single bond, $Y^0$ is 4-amidinobenzyl, $R^1$ is hydrido, and $X^O$ is hydrido;

$R^2$ is 3-amino-5-carboxyphenyl, B is 2-propyl, A is single bond, $Y^0$ is 4-amidinobenzyl, $R^1$ is hydrido, and $X^O$ is hydrido;

$R^2$ is 3-aminophenyl, B is cyclopropyl, A is single bond, $Y^0$ is 4-amidinobenzyl, $R^1$ is aminomethyl, and $X^O$ is hydrido;

$R^2$ is 3-aminophenyl, B is cyclobutyl, A is single bond, $Y^0$ is 4-amidino-2-fluorobenzyl, $R^1$ is aminomethyl, and $X^O$ is hydrido;

$R^2$ is 3-aminophenyl, B is cyclobutyl, A is single bond, $Y^0$ is 4-amidinobenzyl, $R^1$ is aminomethyl, and $X^O$ is hydrido;

$R^2$ is 3-aminophenyl, B is cyclopropyl, A is single bond, $Y^0$ is 4-amidino-2-fluorobenzyl, $R^1$ is aminomethyl, and $X^O$ is hydrido;

$R^2$ is 3-aminophenyl, B is cyclobutyl, A is single bond, $Y^0$ is 4-amidinobenzyl, $R^1$ is aminomethyl, and $X^O$ is hydrido;

$R^2$ is 3-aminophenyl, B is cyclobutyl, A is single bond, $Y^0$ is 4-amidino-3-fluorobenzyl, $R^1$ is aminomethyl, and $X^O$ is hydrido;

$R^2$ is 3-aminophenyl, B is cyclopentyl, A is single bond, $Y^0$ is 4-amidinobenzyl, $R^1$ is aminomethyl, and $X^O$ is hydrido;

$R^2$ is 5-amino-2-thienyl, B is cyclobutyl, A is single bond, $Y^0$ is 4-amidinobenzyl, $R^1$ is aminomethyl, and $X^O$ is hydrido;

$R^2$ is 3-aminophenyl, B is cyclopropyl, A is $CH_2$, $Y^0$ is 4-amidinobenzyl, $R^1$ is aminomethyl, and $X^O$ is hydrido;

$R^2$ is 3-aminophenyl, B is 2-(2R)-bicyclo[2.2.1]-heptyl, A is single bond, $Y^0$ is 4-amidinobenzyl, $R^1$ is aminomethyl, and $X^O$ is hydrido;

$R^2$ is 3-aminophenyl, B is cyclopentyl, A is single bond, $Y^0$ is 4-amidino-2-fluorobenzyl, $R^1$ is aminomethyl, and $X^O$ is hydrido;

$R^2$ is 3-aminophenyl, B is cyclohexyl, A is $CH_2CH_2$, $Y^0$ is 4-amidinobenzyl, $R^1$ is aminomethyl, and $X^O$ is hydrido;

$R^2$ is 2-hydroxyphenyl, B is cyclobutyl, A is single bond, $Y^0$ is 4-amidinobenzyl, $R^1$ is aminomethyl, and $X^O$ is hydrido;

$R^2$ is phenyl, B is cyclobutyl, A is single bond, $Y^0$ is 4-amidinobenzyl, $R^1$ is aminomethyl, and $X^O$ is hydrido;

$R^2$ is 3-thienyl, B is cyclobutyl, A is single bond, $Y^0$ is 4-amidinobenzyl, $R^1$ is aminomethyl, and $X^O$ is hydrido;

$R^2$ is 2,6-dichlorophenyl, B is cyclobutyl, A is single bond, $Y^0$ is 4-amidinobenzyl, $R^1$ is aminomethyl, and $X^O$ is hydrido;

$R^2$ is 3-aminophenyl, B is cyclopropyl, A is single bond, $Y^0$ is 4-amidinobenzyl, $R^1$ is hydroxymethyl, and $X^O$ is hydrido;

$R^2$ is 3-aminophenyl, B is cyclobutyl, A is single bond, $Y^0$ is 4-amidino-2-fluorobenzyl, $R^1$ is hydroxymethyl, and $X^O$ is hydrido;

$R^2$ is 3-aminophenyl, B is cyclobutyl, A is single bond, $Y^0$ is 4-amidinobenzyl, $R^1$ is hydroxymethyl, and $X^O$ is hydrido;

$R^2$ is 3-aminophenyl, B is cyclopropyl, A is single bond, $Y^0$ is 4-amidino-2-fluorobenzyl, $R^1$ is hydroxymethyl, and $X^O$ is hydrido;

$R^2$ is 3-aminophenyl, B is cyclobutyl, A is single bond, $Y^0$ is 4-amidinobenzyl, $R^1$ is hydroxymethyl, and $X^O$ is hydrido;

$R^2$ is 3-aminophenyl, B is cyclobutyl, A is single bond, $Y^0$ is 4-amidino-3-fluorobenzyl, $R^1$ is hydroxymethyl, and $X^O$ is hydrido;

$R^2$ is 3-aminophenyl, B is cyclopentyl, A is single bond, $Y^0$ is 4-amidinobenzyl, $R^1$ is hydroxymethyl, and $X^O$ is hydrido;

$R^2$ is 5-amino-2-thienyl, B is cyclobutyl, A is single bond, $Y^0$ is 4-amidinobenzyl, $R^1$ is hydroxymethyl, and $X^O$ is hydrido;

$R^2$ is 3-aminophenyl, B is cyclopropyl, A is $CH_2$, $Y^0$ is 4-amidinobenzyl, $R^1$ is hydroxymethyl, and $X^O$ is hydrido;

$R^2$ is 3-aminophenyl, B is 2-(2R)-bicyclo[2.2.1]-heptyl, A is single bond, $Y^0$ is 4-amidinobenzyl, $R^1$ is hydroxymethyl, and $X^O$ is hydrido;

$R^2$ is 3-aminophenyl, B is cyclopentyl, A is single bond, $Y^0$ is 4-amidino-2-fluorobenzyl, $R^1$ is hydroxymethyl, and $X^O$ is hydrido;

$R^2$ is 3-aminophenyl, B is cyclohexyl, A is $CH_2CH_2$, $Y^0$ is 4-amidinobenzyl, $R^1$ is hydroxymethyl, and $X^O$ is hydrido;

$R^2$ is 2-hydroxyphenyl, B is cyclobutyl, A is single bond, $Y^0$ is 4-amidinobenzyl, $R^1$ is hydroxymethyl, and $X^O$ is hydrido;

$R^2$ is phenyl, B is cyclobutyl, A is single bond, $Y^0$ is 4-amidinobenzyl, $R^1$ is hydroxymethyl, and $X^O$ is hydrido;

$R^2$ is 3-thienyl, B is cyclobutyl, A is single bond, $Y^0$ is 4-amidinobenzyl, $R^1$ is hydroxymethyl, and $X^O$ is hydrido;

$R^2$ is 2,6-dichlorophenyl, B is cyclobutyl, A is single bond, $Y^0$ is 4-amidinobenzyl, $R^1$ is hydroxymethyl, and $X^O$ is hydrido;

$R^2$ is 3-amidocarbonyl-5-aminophenyl, B is cyclobutyl, A is single bond, $Y^0$ is 4-amidinobenzyl, $R^1$ is chloro, and $X^O$ is hydrido;

$R^2$ is 3-amino-5-(N-benzylamidocarbonyl)phenyl, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidocarbonyl) phenyl, B is cyclobutyl, A is single bond, $Y^0$ is 4-amidinobenzyl, $R^1$ is chloro, and $X^O$ is hydrido;

$R^2$ is 3-amino-5-(N-(2-chlorobenzyl)amidosulfonyl) phenyl, B is cyclobutyl, A is single bond, $Y^0$ is 4-amidinobenzyl, $R^1$ is chloro, and $X^O$ is hydrido;

$R^2$ is 3-amino-5-(-N-(2-trifluoromethylbenzyl) amidocarbonyl)-phenyl, B is cyclobutyl, A is single bond, $Y^0$ is 4-amidinobenzyl, $R^1$ is chloro, and $X^O$ is hydrido;

$R^2$ is 3,5-diaminophenyl, B is cyclobutyl, A is single bond, $Y^0$ is 4-amidinobenzyl, $R^1$ is chloro, and $X^O$ is hydrido;

$R^2$ is 3-amino-5-carboxyphenyl, B is cyclobutyl, A is single bond, $Y^0$ is 4-amidinobenzyl, $R^1$ is chloro, and $X^O$ is hydrido;

$R^2$ is 3-amidocarbonyl-5-aminophenyl, B is cyclobutyl, A is single bond, $Y^0$ is 4-amidinobenzyl, $R^1$ is hydrido, and $X^O$ is hydrido;

$R^2$ is 3-amino-5-(N-benzylamidocarbonyl)phenyl, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidocarbonyl) phenyl, B is cyclobutyl, A is single bond, $Y^0$ is 4-amidinobenzyl, $R^1$ is hydrido, and $X^O$ is hydrido;

$R^2$ is 3-amino-5-(N-(2-chlorobenzyl)amidosulfonyl) phenyl, B is cyclobutyl, A is single bond, $Y^0$ is 4-amidinobenzyl $R^1$ is hydrido, and $X^O$ is hydrido;

$R^2$ is 3-amino-5-(N-(2-trifluoromethylbenzyl) amidocarbonyl)phenyl, B is cyclobutyl, A is single bond, $Y^0$ is 4-amidinobenzyl, $R^1$ is hydrido, and $X^O$ is hydrido;

$R^2$ is 3,5-diaminophenyl, B is cyclobutyl, A is single bond, $Y^0$ is 4-amidinobenzyl, $R^1$ is hydrido, and $X^O$ is hydrido;

$R^2$ is 3-amino-5-carboxyphenyl, B is cyclobutyl, A is single bond, is 4-amidinobenzyl, $R^1$ is hydrido, and $X^O$ is hydrido.

Using the examples and methods described herein previously, the following further examples having $R^1$ and $R^2$ bonded together to form —W=X—Y=Z— and an amidinoaralkyl or amidinoheteroaralkyl type $Y^0$ group could be prepared of the formula:

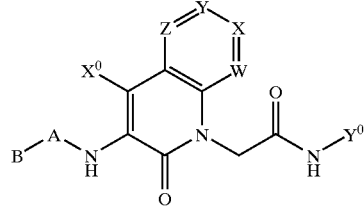

wherein;

B is 3-chlorophenyl, A is $CH_2CH_2$, $Y^0$ is amidinobenzyl, W is CH, X is C—$NH_2$, $Y^0$ is C—$CH_2CO_2H$, Z is CH, and $X^O$ is hydrido;

B is phenyl, A is $CH_2$, $Y^0$ is 4-amidinobenzyl, W is N, X is C—$CH_2NH_2$, Y is C—$CO_2H$, Z is CH, and $X^O$ is hydrido;

B is 3-chlorophenyl, A is $CH_2CH_2$, $Y^0$ is 4-amidinobenzyl, W is C—OH, X is C—$CH_2CH_2NH_2$, Y is C—OH, Z is CH, and $X^O$ is hydrido;

B is 2-imidazolyl, A is $CH_2CH_2CH_2$, $Y^0$ is 4-amidinobenzyl, W is C—$NH_2$, X is C—$CH_2OH$, Y is C—$NH_2$, Z is CH, and $X^O$ is hydrido;

B is 2,2,2-trifluoroethyl, A is single bond, $Y^0$ is 4-amidinobenzyl, W is CH, X is C—$NH_2$, Y is C—$CH_2CO_2H$, Z is CH, and $X^O$ is hydrido;

B is (S)-2-butyl, A is single bond, $Y^0$ is 4-amidinobenzyl, W is N, X is C—$CH_2NH_2$, Y is C—$CO_2H$, Z is CH, and $X^O$ is hydrido;

B is isopropyl, A is single bond, $Y^0$ is 4-amidinobenzyl, W is C—OH, X is C—$CH_2CH_2NH_2$, Y is C—OH, Z is CH, and $X^O$ is hydrido;

B is isopropyl, A is single bond, $Y^0$ is 4-amidinobenzyl, W is C—$NH_2$, X is C—$CH_2OH$, Y is C—$NH_2$, Z is CH, and $X^O$ is hydrido;

B is hydrido, A is $CH_2(CR_3)N$, $Y^0$ is 4-amidinobenzyl, W is CH, X is C—$NH_2$, Y is C—$CH_2CO_2H$, Z is CH, and $X^O$ is hydrido;

B is ethyl, A is single bond, $Y^0$ is 4-amidinobenzyl, W is N, X is C—$CH_2NH_2$, Y is C—$CO_2H$, Z is CH, and $X^O$ is hydrido;

B is ethyl, A is single bond, $Y^0$ is 4-amidino-2-fluorobenzyl, W is C—OH, X is C—$CH_2CH_2NH_2$, Y is C—OH, Z is CH, and $X^O$ is hydrido;

B is 2-propenyl, A is single bond, $Y^0$ is 4-amidinobenzyl, W is C—$NH_2$, X is C—$CH_2OH$, Y is C—$NH_2$, Z is CH, and $X^O$ is hydrido;

B is isopropyl, A is single bond, $Y^0$ is 4-amidino-2-fluorobenzyl, W is CH, X is C—$NH_2$, Y is C—$CH_2CO_2H$, Z is CH, and $X^O$ is hydrido;

B is isopropyl, A is single bond, $Y^0$ is 4-amidinobenzyl, W is N, X is C—$CH_2NH_2$, Y is C—$CO_2H$, Z is CH, and $X^O$ is hydrido;

B is 2-butyl, A is single bond, $Y^0$ is 4-amidinobenzyl, W is C—OH, X is C—$CH_2CH_2NH_2$, Y is C—OH, Z is CH, and $X^O$ is hydrido;

B is (R)-2-butyl, A is single bond, $Y^0$ is 4-amidinobenzyl, W is C—$NH_2$, X is C—$CH_2OH$, Y is C—$NH_2$, Z is CH, and $X^O$ is hydrido;

B is 2-propynyl, A is single bond, $Y^0$ is 4-amidinobenzyl, W is CH, X is C—$NH_2$, Y is C—$CH_2CO_2H$, Z is CH, and $X^O$ is hydrido;

B is hydrido, A is $CH_2$, $Y^0$ is 4-amidinobenzyl, W is N, X is C—$CH_2NH_2$, Y is C—$CO_2H$, Z is CH, and $X^O$ is hydrido;

B is cyclopropyl, A is single bond, $Y^0$ is 4-amidinobenzyl, W is C—OH, X is C—$CH_2CH_2NH_2$, Y is C—OH, Z is CH, and $X^O$ is hydrido;

B is cyclobutyl, A is single bond, $Y^0$ is 4-amidino-2-fluorobenzyl, W is C—$NH_2$, X is C—$CH_2OH$, Y is C—$NH_2$, Z is CH, and $X^O$ is hydrido;

B is cyclobutyl, A is single bond, $Y^0$ is 4-amidinobenzyl, W is CH, X is C—$NH_2$, Y is C—$CH_2CO_2H$, Z is CH, and $X^O$ is hydrido;

B is cyclopropyl, A is single bond, $Y^0$ is 4-amidino-2-fluorobenzyl, W is N, X is C—$CH_2NH_2$, Y is C—$CO_2H$, Z is CH, and $X^O$ is hydrido;

B is cyclobutyl, A is single bond, $Y^0$ is 4-amidinobenzyl, W is C—OH, X is C—$CH_2CH_2NH_2$, Y is C—OH, Z is CH, and $X^O$ is hydrido;

B is cyclobutyl, A is single bond, $Y^0$ is 4-amidino-3-fluorobenzyl, W is C—$NH_2$, X is C—$CH_2OH$, Y is C—$NH_2$, Z is CH, and $X^O$ is hydrido;

B is cyclopentyl, A is single bond, $Y^0$ is 4-amidinobenzyl, W is CH, X is C—$NH_2$, Y is C—$CH_2CO_2H$, Z is CH, and $X^O$ is hydrido;

B is cyclobutyl, A is single bond, $Y^0$ is 4-amidinobenzyl, W is N, X is C—$CH_2NH_2$, Y is C—$CO_2H$, Z is CH, and $X^O$ is hydrido;

B is cyclopropyl, A is $CH_2$, $Y^0$ is 4-amidinobenzyl, W is C—OH, X is C—$CH_2CH_2NH_2$, Y is C—OH, Z is CH, and $X^O$ is hydrido;

B is 2-(2R)-bicyclo[2.2.1]-heptyl, A is single bond, $Y^0$ is 4-amidinobenzyl, W is C—$NH_2$, X is C—$CH_2OH$, Y is C—$NH_2$, Z is CH, and $X^O$ is hydrido;

B is cyclopentyl, A is single bond, $Y^0$ is 4-amidino-2-fluorobenzyl, W is CH, X is C—$NH_2$, Y is C—$CH_2CO_2H$, Z is CH, and $X^O$ is hydrido;

B is cyclohexyl, A is $CH_2CH_2$, $Y^0$ is 4-amidinobenzyl, W is N, X is C—$CH_2NH_2$, Y is C—$CO_2H$, Z is CH, and $X^O$ is hydrido;

B is 3-chlorophenyl, A is $CH_2CH_2$, $Y^0$ is 4amidinobenzyl, W is C—OH, X is C—$CH_2CH_2NH_2$, Y is C—OH, Z is CH, and $X^O$ is hydrido;

B is phenyl, A is $CH_2$, $Y^0$ is 4-amidinobenzyl, W is C—$NH_2$, X is C—$CH_2OH$, Y is C—$NH_2$, Z is CH, and $X^O$ is hydrido;

B is 3-chlorophenyl, A is $CH_2CH_2$, $Y^0$ is 4-amidinobenzyl, W is CH, X is C—$NH_2$, Y is C—$CH_2CO_2H$, Z is CH, and $X^O$ is hydrido;

B is 2-imidazolyl, A is $CH_2CH_2CH_2$, $Y^0$ is 4-amidinobenzyl, W is N, X is C—$CH_2NH_2$, Y is C—$CO_2H$, Z is CH, and $X^O$ is hydrido;

B is 2,2,2-trifluoroethyl, A is single bond, $Y^0$ is 4-amidinobenzyl, W is C—OH, X is C—$CH_2CH_2NH_2$, Y is C—OH, Z is CH, and $X^O$ is hydrido;

B is (S)-2-butyl, A is single bond, $Y^0$ is 4-amidinobenzyl, W is C—$NH_2$, X is C—$CH_2OH$, Y is C—$NH_2$, Z is CH, and $X^O$ is hydrido;

B is isopropyl, A is single bond, $Y^0$ is 4-amidinobenzyl, W is CH, X is C—$NH_2$, Y is C—$CH_2CO_2H$, Z is CH, and $X^O$ is hydrido;

B is isopropyl, A is single bond, $Y^0$ is 4-amidinobenzyl, W is N, X is C—$CH_2NH_2$, Y is C—$CO_2H$, Z is CH, and $X^O$ is hydrido;

B is hydrido, A is $CH_2(CH_3)N$, $Y^0$ is 4-amidinobenzyl, W is C—OH, X is C—$CH_2CH_2NH_2$, Y is C—OH, Z is CH, and $X^O$ is hydrido;

B is ethyl, A is single bond, $Y^0$ is 4-amidinobenzyl, W is C—$NH_2$, X is C—$CH_2OH$, Y is C—$NH_2$, Z is CH, and $X^O$ is hydrido;

B is ethyl, A is single bond, $Y^0$ is 4-amidino-2-fluorobenzyl, W is CH, X is C—$NH_2$, Y is C—$CH_2CO_2H$, Z is CH, and $X^O$ is hydrido;

B is 2-propenyl, A is single bond, $Y^0$ is 4-amidinobenzyl, W is N, X is C—$CH_2NH_2$, Y is C—$CO_2H$, Z is CH, and $X^O$ is hydrido;

B is isopropyl, A is single bond, $Y^0$ is 4-amidino-2-fluorobenzyl, W is C—OH, X is C—$CH_2CH_2NH_2$, Y is C—OH, Z is CH, and $X^O$ is hydrido;

B is isopropyl, A is single bond, $Y^0$ is 4-amidinobenzyl, W is C—$NH_2$, X is C—$CH_2OH$, Y is C—$NH_2$, Z is CH, and $X^O$ is hydrido;

B is 2-butyl, A is single bond, $Y^0$ is 4-amidinobenzyl, W is CH, X is C—$NH_2$, Y is C—$CH_2CO_2H$, Z is CH, and $X^O$ is hydrido;

B is (R)-2-butyl, A is single bond, $Y^0$ is 4-amidinobenzyl, W is N, X is C—$CH_2NH_2$, Y is C—$CO_2H$, Z is CH, and $X^O$ is hydrido;

B is 2-propynyl, A is single bond, $Y^0$ is 4-amidinobenzyl, W is C—OH, X is C—$CH_2CH_2NH_2$, Y is C—OH, Z is CH, and $X^O$ is hydrido;

B is hydrido, A is $CH_2$, $Y^0$ is 4-amidinobenzyl, W is C—$NH_2$, X is C—$CH_2OH$, Y is C—$NH_2$, Z is CH, and $X^O$ is hydrido;

B is cyclopropyl, A is single bond, $Y^0$ is 4-amidinobenzyl, W is CH, X is C—$NH_2$, Y is C—$CH_2CO_2H$, Z is CH, and $X^O$ is hydrido;

B is cyclobutyl, A is single bond, $Y^0$ is 4-amidino-2-fluorobenzyl, W is N, X is C—$CH_2NH_2$, Y is C—$CO_2H$, Z is CH, and $X^O$ is hydrido;

B is cyclobutyl, A is single bond, $Y^0$ is 4-amidinobenzyl, W is C—OH, X is C—$CH_2CH_2NH_2$, Y is C—OH, Z is CH, and $X^O$ is hydrido;

B is cyclopropyl, A is single bond, $Y^0$ is 4-amidino-2-fluorobenzyl, W is C—$NH_2$, X is C—$CH_2OH$, Y is C—$NH_2$, Z is CH, and $X^O$ is hydrido;

B is cyclobutyl, A is single bond, $Y^0$ is 4-amidinobenzyl, W is CH, X is C—$NH_2$, Y is C—$CH_2CO_2H$, Z is CH, and $X^O$ is hydrido;

B is cyclobutyl, A is single bond, $Y^0$ is 4-amidino-3-fluorobenzyl, W is N, X is C—$CH_2NH_2$, Y is C—$CO_2H$, Z is CH, and $X^O$ is hydrido;

B is cyclopentyl, A is single bond, $Y^0$ is 4-amidinobenzyl, W is C—OH, X is C—CH$_2$CH$_2$NH$_2$, Y is C—OH, Z is CH, and $X^O$ is hydrido;

B is cyclobutyl, A is single bond, $Y^0$ is 4-amidinobenzyl, W is C—NH$_2$, X is C—CH$_2$OH, Y is C—NH$_2$, Z is CH, and $X^O$ is hydrido;

B is cyclopropyl, A is CH$_2$, $Y^0$ is 4-amidinobenzyl, W is CH, X is C—NH$_2$, Y is C—CH$_2$CO$_2$H, Z is CH, and $X^O$ is hydrido;

B is (2R)-bicyclo[2.2.1]-heptyl, A is single bond, $Y^0$ is 4-amidinobenzyl, W is N, X is C—CH$_2$NH$_2$, Y is C—CO$_2$H, Z is CH, and $X^O$ is hydrido;

B is cyclopentyl, A is single bond, $Y^0$ is 4-amidino-2-fluorobenzyl, W is C—OH, X is C—CH$_2$CH$_2$NH$_2$, Y is C—OH, Z is CH, and $X^O$ is hydrido;

B is cyclohexyl, A is CH$_2$CH$_2$, $Y^0$ is 4-amidinobenzyl, W is C—NH$_2$, X is C—CH$_2$OH, Y is C—NH$_2$, Z is CH, and $X^O$ is hydrido;

B is cyclobutyl, A is single bond, $Y^0$ is 4-amidino-2-fluorobenzyl, W is C—H, X is C—NH$_2$, Y is C—NH$_2$, Z is CH, and $X^O$ is hydrido;

B is cyclobutyl, A is single bond, $Y^0$ is 4-amidino-2-fluorobenzyl, W is C—H, X is C—NH$_2$, Y is C—CH$_2$NH$_2$, Z is CH, and $X^O$ is hydrido;

B is cyclobutyl, A is single bond, $Y^0$ is 4-amidino-2-fluorobenzyl, W is C—H, X is C—CO$_2$H, Y is C—CH$_2$NH$_2$, Z is CH, and $X^O$ is hydrido;

B is cyclobutyl, A is single bond, $Y^0$ is 4-amidinobenzyl, W is CH, X is C—CH$_2$CO$_2$H, Y is C—CH$_2$NH$_2$, Z is CH, and $X^O$ is hydrido;

B is cyclobutyl, A is single bond, $Y^0$ is 4-amidinobenzyl, W is CH, X is C—CH$_2$CO$_2$H, X is C—NH$_2$, Z is CH, and $X^O$ is hydrido;

B is isopropyl, A is single bond, $Y^0$ is 4-amidino-2-fluorobenzyl, W is C—H, X is C—NH$_2$, Y is C—NH$_2$, Z is CH, and $X^O$ is hydrido;

B is isopropyl, A is single bond, $Y^0$ is 4-amidino-2-fluorobenzyl, W is C—H, X is C—NH$_2$, Y is C—CH$_2$NH$_2$, Z is CH, and $X^O$ is hydrido;

B is isopropyl, A is single bond, $Y^0$ is 4-amidino-2-fluorobenzyl, W is C—H, X is C—CO$_2$H, Y is C—CH$_2$NH$_2$, Z is CH, and $X^O$ is hydrido;

B is isopropyl, A is single bond, $Y^0$ is 4-amidinobenzyl, W is CH, X is C—CH$_2$CO$_2$H, Y is C—CH$_2$NH$_2$, Z is CH, and $X^O$ is hydrido;

B is isopropyl, A is single bond, $Y^0$ is 4-amidinobenzyl, W is CH, X is C—CH$_2$CO$_2$H, X is C—NH$_2$, Z is CH, and $X^O$ is hydrido.

Using the examples and methods described herein previously, the following additional examples having a guanidinoalkyl type $Y^{AT}$ group could be prepared of the formula:

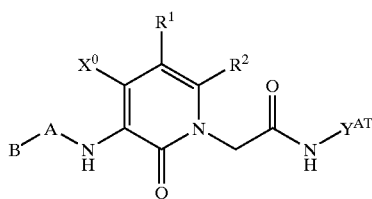

wherein;

$R^2$ is 3-aminophenoxy, B is phenyl, A is CH$_2$, $Y^{AT}$ is 5-guanidino-1-oxo-1-(2-thiazolyl)-2-pentyl, $R^1$ is hydroxymethyl, and $X^O$ is hydrido;

$R^2$ is phenoxy, B is phenyl, A is CH$_2$CH$_2$, $Y^{AT}$ is 5-guanidino-1-oxo-1-(2-thiazolyl)-2-pentyl, $R^1$ is hydroxymethyl, and $X^O$ is hydrido;

$R^2$ is benzyloxy, B is phenyl, A is CH$_2$CH$_2$, $Y^{AT}$ is 5-guanidino-1-oxo-1-(2-thiazolyl)-2-pentyl, $R^1$ is hydroxymethyl, and $X^O$ is hydrido;

$R^2$ is phenoxy, B is phenyl, A is CH$_2$CH$_2$, $Y^{AT}$ is 5-guanidino-1-oxo-1-(2-thiazolyl)-2-pentyl, $R^1$ is hydroxymethyl, and $X^O$ is hydrido;

$R^2$ is benzylamino, B is phenyl, A is CH$_2$CH$_2$, $Y^{AT}$ is 5-guanidino-1-oxo-1-(2-thiazolyl)-2-pentyl, $R^1$ is hydroxymethyl, and $X^O$ is hydrido;

$R^2$ is phenoxy, B is phenyl, A is CH$_2$CH$_2$, $Y^{AT}$ is 5-guanidino-1-oxo-1-(2-thiazolyl)-2-pentyl, $R^1$ is hydroxymethyl, and $X^O$ is hydrido;

$R^2$ is 3-aminophenoxy, B is phenyl, A is CH$_2$, $Y^{AT}$ is 5-guanidino-1-oxo-1-(2-thiazolyl)-2-pentyl, $R^1$ is aminomethyl, and $X^O$ is fluoro;

$R^2$ is phenoxy, B is phenyl, A is CH$_2$CH$_2$, $Y^{AT}$ is 5-guanidino-1-oxo-1-(2-thiazolyl)-2-pentyl, $R^1$ is aminomethyl, and $X^O$ is fluoro;

$R^2$ is benzylthio, B is phenyl, A is CH$_2$CH$_2$, $Y^{AT}$ is 5-guanidino-1-oxo-1-(2-thiazolyl)-2-pentyl, $R^1$ is aminomethyl, and $X^O$ is fluoro;

$R^2$ is phenoxy, B is phenyl, A is CH$_2$CH$_2$, $Y^{AT}$ is 5-guanidino-1-oxo-1-(2-thiazolyl)-2-pentyl, $R^1$ is aminomethyl, and $X^O$ is fluoro;

$R^2$ is benzyloxy, B is phenyl, A is CH$_2$CH$_2$, $Y^{AT}$ is 5-guanidino-1-oxo-1-(2-thiazolyl)-2-pentyl, $R^1$ is aminomethyl, and $X^O$ is fluoro;

$R^2$ is phenoxy, B is phenyl, A is CH$_2$CH$_2$, $Y^{AT}$ is 5-guanidino-1-oxo-1-(2-thiazolyl)-2-pentyl, $R^1$ is aminomethyl, and $X^O$ is fluoro;

$R^2$ is 3-aminophenoxy, B is phenyl, A is CH$_2$, $Y^{AT}$ is 5-guanidino-1-oxo-1-(2-thiazolyl)-2-pentyl, $R^1$ is fluoro, and $X^O$ is hydroxymethyl;

$R^2$ is phenoxy, B is phenyl, A is CH$_2$CH$_2$, $Y^{AT}$ is 5-guanidino-1-oxo-1-(2-thiazolyl)-2-pentyl, $R^1$ is fluoro, and $X^O$ is hydroxymethyl;

$R^2$ is benzylamino, B is phenyl, A is CH$_2$CH$_2$, $Y^{AT}$ is 5-guanidino-1-oxo-1-(2-thiazolyl)-2-pentyl, $R^1$ is fluoro, and $X^O$ is hydroxymethyl;

$R^2$ is phenoxy, B is phenyl, A is CH$_2$CH$_2$, $Y^{AT}$ is 5-guanidino-1-oxo-1-(2-thiazolyl)-2-pentyl, $R^1$ is fluoro, and $X^O$ is hydroxymethyl;

$R^2$ is phenylthio, B is phenyl, A is CH$_2$CH$_2$, $Y^{AT}$ is 5-guanidino-1-oxo-1-(2-thiazolyl)-2-pentyl, $R^1$ is fluoro, and $X^O$ is hydroxymethyl;

$R^2$ is phenoxy, B is phenyl, A is CH$_2$CH$_2$, $Y^{AT}$ is 5-guanidino-1-oxo-1-(2-thiazolyl)-2-pentyl, $R^1$ is fluoro, and $X^O$ is hydroxymethyl;

$R^2$ is 3-aminophenoxy, B is phenyl, A is CH$_2$, $Y^{AT}$ is 5-guanidino-1-oxo-1-(2-thiazolyl)-2-pentyl, $R^1$ is methoxy, and $X^O$ is aminomethyl;

$R^2$ is phenoxy, B is phenyl, A is CH$_2$CH$_2$, $Y^{AT}$ is 5-guanidino-1-oxo-1-(2-thiazolyl)-2-pentyl, $R^1$ is methoxy, and $X^O$ is aminomethyl;

$R^2$ is benzyloxy, B is phenyl, A is CH$_2$CH$_2$, $Y^{AT}$ is 5-guanidino-1-oxo-1-(2-thiazolyl)-2-pentyl, $R^1$ is methoxy, and $X^O$ is aminomethyl;

$R^2$ is phenoxy, B is phenyl, A is CH$_2$CH$_2$, $Y^{AT}$ is 5-guanidino-1-oxo-1-(2-thiazolyl)-2-pentyl, $R^1$ is methoxy, and $X^O$ is aminomethyl;

$R^2$ is benzylthio, B is phenyl, A is CH$_2$CH$_2$, $Y^{AT}$ is 5-guanidino-1-oxo-1-(2-thiazolyl)-2-pentyl, $R^1$ is methoxy, and $X^O$ is aminomethyl;

$R^2$ is phenoxy, B is phenyl, A is CH$_2$CH$_2$, $Y^{AT}$ is 5-guanidino-1-oxo-1(2-thiazolyl)-2-pentyl, $R^1$ is methoxy, and $X^O$ is aminomethyl;

$R^2$ is 3-aminophenoxy, B is phenyl, A is CH$_2$CH$_2$, $Y^{AT}$ is 5-guanidino-1-oxo-1-(2-thiazolyl)-2-pentyl, $R^1$ is aminomethyl, and $X^O$ is chloro;

$R^2$ is 3-aminophenoxy, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-aminophenoxy, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3,5-diaminophenoxy, B is phenyl, A is $CH_2CH_2$, $Y^{AT}$ is 5-guanidino-1-thiazolyl)-2-pentyl, $R^1$ is chloro, and $X^O$ is hydrido;

$R^2$ is 3-carboxy-5-aminophenoxy, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenoxy, B is phenyl, A is $CH_2CH_2$, $Y^{AT}$ is 5-guanidino-1-oxo-1-thiazolyl)-2-pentyl, chloro, and $X^O$ is hydrido;

$R^{is}$ 3,5-diaminophenoxy, B is isopropyl, A is single bond, $Y^{AT}$ is 5-guanidino-1-oxo-1-thiazolyl)-2-pentyl, $R^1$ is chloro, and $X^O$ is hydrido;

$R^2$ is 3-carboxy-5-aminophenoxy, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenoxy, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3,5-diaminophenoxy, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-carboxy-5-aminophenoxy, B is cyclobutyl, A is single bond, $Y^{AT}$ is 5-guanidino-1-oxo-1-thiazolyl)-2-pentyl, $R^1$ is chloro, and $X^O$ is hydrido;

$R^2$ is 3-amino-5-(N-benzylamidocarbonyl)phenoxy, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-aminophenylthio, B is phenyl, A is $CH_2CH_2$, $Y^{AT}$ is 5guanidino-1-oxo-1-(2-thiazolyl)-2-pentyl, $R^1$ is chloro, and $X^O$ is hydrido;

$R^2$ is 3,5-diaminophenylthio, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-carboxy-5-aminophenylthio, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenylthio, B is phenyl, A is $CH_2CH_2$, $Y^{AT}$ is 5-guanidino-1-oxo-1-thiazolyl)-2-pentyl, chloro, and $X^O$ is hydrido;

$R^2$ is 3,5-diaminophenylthio, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-carboxy-5-aminophenylthio, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenylthio, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3,5-aminophenylthio, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^{is}$ 3-carboxy-5-aminophenylthio, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenylthio, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-2-thienyl, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3,5-amino-2-thienyl, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-carboxy-5-amino-2-thienyl, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)-2-thienyl, B is phenyl, A is $CH_2CH_2$, $Y^{AT}$ is 5-guanidino-1-oxo-1-(2-thiazolyl)-2-pentyl, chloro, and $X^O$ is hydrido;

$R^2$ is 3,5-diamino-2-thienyl, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-carboxy-5-amino-2-thienyl, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)-2-thienyl, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3,5-diamino-2-thienyl, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-carboxy-5-amino-2-thienyl, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)-2-thienyl, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-aminophenyl, B is phenyl, A is $CH_2CH_2$, $Y^{AT}$ is 5guanidino-1-oxo-1-(2-thiazolyl)-2-pentyl, $R^1$ is aminomethyl, and $X^O$ is chloro;

$R^2$ is 3,5-diaminophenyl, B is phenyl, A is $CH_2CH_2$ $Y^{AT}$ is 5-guanidino-1oxo-1-(2-thiazolyl)-2-pentyl, $R^1$ is aminomethyl, and $X^O$ is chloro;

$R^2$ is 3-carboxy-5aminophenyl, B is phenyl, A is $CH_2CH_2$, $Y^{AT}$ is 5-guanidino-1-oxo-1-(2-thiazolyl)-2-pentyl, $R^1$ is aminomethyl, and $X^O$ is chloro;

$R^2$ is 3-amino-5-(N-benzylamidocarbonyl)phenyl, B is phenyl, A is $CH_2CH_2$, $Y^{AT}$ is 5-guanidino-1-oxo-1-(2-thiazolyl)-2-pentyl, $R^1$ is aminomethyl, and $X^O$ is chloro;

$R^2$ is 3,5-diaminophenyl, B is isopropyl, A is single bond, $Y^{AT}$ is 5-guanidino-1-oxo-1-(2-thiazolyl)-2-pentyl, $R^1$ is aminomethyl, and $X^O$ is chloro;

$R^2$ is 3-carboxy-5-aminophenyl, B is isopropyl, A is single bond, $Y^{AT}$ is 5-guanidino-1-oxo-1-(2-thiazolyl)-2-pentyl, $R^1$ is aminomethyl, and $X^O$ is chloro;

$R^2$ is 3-amino-5-(N-benzylamidocarbonyl)phenyl, B is isopropyl, A is single bond, $Y^{AT}$ is 5-guanidino-1-oxo-1-(2-thiazolyl)-2-pentyl, $R^1$ is aminomethyl, and $X^O$ is chloro;

$R^2$ is 3,5-diaminophenyl, B is cyclobutyl, A is single bond, $Y^{AT}$ is 5-guanidino-1-oxo-1-(2-thiazolyl)-2-pentyl, $R^1$ is aminomethyl, and $X^O$ is chloro;

$R^2$ is 3-carboxy-5-aminophenyl, B is cyclobutyl, A is single bond, $Y^{AT}$ is 5-guanidino-1-oxo-1-(2-thiazolyl)-2-pentyl, $R^1$ is aminomethyl, and $X^O$ is chloro;

$R^2$ is 3-amino-5-(N-benzylamidocarbonyl)phenyl, B is cyclobutyl, A is single bond, $Y^{AT}$ is 5-guanidino-1-oxo-1-(2-thiazolyl)-2-pentyl, $R^1$ is aminomethyl, and $X^O$ is chloro;

$R^2$ is 3-aminophenyl, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3,5-diaminophenyl, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-carboxy-5-aminophenyl, B is phenyl, A is $CH_2CH_2$, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenyl, B is phenyl, A is $CH_2CH_2$, $Y^{AT}$ is 5-guanidino-1-oxo-1-(2-thiazolyl)-2-pentyl, chloro, and $X^O$ is hydrido;

$R^2$ is 3,5-diaminophenyl, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-carboxy-5-aminophenyl, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenyl, B is isopropyl, A is single bond, $Y^{AT}$ is 5-guanidino-1-oxo-1-(2-thiazolyl)-2-pentyl, $R^1$ is chloro, and $X^O$ is hydrido;

$R^2$ is 3,5-diaminophenyl, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-carboxy-5-aminophenyl, B is cyclobutyl, A is single bond, $Y^{AT}$ is 5-guanidino-1-oxo-1-(2-thiazolyl)-2-pentyl, $R^1$ is chloro, and $X^O$ is hydrido;

$R^2$ is 3-amino-5-(N-benzylamidocarbonyl)phenyl, B is cyclobutyl, A is single bond, $Y^{AT}$ is 5-guanidino-1-oxo-1-(2-thiazolyl)-2-pentyl, $R^1$ is chloro, and $X^O$ is hydrido.

Formula (I) compounds of this invention possessing hydroxyl, thiol, and amine functional groups can be converted to a wide variety derivatives. Alternatively, derivatized Formula (I) compounds can be obtained by first derivatizing one or more intermediates in the processes of preparation before further transforming the derivatized intermediate to compounds of Formula (I). A hydroxyl group in the form of an alcohol or phenol can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. Similarly, carbamic acid esters (urethanes) can be obtained by reacting a hydroxyl group with isocyanates and carbamoyl chlorides. Sulfonate, phosphonate, and phosphate esters can be prepared using the corresponding acid chloride and similar reagents. Compounds of Formula (I) that have at least one thiol group present can be converted to the corresponding thioesters derivatives analogous to those of alcohols and phenols using the same reagents and comparable reaction conditions. Compounds of Formula (I) that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide or a tertiary amine. Suitable procedures and methods for preparing these derivatives can be found in House's Modem Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Reagents of a wide variety that can be used to derivative hydroxyl, thiol, and amines of compounds of Formula (I) are available from commercial sources or the references cited above, which are incorporated herein by reference.

Formula (I) compounds of this invention possessing hydroxyl, thiol, and amine functional groups can be alkylated to a wide variety of derivatives. Alternatively, alkylated Formula (I) compounds can be obtained by first alkylating one or more intermediates in the processes of preparation before further transforming the alkylated intermediate to compounds of Formula (I). A hydroxyl group of compounds of Formula (I) can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents, amine catalyst such as pyridine in an inert solvent. Compounds of Formula (I) that have at least one thiol group present can be converted to the corresponding thioether derivatives analogous to those of alcohols and phenols using the same reagents and comparable reaction conditions. Compounds of Formula (I) that have at least one primary, secondary or tertiary amine group present can be converted to the corresponding secondary, tertiary or quaternary ammonium derivative. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Secondary or tertiary amines can be prepared from the corresponding primary or secondary amine. A primary amine can be dialkylated by reductive amination using an aldehyde, such as formaldehyde, and sodium cyanoborohydride in the presence of glacial acetic acid. A primary amine can be monoalkylated by first monoprotecting the amine with a ready cleaved protecting group, such as trifluoroacetyl. An alkylating agent, such as dimethylsulfate, of the presence of a non-nucleophilic base, such as Barton's base (2-tert-butyl-1,1,3,3-tetramethylguanidine), gives the monomethylated protected amine. Removal of the protecting group using aqueous potassium hydroxide gives the desired monoalkylated amine. Additional suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis published by John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formula (I) are available from commercial sources or the references cited above, which are incorporated herein by reference.

Assays for Biological Activity

TF-VIIa Assay

In this assay 100 nM recombinant soluble tissue factor and 2 nM recombinant human factor VIIa are added to a 96-well assay plate containing 0.4 mM of the substrate, N-Methylsulfonyl-D-phe-gly-arg-p-nitroaniline and either inhibitor or buffer (5 mM $CaCl_2$, 50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of TF-VIIa activity is calculated from $OD_{405\,nm}$ value from the experimental and control sample.

Xa Assay 0.3 nM human factor Xa and 0.15 mM N-α-Benzyloxycarbonyl-D-arginyl-L-glycyl-L-arginine-p-nitroaniline-dihydrochloride (S-2765) are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of Xa activity is calculated from $OD_{405\,nm}$ value from the experimental and control sample.

Thrombin Assay 0.28 nM human thrombin and 0.06 mM H-D-Phenylalanyl-L-pipecolyl-L-arginine-p-nitroaniline dihydrochloride are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of thrombin activity is calculated from $OD_{405\,nm}$ value from the experimental and control sample.

Trypsin Assay 5 ug/ml trypsin, type IX from porcine pancreas and 0.375 mM N-α-Benzoyl-L-arginine-p-nitroanilide (L-BAPNA) are added to a 96-well assay plate containing either inhibitor or buffer (50 mM Tris-HCl, pH 8.0, 100 mM NaCl, 0.1% BSA). The reactions, in a final volume of 100 ul are measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of trypsin activity is calculated from $OD_{405\,nm}$ value from the experimental and control sample.

Recombinant soluble TF, consisting of amino acids 1–219 of the mature protein sequence was expressed in E. coli and purified using a Mono Q Sepharose FPLC. Recombinant human VIIa was purchased from American Diagnostica, Greenwich Conn. and chromogenic substrate N-Methylsulfonyl-D-phe-gly-arg-p-nitroaniline was prepared by American Peptide Company, Inc., Sunnyvale, Calif. Factor Xa was obtained from Enzyme Research Laboratories, South Bend Ind., thrombin from Calbiochem, La Jolla, Calif., and trypsin and L-BAPNA from Sigma, St Louis Mo. The chromogenic substrates S-2765 and S-2238 were purchased from Chromogenix, Sweden.

The biological activity of the compounds of Examples 1 through 22 as determined by the bioassay procedures is summarized in the Table 1.

TABLE 1

Inhibitory Activity of Pyridones towards Factor Xa, TF-VIIA, Thrombin II, and Trypsin II.

| Example Number | TF-VIIA IC50 (uM) | Thrombin II IC50 (uM) | Factor Xa IC50 (uM) | Trpysin II IC50 (uM) |
|---|---|---|---|---|
| 1 | 4.6 | 0.7 | 0.07 | 0.21 |
| 2 | 46 | 5.5 | 7.7 | 0.5 |
| 3 | 26.1 | 11.0 | >30 | 0.86 |
| 4 | >30 | 22.7 | 23.1 | 0.48 |
| 5 | 40% | 40% | 27% | — |
| 6 | >30 | >30 | >30 | >30 |
| 7 | >30 | >30 | >30 | >30 |
| 8 | >30 | >30 | >30 | >30 |
| 9 | >30 | >30 | >30 | >30 |
| 10 | >30 | >30 | >30 | >30 |
| 11 | >30 | >30 | >30 | >30 |
| 12 | >30 | >30 | >30 | >30 |
| 13 | >30 | >30 | >30 | >30 |
| 14 | >30 | >30 | >30 | >30 |
| 15 | >30 | >30 | >30 | >30 |
| 16 | >30 | >30 | >30 | >30 |
| 17 | 1.1 | 0.2 | 0.1 | 0.3 |
| 18 | 0.8 | <0.04 | <4.0 | 0.2 |
| 19 | 18.0 | 0.4 | 4.1 | <0.1 |
| 20 | 23.0 | 0.3 | 5.7 | 0.5 |
| 21 | >30 | 0.5 | 17 | 0.6 |
| 22 | >30 | <0.04 | >0 | 11.1 |

What we claim is:

1. A compound having the formula:

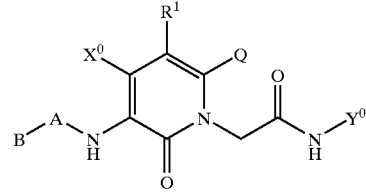

or a pharmaceutically acceptable salt thereof, wherein:

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$ and $R^{36}$;

$R^{32}$, $R^{33}$, $R^{34}$, $R^{35}$ and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of a single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

Q is selected from the group consisting of aryl and heteroaryl, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$ and $R^{13}$ are independently selected from the group consisting of hydrido, hydroxy, amino amidino, guanidino, alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, alkylamino, alkylsulfonamido, amidosulfonyl, monoalkyl amidosulfonyl, dialkyl amidosulfonyl, hydroxyalkyl, halo, haloalkyl, carboalkoxy, carboxy, carboxyalkyl, carboxamido, and cyano;

$Y^0$ is formula (IV):

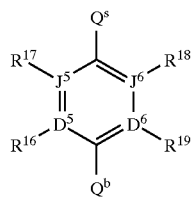

(IV)

wherein $D^5$, $D^6$, $J^5$, and $J^6$ are independently selected from the group consisting of C, N, O, S and a covalent bond with the provisos that no more than one is a covalent bond, no more than one of $D^5$, $D^6$, $J^5$ and $J^6$ is O, no more than one of $D^5$, $D^6$, $J^5$ and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, the trivalent nature of nitrogen, the divalent nature of sulfur, and the divalent nature of oxygen;

$R^{17}$ and $R^{18}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, cyano, and $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$ and $C(NR^{25})NR^{23}R^{24}$;

$R^{20}$, $R^{21}$, $R^{23}$, $R^{24}$, $R^{25}$ and $R^{26}$ are independently selected from the group consisting of hydrido and alkyl; and $Q^s$ is $CH_2$.

2. The compound of claim 1 wherein $Y^0$ is amidinoaralkyl or amidinoheteroaralkyl.

3. The compound of claim 2 wherein A is a single covalent bond, $X^0$ is hydrido and $R^1$ is hydrido or halo.

4. The compound of claim 3 wherein B is C2–C8 alkyl.

5. The compound of claim 4 wherein Q is

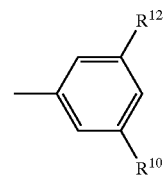

and $R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, alkylamino, alkylsulfonamido, amidosulfonyl, monoalkyl amidosulfonyl, dialkyl amidosulfonyl, hydroxyalkyl, halo, haloalkyl, carboalkoxy, carboxy, carboxyalkyl, carboxamido, and cyano.

6. The compound of claim 2 wherein Q is

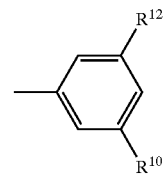

and $R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, alkylamino, alkylsulfonamido, amidosulfonyl, monoalkyl amidosulfonyl, dialkyl amidosulfonyl, hydroxyalkyl, halo, haloalkyl, carboalkoxy, carboxy, carboxyalkyl, carboxamido, and cyano.

7. The compound of claim 1 wherein the

8. The compound of claim 1 wherein the compound is

9. The compound of claim 1 wherein Q is 3-carboxamido-5-aminophenyl, B is 2-propyl, A is a single bond, $Y^o$ is 4-amidinobenzyl, $R^1$ is chloro and $X^o$ is hydrido.

10. The compound of claim 1 wherein Q is 3-amino-5-(N-benzylcarboxamido)phenyl, B is 2-propyl, A is a single bond, $Y^o$ is 4-amidinobenzyl, $R^1$ is chloro and $X^o$ is hydrido.

11. The compound of claim 1 wherein Q is 3-amino-5-(N-2chlorobenzyl)carboxamido)phenyl, B is 2-propyl, A is a single bond, $Y^o$ is 4-amidinobenzyl, $R^1$ is chloro and $X^o$ is hydrido.

12. The compound of claim 1 wherein Q is 3-amino-5-(N-(2-chlorobenzyl)amidosulfonyl)phenyl, B is 2-propyl, A is a single bond, $Y^o$ is 4-amidinobenzyl, $R^1$ is chloro and $X^o$ is hydrido.

13. The compound of claim 1 wherein Q is 3-amino-5-(N-trifluoromethylbenzyl)carboxamido)phenyl, B is 2-propyl, A is a single bond, $Y^o$ is 4-amidinobenzyl, $R^1$ is chloro and $X^o$ is hydrido.

14. The compound of claim 1 wherein Q is 3,5-diaminophenyl, B is 2-propyl, A is a single bond, $Y^o$ is 4-amidinobenzyl, $R^1$ is chloro and $X^o$ is hydrido.

15. The compound of claim 1 wherein Q is 3-amino-5-carboxyphenyl, B is 2-propyl, A is a single bond, $Y^o$ is 4-amidinobenzyl, $R^1$ is chloro and $X^o$ is hydrido.

16. The compound of claim 1 wherein Q is 3-carboxamido-5-aminophenyl, B is 2-propyl, A is a single bond, $Y^o$ is 4-amidinobenzyl, $R^1$ is hydrido and $X^o$ is hydrido.

17. The compound of claim 1 wherein Q is 3-amino-5-(N-benzylcarboxamido)phenyl, B is 2-propyl, A is a single bond, $Y^o$ is 4-amidinobenzyl, $R^1$ is hydrido and $X^o$ is hydrido.

18. The compound of claim 1 wherein Q is 3-amino-5-(N-(2-chlorobenzyl)carboxamido)phenyl, B is 2-propyl, A is a single bond, $Y^o$ is 4-amidinobenzyl, $R^1$ is hydrido and $X^o$ is hydrido.

19. The compound of claim 1 wherein Q is 3-amino-5-(N-(2-chlorobenzyl)amidosulfonyl)phenyl, B is 2-propyl, A is a single bond, $Y^o$ is 4-amidinobenzyl, $R^1$ is hydrido and $X^o$ is hydrido.

20. The compound of claim 1 wherein Q is 3-amino-5-(N-(trifluoromethylbenzyl)carboxamido)phenyl, B is 2-propyl, A is a single bond, $Y^o$ is 4-amidinobenzyl, $R^1$ is hydrido and $X^o$ is hydrido.

21. The compound of claim 1 wherein Q is 3-amino-5-carboxy-2-thienyl, B is (S)-2-butyl, A is a single bond, $Y^o$ is 4-amidinobenzyl, $R^1$ is hydrido and $X^o$ is hydrido.

22. The compound of claim 1 wherein Q is 3-amino-5-carboxy-2-thienyl, B is ethyl, A is a single bond, $Y^o$ is 4-amidinobenzyl, $R^1$ is hydrido and $X^o$ is hydrido.

23. The compound of claim 1 wherein Q is 3-amino-5-carboxy-2-thienyl, B is 2-propenyl, A is a single bond, $Y^o$ is 4-amidinobenzyl, $R^1$ is hydrido and $X^o$ is hydrido.

24. The compound of claim 1 wherein Q is 3-amino-5-carboxy-2-thienyl, B is isopropyl, A is a single bond, $Y^o$ is 4-amidinobenzyl, $R^1$ is hydrido and $X^o$ is hydrido.

25. The compound of claim 1 wherein Q is 3-amino-5-carboxy-2-thienyl, B is 2-butyl, A is a single bond, $Y^o$ is 4-amidinobenzyl, $R^1$ is hydrido and $X^o$ is hydrido.

26. The compound of claim 1 wherein Q is 3-amino-5-carboxy-2-thienyl, B is (R)-2-butyl, A is a single bond, $Y^o$ is 4-amidinobenzyl, $R^1$ is hydrido and $X^o$ is hydrido.

27. The compound of claim 1 wherein Q is 3-amino-5-carboxy-2-thienyl, B is 3-pentyl, A is a single bond, $Y^o$ is 4-amidinobenzyl, $R^1$ is hydrido and $X^o$ is hydrido.

28. The compound of claim 1 wherein Q is 3-amino-5-carboxy-2-thienyl, B is tert-butyl, A is a single bond, $Y^o$ is 4-amidinobenzyl, $R^1$ is hydrido and $X^o$ is hydrido.

29. The compound of claim 1 wherein Q is 3-amino-5-carboxy-2-thienyl, B is butyl, A is a single bond, $Y^o$ is 4-amidinobenzyl, $R^1$ is hydrido and $X^o$ is hydrido.

30. The compound of claim 1 wherein Q is 3-carboxamido-5-amino-2-thienyl, B is 2-propyl, A is a single bond, $Y^o$ is 4-amidinobenzyl, $R^1$ is chloro or hydrido and $X^o$ is hydrido.

31. The compound of claim 1 wherein Q is 3-amino-5-(N-benzylcarboxamido)-2-thienyl, B is 2-propyl, A is a single bond, $Y^o$ is 4-amidinobenzyl, $R^1$ is chloro or hydrido and $X^o$ is hydrido.

32. The compound of claim 1 wherein Q is 3-amino-5-N-(2-chlorobenzyl)carboxamido-2-thienyl, B is 2-propyl, A is a single bond, $Y^o$ is 4-amidinobenzyl, $R^1$ is chloro or hydrido and $X^o$ is hydrido.

33. The compound of claim 1 wherein Q is 3-amino-5-(N-(2-chlorobenzyl)amidosulfonyl)-2-thienyl, B is 2-propyl, A is a single bond, $Y^o$ is 4-amidinobenzyl, $R^1$ is chloro or hydrido and $X^o$ is hydrido.

34. The compound of claim 1 wherein Q is 3-amino-5-N-(trifluoromethylbenzyl)carboxamido)-2-thienyl, B is 2-propyl, A is a single bond, $Y^o$ is 4-amidinobenzyl, $R^1$ is chloro or hydrido and $X^o$ is hydrido.

35. The compound of claim 1 wherein Q is 3,5-diamino-2-thienyl, B is 2-propyl, A is a single bond, $Y^o$ is 4-amidinobenzyl, $R^1$ is chloro or hydrido and $X^o$ is hydrido.

36. The compound of claim 1 wherein Q is 3-amino-5-carboxy-2-thienyl, B is 2-propyl, A is a single bond, $Y^o$ is 4-amidinobenzyl, $R^1$ is chloro or hydrido and $X^o$ is hydrido.

* * * * *

UNITED STATES PATENT AND TRADEMARK OFFICE
CERTIFICATE OF CORRECTION

PATENT NO. : 6,870,056 B1
DATED : March 22, 2005
INVENTOR(S) : Michael S. South et al.

It is certified that error appears in the above-identified patent and that said Letters Patent is hereby corrected as shown below:

Title page,
Item [75], Inventors, "Qingieng Zeng" should read -- Qingping Zheng --.

Column 167,
Line 1, "wherein the" should read -- wherein the compound is --.
Line 34, "(N-2chlorobenzyl)carboxamido)phenyl," should read -- (N-(2-chlorobenzyl)carboxamido)phenyl, --.

Signed and Sealed this

Twelfth Day of July, 2005

JON W. DUDAS
*Director of the United States Patent and Trademark Office*